US012319927B2

(12) United States Patent
McDonald

(10) Patent No.: US 12,319,927 B2
(45) Date of Patent: Jun. 3, 2025

(54) GENETIC CONSTRUCT

(71) Applicants: Healing Genes LLC, New York, NY (US); Panacea Venture Healthcare Fund I, LP, Shanghai (CN)

(72) Inventor: Michael McDonald, Guildford (GB)

(73) Assignees: Healing Genes LLC, New York, NY (US); Panacea Venture Healthcare Fund I, LP, Shanghai (CN)

( * ) Notice: Subject to any disclaimer, the term of this patent is extended or adjusted under 35 U.S.C. 154(b) by 599 days.

(21) Appl. No.: 16/616,302

(22) PCT Filed: May 25, 2018

(86) PCT No.: PCT/GB2018/051428
§ 371 (c)(1),
(2) Date: Nov. 22, 2019

(87) PCT Pub. No.: WO2018/215787
PCT Pub. Date: Nov. 29, 2018

(65) Prior Publication Data

US 2020/0157569 A1 May 21, 2020

(30) Foreign Application Priority Data

May 25, 2017 (GB) .................................... 1708385

(51) Int. Cl.

| | |
|---|---|
| ***C12N 15/86*** | (2006.01) |
| ***A61K 48/00*** | (2006.01) |
| ***A61P 25/28*** | (2006.01) |
| ***C12N 9/02*** | (2006.01) |
| ***C12N 9/78*** | (2006.01) |

(52) U.S. Cl.

CPC .............. *C12N 15/86* (2013.01); *A61P 25/28* (2018.01); *C12N 9/0071* (2013.01); *C12N 9/78* (2013.01); *C12Y 114/16002* (2013.01); *C12Y 305/04016* (2013.01); *A61K 48/00* (2013.01); *C12N 2750/14132* (2013.01); *C12N 2750/14143* (2013.01)

(58) Field of Classification Search

CPC ........ C12N 15/86; C12N 9/0071; C12N 9/78; C12N 2750/14132; C12N 2750/14143; C12N 2830/34; C12N 2830/40; C12N 2830/42; C12N 2830/50; C12N 2830/60; C12N 2830/85; C12N 15/85; C12N 9/14; C12N 15/62; C12N 2750/00043; A61P 25/28; C12Y 114/16002; C12Y 305/04016; A61K 48/00

See application file for complete search history.

(56) References Cited

U.S. PATENT DOCUMENTS

| | | | | |
|---|---|---|---|---|
| 2012/0309816 A1* | 12/2012 | Bjorklund | ................ | C12N 9/78 435/320.1 |
| 2017/0114346 A1* | 4/2017 | Kirik | ...................... | C12N 15/86 |

FOREIGN PATENT DOCUMENTS

| | | | |
|---|---|---|---|
| WO | 2010/055209 A1 | 5/2010 | |
| WO | 2011/054976 A2 | 5/2011 | |
| WO | 2013/061076 | 5/2013 | |
| WO | WO-2013061076 A1 * | 5/2013 | ............. A61K 38/54 |
| WO | 2013/119371 | 8/2013 | |
| WO | 2015/152813 A1 | 10/2015 | |
| WO | 2018/215787 A1 | 11/2018 | |

OTHER PUBLICATIONS

Cederfjall et al., "Design of a Single AAV Vector for Coexpression of TH and GCH1 to Establish Continuous DOPA Synthesis in a Rat Model of Parkinson's Disease," Moleculer Therapy: The Journal of the American Society of Gene Therapy, vol. 20, No. 7, Jan. 31, 2012, pp. 1315-1326.

International Search Report, International Application No. PCT/GB2018/051428, dated Jul. 13, 2018, 5 pages.

Muramatsu et al., "Behavioral Recovery in a Primate Model of Parkinson's disease by Tripe Transduction of Striatal Cells with Adena-Associated Viral (AA V) Vectors Expressing dopamine-Synthesizing Enzymes," Human Gene Therapy, Feb. 10, 2002, 12: 345-354.

Jarraya, et al., "Dopamine Gene Therapy for Parkinson's Disease in a Nonhuman Primate Without Associated Dyskinesia," Science Translational Medicine, Oct. 14, 2009, vol. 1 Issue 2, 13 pages.

Cederfjall E et al., Continuous DOPA synthesis from a single AA V: dosing and efficacy in models of Parkinson's disease, Scientific Reports, Jul. 2013, vol. 3, 2157, 13 pages.

Kirik D, et al., "Reversal of motor impairments in parkinsonian rats by continuous intrastriatal delivery ofL-DOPA using rAAV-mediated gene transfer," PNAS, 2002, 99, 4708-13.

Hennecke et al., "Composition and arrangement of genes define the strength of IRES-driven translation in bicistronic mRNAs," Nucleic Acids Research, 2001, vol. 29, No. 16, p. 3327-3334.

Daubner SC, Lohse DL, Fitzpatrick PF, "Expression and characterization of catalytic and regulatory domains of rat tyrosine hydroxylase," Protein Sci. 1993;2:1452-60.

Furler et al., "Recombinant AAV vectors containing the foot and mouth disease virus 2A sequence confer efficient bicistronic gene expression in cultured cells and rat substantia nigra neurons," Gene Ther. 2001, 8, pp. 864-873.

Lu et al., "A 5' Noncoding Exon Containing Engineered Intron Enhances Transgene Expression from Recombinant AAV Vectors in vivo", Human Gene Therapy, vol. 28, 2017, p. 125-134.

(Continued)

*Primary Examiner* — Jeremy C Flinders
*Assistant Examiner* — Alexander W Nicol
(74) *Attorney, Agent, or Firm* — Martin Fessenmaier; Umberg Zipser LLP

(57) ABSTRACT

A genetic construct comprises a promoter operably linked to a first coding sequence, which encodes tyrosine hydroxylase (TH), and a second coding sequence, which encodes GTP cyclohydrolase 1 (GCH1), wherein the second coding sequence is 3' to the first coding sequence, and the first and second coding sequences are part of a single operon. The genetic construct does not encode aromatic amino acid decarboxylase (AADC).

14 Claims, 15 Drawing Sheets

Specification includes a Sequence Listing.

(56) References Cited

OTHER PUBLICATIONS

Matsushita et al., "Adeno-associated virus vectors can be efficiently produced without helper virus," Gene Therapy (1998) 5, 938-945.

Bilang-Bleuel et al., "Intrastriatal Injection of an Adenoviral Vector Expressing Glial-Cell-Line-Derived Neurotrophic Factor Prevents Dopaminergic Neuron Degeneration and Behavioral Impairment in a Rate Model of Parkinson Disease," (1997) Proc. Acad. Nati. Sci. USA 94:8818-8823.

Mandel et al., "Midbrain Injection of Recombinant Adeno-Associated Virus Encoding Rat Glial Cell Line-Derived Neurotrophic Factor Protects Nigral Neurons in a Progressive 6-Hydroxydopamine-Inducated Degeneration Model of Parkinson's Disease in Rates," (1997)) Proc. Acad. Natl. Sci. USA 94:14083-14088.

Thompson et al., "Clustal W: Improving the Sensitivity of Progressive Multiple Sequence Alignmnet through Sequence Weighting, Position-Specific Gap Penalities and Weight Matrix Choice," 1994, NucleicAcids Research, 22, 4673-4680.

Thompson et al., "The CLUSTAL_X windows interface: flexible strategie for multiple sequence alignment aided by quality analysis tools," 1997, Nucleic Acids Research, vol. 25, No. 24, pp. 4876-4882.

Olsson, M., et al., "Forelimb akinesia in the rat Parkinson model: differential effects of dopamine agonists and nigral transplants as assessed by a new stepping test," J Neurosci 15, 3863-3875 (1995).

Lees, "The Important of Steady-State Plasma DOPA Levels in Reducing Motor Fluctuations in Parkinson's Disease," CNS Spectr 13:4 (Suppl 7), Apr. 2008, pp. 4-7.

Palfi et al., "Long-Term Follow-up of a Phase I/II Study of ProSavin, a Lentiviral Vector Gene Therapy for Parkinson's Disease," Human Gene Therapy Clinical Development, vol. 29, No. 3, 2018, pp. 148-155.

Choi-Lundberg et al., Behavior and Cellular Protection or Rat Dopaminergic Neurons by an Adenoviral Vector Encoding Glial Cell Line-Derived Neutrotrophic Factor, Experimental Neurology, 154, (1998) pp. 261-275.

Choi-Lundberg et al., "Dopaminergic Neurons Protected from Degeneration by GDNF Gene Therapy," Science, vol. 275, Feb. 7, 1997, pp. 838-841.

* cited by examiner

GENETIC CONSTRUCT

CROSS REFERENCE TO RELATED APPLICATIONS

This application is the National Stage of International Application No. PCT/GB2018/051428, filed on May 25, 2018, which International Application claims the right of priority based on GB application serial no. 1708385.8, filed on May 25, 2017, which applications are herein incorporated by reference in their entirety.

SEQUENCE LISTING

The instant application contains a Sequence Listing which has been submitted via EFS- Web and is hereby incorporated by reference in its entirety. Said ASCII copy, created on Nov. 19, 2019, is named VNN-784WOUS_CRF_sequence_listing.txt, and is 90,638 bytes in size.

The present invention relates to genetic constructs and recombinant vectors comprising such constructs, and to the uses of the constructs and vectors in gene therapy methods for treating neurodegenerative disorders, such as Parkinson's disease.

Parkinson's disease is a neurodegenerative disease associated with the loss of dopamine-producing cells in the striatum. There are three enzymes which are necessary for the production of dopamine by brain cells: tyrosine hydroxylase (TH), GTP cyclohydrolase 1 (GCH1) and aromatic amino acid decarboxylase (AADC). TH and GCH1 regulate the production of L-DOPA (a precursor to dopamine) from tyrosine, and AADC converts L-DOPA to dopamine. The current treatment options for Parkinson's disease include oral administration of L-DOPA, which, in contrast to dopamine, is absorbed across the blood-brain barrier. This treatment is efficacious because AADC is still present in the brains of Parkinson's disease patients.

Oral L-DOPA therapy can lead to side effects, such as abnormal movement. These side effects are believed to be due to the fluctuation levels of L-DOPA in blood and brain caused by the short half-life of L-DOPA and the variable absorption across the gut mucosa and blood brain barrier resulting from competition with other amino for active transport (Lees, April 2008, The Importance of Steady-State plasma DOPA levels in reducing motor fluctuations in Parkinson's disease, Expert Roundtable Supplement, CNS Spectr 13:4 (Suppl 7) P4-7).

Gene therapy for Parkinson's disease involves the transfer of a vector into the striatum, where the vector carries genes necessary for the production of dopamine or L-DOPA by brain cells that would ordinarily be non-dopamine producing. The aim of such treatment is the local generation of dopamine within the affected areas of the brains of Parkinson's patients. Several methods of gene therapy have been disclosed. However, while the technique has shown promise, and the previous methods provide a proof of the principle, previous vectors have not been optimal. In particular, there is a need for vectors that lead to optimal production of dopamine (either directly or indirectly via L-DOPA) in the brains of Parkinson's patients, and which can be manufactured at suitable levels and with suitable cost effectiveness to be a viable treatment option.

Muramatsu et al. (10 February, 2002, Behavioral Recovery in a Primate Model of Parkinson's disease by Tripe Transduction of Striatal Cells with Adeno-Associated Viral (AAV) Vectors Expressing dopamine-Synthesizing Enzymes, Human Gene Therapy, 12: 345-354) conducted the first study to show complete recovery on a primate model of Parkinson's disease by transfer of the genes for TH, GCH and AADC into the striatum. This was achieved by administering three types of vector, one for each of TH, GCH1 and AADC. This approach had two significant issues: (1) the ratio of genes transfected to any particular neuron is random, and (2) the cost involved in manufacturing and releasing three separate vectors is prohibitive. As a result, the approach was never advanced to a clinical product. Expressing all three genes within a single AAV vector was not possible because the size of the genes exceeded what could be accommodated within the vector.

To overcome this limitation, a lentiviral vector construct was disclosed for use in treating Parkinson's disease (WO2013/061076 and WO2010/055209). This used a much larger lentiviral vector to accommodate all three genes, TH, GCH1 and AADC within a single vector (Jarraya, et al., 14 Oct. 2009, Dopamine Gene Therapy for Parkinson's Disease in a Nonhuman Primate Without Associated Dyskinesia, Science Translational Medicine, Vol 1 Issue 2). This showed promising results in non-human primates, but when tested in a clinical trial, the magnitude of efficacy reported was only within the placebo range reported in other clinical trials for Parkinson's disease using surgical techniques (Palfi et al., 29 Mar. 2014, Long-term safety and tolerability of ProSavin, a lentiviral vector-based gene therapy for Parkinson's disease: a dose escalation, open-label, phase ½ trial, The Lancet, Vol 383). The limited efficacy observed, and failure in producing, and dose, lentivector at sufficient titres resulted in a decision by the originators to discontinue clinical development of the product.

As L-DOPA administered orally or intravenously was known to be effective in reversing the motor symptoms of Parkinson's disease it was apparent that Parkinson's disease patients retained sufficient AADC activity in the brain to convert L-DOPA to dopamine. Cederfjall E. et al therefore developed a single AAV vector co expressing TH and GCH1 (WO2011/054976 and WO2015152813). This construct was effective in completely reversing motor symptoms in the rat 6-OHDA model of Parkinson's disease but failed in a non-human primate model. Post-mortem assessments of transgene expression in the treated macaques demonstrated robust expression of GCH1, and GFP controls, but not TH. This was in contrast to the finding in rodents using the same vector preparation where robust expression of both TH and GCH1 was observed. Cederfjall et al subsequently wrote "The reason for the lack of transgenic TH expression by histology and lack of DOPA and dopamine production by microdialysis remains unclear at this time. However, this problem requires a solution prior to the initiation of clinical trials utilizing this approach." (Cederfjall E et al July 2013 Continuous DOPA synthesis from a single AAV: dosing and efficacy in models of Parkinson's disease, Scientific Reports, Vol 3).

Segawa syndrome is a rare (orphan) indication due to mutations of the guanosine triphosphate cyclohydrolase I (GCH-1) gene. The GCH-1 gene mutation is inherited as an autosomal dominant trait or occurs as a spontaneous genetic change (i.e., new mutation). Due to the rareness of Segawa syndrome it may not be commercially attractive or viable to develop a treatment for this indication.

There is therefore a need for improved constructs suitable for use in treating neurodegenerative diseases, in particular diseases associated with catecholamine dysfunction, for instance Parkinson's disease.

The inventor has constructed a novel genetic construct, which leads to improved production of GCH1 and TH, and hence is suitable for use with an improved method of treatment for neurodegenerative diseases, in particular diseases associated with catecholamine dysfunction, such as Parkinson's disease.

Thus, according to a first aspect of the invention, there is provided a genetic construct comprising a promoter operably linked to a first coding sequence, which encodes tyrosine hydroxylase (TH), and a second coding sequence, which encodes GTP cyclohydrolase 1 (GCH1), wherein the second coding sequence is 3' to the first coding sequence, and the first and second coding sequences are part of a single operon, and wherein the genetic construct does not encode aromatic amino acid decarboxylase (AADC).

The genetic construct of the first aspect, which comprises TH and GCH1, but which does not include AADC, is advantageous for several reasons. Firstly, the construct guarantees that the two genes, TH and GCH1, are delivered to the same cells in a subject being treated. Furthermore, the costs and difficulties associated with the production of multiple vectors, as would be required if the genes were present in different constructs, as in the prior art, are avoided. The inclusion of TH and GCH1 without AADC is advantageous because the delivery of these two polypeptides is sufficient for a therapeutic effect (Kirik D, et al., Reversal of motor impairments in parkinsonian rats by continuous intrastriatal delivery of L-DOPA using rAAV-mediated gene transfer. PNAS, 2002, 99, 4708-13), and allows a more efficacious and easier to manufacture smaller vector. For instance, the size limitation of rAAV vectors will prevent the incorporation of large gene constructs, reducing the production titres and efficacy.

WO2013/061076 and WO2010/055209 disclose expression constructs encoding TH, GCH1 and AADC, and their use in Parkinson's disease, and both documents regard all three proteins as being essential to provide a therapeutic effect. Furthermore, both documents are silent on the advantages of using a single promoter approach, as provided in the genetic construct of the first aspect. Thus, these documents teach that, TH, GCH1 and AADC are required to produce a therapeutic effect, and that fusions of these proteins may be particularly effective. However, these documents are silent on the advantages or disadvantages of different promoter set-ups. This is important, as single constructs comprising all three proteins TH, GCH1 and AADC have insufficient efficacy, and it is not possible to get a high enough titre to produce a therapeutic effect.

WO2011/054976 and WO2015152813 disclose an AAV vector which comprises GCH1 driven by a promoter, and TH driven by a separate promoter. However, as shown in FIG. 1, the inventor of the construct of the first aspect has tested the construct described in WO2011/054976, and clearly demonstrated that it does not achieve optimal levels of TH or GCH-1 expression, and is therefore not an optimal construct for use in gene therapy. Before the data presented herein, the skilled person would have been unaware of the sub-optimal expression of the construct of WO2011/054976. While variants of this construct were disclosed in WO2011/054976, the data are provided for the dual promoter construct, and the disclosure cautioned against variants which would be likely to have unpredictable, and hence negative, effects.

The term "operon" can mean a group of linked genes that produce a single messenger RNA molecule during transcription. Thus, the first coding sequence and the second coding sequence are under the control of the same promoter. The construct does not include a separate promoter for each cistron.

It is particularly important during gene therapy for a genetic construct to lead to high levels of the encoded polypeptides, because greater production of TH and GCH1 can lead to a greater therapeutic effect. However, small variations between constructs can lead to large and unpredictable differences in gene expression. For instance, Hennecke et al. state "These observations led us to conclude that IRES-dependent translation is not predictable and obviously depends on the composition of the mRNA" (Hennecke et al. Composition and arrangement of genes define the strength of IRES-driven translation in bicistronic mRNAs. Nucleic Acids Research, 2001, Vol. 29, No. 16, P3327-3334). Furthermore, the theoretical maximal level of polypeptide production for TH and GCH1 is not known; new constructs are tested by examining the relative expression of the genes in comparison to controls. Hence, it is only possible with hindsight to recognise non-optimal vectors. Without wishing to be bound to any particular theory, the inventor has surprisingly found that a separate promoter approach, as taught in the prior art, results in problematic interference between the promoters, such that the expression of one or both genes is reduced to sub-therapeutic levels.

The inventor presents data herein that show that the disclosed genetic constructs lead to improved production of TH and GCH1 in comparison to the prior art constructs (FIG. 1, FIG. 2, Table 1, and Table 2). It is only with hindsight, based upon this new data, that the inventor has identified problems with the prior art constructs. Furthermore, the inventor has shown, in vivo, that improved production of the disclosed genetic constructs leads to a significantly increased efficacy in a Parkinson's disease rat model in comparison to the prior art constructs (FIG. 15).

It is particularly surprising that the construct of the first aspect leads to improved expression over the co-administration of the monocistronic constructs, and this could not have been predicted. The technical prejudice of the skilled person is that monocistronic constructs lead to the highest level of expression, and that bicistronic constructs would not be as effective. However, the new data disclosed herein, for the first time indicate that constructs which correspond to embodiments of the first aspect (Test 1, Test 2, and Test 3) actually lead to surprisingly higher mRNA expression than the co-administered monocistronic constructs (Test 4). The full details of the experiments and the resultant data are disclosed in the Examples section.

Furthermore, the construct of the first aspect leads to improved expression the bicistronic construct of WO 2011/054976 A2. The reference construct described in the Examples corresponds to the construct disclosed by WO 2011/054976 A2. As can be seen, the present genetic constructs have surprisingly improved TH and GCH1 expression. The full details of the experiments and the resultant data are disclosed in the Examples section.

It is especially surprising that the constructs of the invention lead to improved expression of a 3' GCH1 over both the prior art bicistronic construct and over co-administration of the two monocistronic constructs. In general, it is expected that the 3' gene in a bicistronic construct may be expressed at a lower level than if the gene were 5'. Accordingly, it is very surprising that the construct with a 3' GCH1 is able to produce improved levels of GCH1, even over constructs comprising a 5' GCH1.

In an embodiment, the relative expression of TH is 1.1 to 100 fold higher than the expression of TH from a reference construct comprising a first promoter sequence operably linked to a sequence encoding GCH1 and a second promoter sequence is operably linked to a sequence encoding TH. In an embodiment, the relative expression is 1.5 to 20 fold higher, 2 to 15 fold higher, or between 3 and 10 fold higher. In an embodiment, the reference construct is the construct described as the reference construct in the Examples. In an embodiment, the in vitro assay to determine the level of expression is the in vitro assay disclosed in the Examples. In an embodiment, the relative expression is assayed using 0.25 μg of plasmid for transfection. In an embodiment, the relative expression is assayed using 0.0625 μg of plasmid for transfection.

In an embodiment, the relative expression of GCH1 is 1.1 to 10 fold higher than the expression of GCH1 from a reference construct comprising a first promoter sequence operably linked to a sequence encoding GCH1 and a second promoter sequence operably linked to a sequence encoding TH. In an embodiment, the relative expression is 1.2 to 5 fold higher, or between 2 to 4 fold higher. In an embodiment, the reference construct is the construct described as the reference construct in the Examples. In an embodiment, the in vitro assay to determine the level of expression is the in vitro assay disclosed in the Examples. In an embodiment, the relative expression is assayed using 0.25 μg of plasmid for transfection. In an embodiment, the relative expression is assayed using 0.0625 μg of plasmid for transfection.

In one embodiment, the first coding sequence comprises a nucleotide sequence encoding human TH. The nucleotide sequence encoding human TH is referred to herein as SEQ ID No:1, or a fragment or variant thereof, as set out below:

[SEQ ID NO: 1]

```
atgcccacccccgacgccaccacgccacaggccaagggcttccgcagg
gccgtgtctgagctggacgccaagcaggcagaggccatcatgtccccg
cggttcattgggcgcaggcagagcctcatcgaggacgcccgcaaggag
cgggaggcggcggtggcagcagcggccgctgcagtcccctcggagccc
ggggacccccctggaggctgtggcctttgaggagaaggaggggaaggcc
gtgctaaacctgctcttctccccgagggccaccaagccctcggcgctg
tcccgagctgtgaaggtgtttgagacgtttgaagccaaaatccaccat
ctagagacccggcccgcccagaggccgcgagctgggggcccccacctg
gagtacttcgtgcgcctcgaggtgcgccgaggggacctggccgccctg
ctcagtggtgtgcgccaggtgtcagaggacgtgcgcagccccgcgggg
cccaaggtcccctggttcccaagaaaagtgtcagagctggacaagtgt
catcacctggtcaccaagttcgaccctgacctggacttggaccacccg
ggcttctcggaccaggtgtaccgccagcgcaggaagctgattgctgag
atcgccttccagtacaggcacggcgacccgattccccgtgtggagtac
accgccgaggagattgccacctggaaggaggtctacaccacgctgaag
ggcctctacgccacgcacgcctgcggggagcacctggaggcctttgct
ttgctggagcgcttcagcggctaccgggaagacaatatcccccagctg
gaggacgtctcccgcttcctgaaggagcgcacgggcttccagctgcgg
cctgtggccggcctgctgtccgcccgggacttcctggccagcctggcc
ttccgcgtgttccagtgcacccagtatatccgccacgcgtcctcgccc
atgcactcccctgagccggactgctgccacgagctgctggggcacgtg
cccatgctggccgaccgcaccttcgcgcagttctcgcaggacattggc
```

-continued

```
ctggcgtccctgggggcctcggatgaggaaattgagaagctgtccacg
ctgtactggttcacggtggagttcgggctgtgtaagcagaacggggag
gtgaaggcctatggtgccgggctgctgtcctcctacggggagctcctg
cactgcctgtctgaggagcctgagattcgggccttcgaccctgaggct
gcggccgtgcagccctaccaagaccagacgtaccagtcagtctacttc
gtgtctgagagcttcagtgacgccaaggacaagctcaggagctatgcc
tcacgcatccagcgccccttctccgtgaagttcgacccgtacacgctg
gccatcgacgtgctggacagccccaggccgtgcggcgctccctggag
ggtgtccaggatgagctggacacccttgcccatgcgctgagtgccatt
ggctag
```

Preferably, therefore, the first coding sequence comprises a nucleotide sequence substantially as set out in SEQ ID No:1, or a fragment or variant thereof.

In one preferred embodiment, the first coding sequence comprises a nucleotide sequence encoding human TH. Human TH may have an amino acid sequence according to NCBI Reference Sequence: NP_000351.2, which is referred to herein as SEQ ID NO: 21, or a fragment or variant thereof, as set out below:

[SEQ ID NO: 21]

```
MPTPDATTPQAKGFRRAVSELDAKQAEAIMSPRFIGRRQSLIEDARKER
EAAVAAAAAAVPSEPGDPLEAVAFEEKEGKAVLNLLFSPRATKPSALSR
AVKVFETFEAKIHHLETRPAQRPRAGGPHLEYFVRLEVRRGDLAALLSG
VRQVSEDVRSPAGPKVPWFPRKVSELDKCHHLVTKFDPDLDLDHPGFSD
QVYRQRRKLIAEIAFQYRHGDPIPRVEYTAEEIATWKEVYTTLKGLYAT
HACGEHLEAFALLERFSGYREDNIPQLEDVSRFLKERTGFQLRPVAGLL
SARDFLASLAFRVFQCTQYIRHASSPMHSPEPDCCHELLGHVPMLADRT
FAQFSQDIGLASLGASDEEIEKLSTLYWFTVEFGLCKQNGEVKAYGAGL
LSSYGELLHCLSEEPEIRAFDPEAAAVQPYQDQTYQSVYFVSESFSDAK
DKLRSYASRIQRPFSVKFDPYTLAIDVLDSPQAVRRSLEGVQDELDTLA
HALSAIG*
```

Preferably, therefore, the first coding sequence comprises a nucleotide sequence encoding an amino acid sequence substantially as set out in SEQ ID No:21, or a fragment or variant thereof.

In another embodiment, the first coding sequence comprises a nucleotide sequence encoding human truncated TH. Human truncated TH is a variant of TH with only the catalytic domain, and with the regulatory domain removed. The domains of TH and their roles are described in Daubner et al. (Daubner S C, Lohse D L, Fitzpatrick' PF. Expression and characterization of catalytic and regulatory domains of rat tyrosine hydroxylase. Protein Sci. 1993; 2:1452-60). Human truncated TH comprises the nucleotide sequence referred to herein as SEQ ID No:2, or a fragment or variant thereof, as set out below:

[SEQ ID NO: 2]

```
atgagccccgcggggcccaaggtcccctggttcccaagaaaagtgtcag
agctggacaagtgtcatcacctggtcaccaagttcgaccctgacctgga
cttggaccacccgggcttctcggaccaggtgtaccgccagcgcaggaag
ctgattgctgagatcgccttccagtacaggcacggcgacccgattcccc
gtgtggagtacaccgccgaggagattgccacctggaaggaggtctacac
cacgctgaagggcctctacgccacgcacgcctgcggggagcacctggag
gcctttgctttgctggagcgcttcagcggctaccgggaagacaatatcc
cccagctggaggacgtctcccgcttcctgaaggagcgcacgggcttcca
gctgcggcctgtggccggcctgctgtccgcccgggacttcctggccagc
ctggccttccgcgtgttccagtgcacccagtatatccgccacgcgtcct
cgcccatgcactcccctgagccggactgctgccacgagctgctggggca
cgtgcccatgctggccgaccgcaccttcgcgcagttctcgcaggacatt
ggcctggcgtccctgggggcctcggatgaggaaattgagaagctgtcca
cgctgtactggttcacggtggagttcgggctgtgtaagcagaacgggga
ggtgaaggcctatggtgccgggctgctgtcctcctacggggagctcctg
cactgcctgtctgaggagcctgagattcgggccttcgaccctgaggctg
cggccgtgcagccctaccaagaccagacgtaccagtcagtctacttcgt
gtctgagagcttcagtgacgccaaggacaagctcaggagctatgcctca
cgcatccagcgccccttctccgtgaagttcgacccgtacacgctggcca
tcgacgtgctggacagcccccaggccgtgcggcgctccctggagggtgt
ccaggatgagctggacacccttgcccatgcgctgagtgccattggctag
```

Preferably, therefore, the first coding sequence comprises a nucleotide sequence substantially as set out in SEQ ID No:2, or a fragment or variant thereof.

In one preferred embodiment, the first coding sequence comprises a nucleotide sequence encoding human truncated TH. Human truncated TH comprises an amino acid sequence referred to herein as SEQ ID NO: 22, or a fragment or variant thereof, as set out below:

[SEQ ID NO: 22]

```
MSPAGPKVPWFPRKVSELDKCHHLVTKFDPDLDLDHPGFSDQVYRQRRK
LIAEIAFQYRHGDPIPRVEYTAEEIATWKEVYTTLKGLYATHACGEHLE
AFALLERFSGYREDNIPQLEDVSRFLKERTGFQLRPVAGLLSARDFLAS
LAFRVFQCTQYIRHASSPMHSPEPDCCHELLGHVPMLADRTFAQFSQDI
GLASLGASDEEIEKLSTLYWFTVEFGLCKQNGEVKAYGAGLLSSYGELL
HCLSEEPEIRAFDPEAAAVQPYQDQTYQSVYFVSESFSDAKDKLRSYAS
RIQRPFSVKFDPYTLAIDVLDSPQAVRRSLEGVQDELDTLAHALSAIG*
```

Preferably, therefore, the first coding sequence comprises a nucleotide sequence encoding an amino acid sequence substantially as set out in SEQ ID No:22, or a fragment or variant thereof.

In an embodiment, the second coding sequence comprises a nucleotide sequence encoding murine GCH1. The nucleotide sequence encoding murine GCH1 is referred to herein as SEQ ID No:3, or a fragment or variant thereof:

[SEQ ID NO: 3]

```
ggtggttttcctttgaaaaacacgatgataatatggccacaaccgcggc
cgtagatcccgggaccatggagaagccgcggggagtcaggtgcaccaat
gggttctccgagcgggagctgccgcggcccggggccagcccgcctgccg
agaagtcccggccgcccgaggccaagggcgcacagccggccgacgcctg
gaaggcagggcggcaccgcagcgaggaggaaaaccaggtgaacctcccc
aaactggcggctgcttactcgtccattctgctctcgctgggcgaggacc
cccagcggcaggggctgctcaagacgccctggagggcggccaccgccat
gcagtacttcaccaagggataccaggagaccatctcagatgtcctgaat
gatgctatatttgatgaagatcatgacgagatggtgattgtgaaggaca
tagatatgttctccatgtgtgagcatcaccttgttccatttgtaggaag
ggtccatattggctatcttcctaacaagcaagtccttggtctcagtaaa
cttgccaggattgtagaaatctacagtagacgactacaagttcaagagc
gcctcaccaaacagattgcggtggccatcacagaagccttgcagcctgc
tggcgttggagtagtgattgaagcgacacacatgtgcatggtaatgcga
ggcgtgcagaaaatgaacagcaagactgtcactagcaccatgctgggcg
tgttccgggaagaccccaagactcgggaggagttcctcacactaatcag
gagctgag
```

Therefore, the second coding sequence may comprise a nucleotide sequence substantially as set out in SEQ ID No:3, or a fragment or variant thereof.

In a preferred embodiment, the second coding sequence comprises a nucleotide sequence encoding human GCH1. For example, the sequence encoding human GCH may be the sequence according to GenBank NM 000161.2. The nucleotide sequence encoding human GCH1 is referred to herein as SEQ ID No:4, or a fragment or variant thereof, as set out below:

[SEQ ID NO: 4]

```
atggagaagggccctgtgcgggcaccggcggagaagccgcggggcgcca
ggtgcagcaatgggttccccgagcgggatccgccgcggcccgggcccag
caggccggcggagaagcccccgcggcccgaggccaagagcgcgcagccc
gcggacggctggaagggcgagcggccccgcagcgaggaggataacgagc
tgaacctccctaacctggcagccgcctactcgtccatcctgagctcgct
gggcgagaacccccagcggcaagggctgctcaagacgccctggagggcg
gcctcggccatgcagttcttcaccaagggctaccaggagaccatctcag
atgtcctaaacgatgctatatttgatgaagatcatgatgagatggtgat
tgtgaaggacatagacatgttttccatgtgtgagcatcacttggttcca
tttgttggaaaggtccatattggttatcttcctaacaagcaagtccttg
gcctcagcaaacttgcgaggattgtagaaatctatagtagaagactaca
agttcaggagcgccttacaaaacaaattgctgtagcaatcacggaagcc
ttgcggcctgctggagtcggggtagtggttgaagcaacacacatgtgta
tggtaatgcgaggtgtacagaaaatgaacagcaaaactgtgaccagcac
aatgttgggtgtgttccgggaggatccaaagactcgggaagagttcctg
actctcattaggagctga
```

Preferably, therefore, the second coding sequence comprises a nucleotide sequence substantially as set out in SEQ ID No: 4, or a fragment or variant thereof.

In one preferred embodiment, the second coding sequence comprises a nucleotide sequence encoding human GCH1. Human GCH1 may have an amino acid sequence according to NCBI Reference Sequence: NP_00015.1. Human GCH1 comprises an amino acid sequence referred to herein as SEQ ID NO: 23, or a fragment or variant thereof, as set out below:

```
                                         [SEQ ID NO: 23]
MEKGPVRAPAEKPRGARCSNGFPERDPPRPGPSRPAEKPPRPEAKSAQP

ADGWKGERPRSEEDNELNLPNLAAAYSSILSSLGENPQRQGLLKTPWRA

ASAMQFFTKGYQETISDVLNDAIFDEDHDEMVIVKDIDMFSMCEHHLVP

FVGKVHIGYLPNKQVLGLSKLARIVEIYSRRLQVQERLTKQIAVAITEA

LRPAGVGVVVEATHMCMVMRGVQKMNSKTVTSTMLGVFREDPKTREEFL

TLIRS*
```

Preferably, therefore, the second coding sequence comprises a nucleotide sequence encoding an amino acid sequence substantially as set out in SEQ ID No:23, or a fragment or variant thereof.

The genetic construct according to the first aspect comprises a promoter. The promoter may be any suitable promoter, including a constitutive promoter, an activatable promoter, an inducible promoter, or a tissue-specific promoter. In a preferred embodiment, the promoter is a one enabling the generation of TH and GCH1 in the most suitable tissue or tissues for therapy. In an embodiment, the promoter is one that permits high expression in neurons, such as for example striatal neurons. The promoter may be a neuron-specific promoter.

In an embodiment, the promoter is the CMV promoter, one embodiment of which is referred to herein as SEQ ID NO: 25, as follows:

```
                                         [SEQ ID No: 25]
ACGCGTGGAGCTAGTTATTAATAGTAATCAATTACGGGGTCATTAGTTC

ATAGCCCATATATGGAGTTCCGCGTTACATAACTTACGGTAAATGGCCC

GCCTGGCTGACCGCCCAACGACCCCCGCCCATTGACGTCAATAATGACG

TATGTTCCCATAGTAACGTCAATAGGGACTTTCCATTGACGTCAATGGG

TGGAGTATTTACGGTAAACTGCCCACTTGGCAGTACATCAAGTGTATCA

TATGCCAAGTACGCCCCCTATTGACGTCAATGACGGTAAATGGCCCGCC

TGGCATTATGCCCAGTACATGACCTTATGGGACTTTCCTACTTGGCAGT

ACATCTACGTATTAGTCATCGCTATTACCATGGTGATGCGGTTTTGGCA

GTACATCAATGGGCGTGGATAGCGGTTTGACTCACGGGGATTTCCAAGT

CTCCACCCCATTGACGTCAATGGGAGTTTGTTTTGCACCAAAATCAACG

GGACTTTCCAAAATGTCGTAACAACTCCGCCCCATTGACGCAAATGGGC

GGTAGGCGTGTACGGTGGGAGGTCTATATAAGCAGAGCTCGTTTAGTGA

ACCGTCAGATCGCCTGGAGACGCCATCCACGCTGTTTTGACCTCCATAG

AAGACACCGGGACCGATCCAGCCTCC
```

In an embodiment, the promoter may be a human synapsin promoter. In an embodiment, the promoter is a human synapsin 1 promoter. One embodiment of the 469 nucleotide sequence encoding the human synapsin I (SYN I) promoter is referred to herein as SEQ ID NO: 5, as follows:

```
                                         [SEQ ID NO: 5]
CTGCAGAGGGCCCTGCGTATGAGTGCAAGTGGGTTTTAGGACCAGGATG

AGGCGGGGTGGGGGTGCCTACCTGACGACCGACCCCGACCCACTGGACA

AGCACCCAACCCCCATTCCCCAAATTGCGCATCCCCTATCAGAGAGGGG

GAGGGGAAACAGGATGCGGCGAGGCGCGTGCGCACTGCCAGCTTCAGCA

CCGCGGACAGTGCCTTCGCCCCCGCCTGGCGGCGCGCGCCACCGCCGCC

TCAGCACTGAAGGCGCGCTGACGTCACTCGCCGGTCCCCCGCAAACTCC

CCTTCCCGGCCACCTTGGTCGCGTCCGCGCCGCCGCCGGCCCAGCCGGA

CCGCACCACGCGAGGCGCGAGATAGGGGGGCACGGGCGCGACCATCTGC

GCTGCGGCGCCGGCGACTCAGCGCTGCCTCAGTCTGCGGTGGGCAGCGG

AGGAGTCGTGTCGTGCCTGAGAGCGCAG
```

Preferably, therefore, the promoter may comprise a nucleotide sequence substantially as set out in SEQ ID No: 5 or 25, or a fragment or variant thereof.

The genetic construct may further comprise one or more enhancer, which is configured to increase the expression of TH or GCH1. In particular, the construct may comprise an enhancer designed to cooperate with the promoter. As an example, a construct including a CMV promoter may also include a CMV enhancer.

In a preferred embodiment, the genetic construct comprises a spacer sequence disposed between the first and second coding sequences. This spacer sequence is such that it allows the production of functional TH and the production of functional GCH1 from the single promoter. In an embodiment, the spacer sequence comprises a sequence that allows for translation initiation in the middle of an mRNA sequence as part of the greater process of protein synthesis. In a particularly preferred embodiment, the spacer sequence comprises an internal ribosome entry site (IRES). The data presented herein clearly demonstrate that a construct including a 5' TH and a 3' GCH1 separated by an IRES leads to a surprisingly effective genetic construct (FIG. 1 and FIG. 2). In an embodiment, the IRES is a picornavirus IRES.

In other embodiments, the IRES may be selected from a rhinovirus IRES, a hepatitis A virus IRES, a hepatitis C virus IRES, a poliovirus IRES, an enterovirus IRES, a cardiovirus IRES, an aphthovirus IRES, flavivirus IRES, a pestivirus IRES, a cripavirus IRES, a *rhopalosiphum padi* virus IRES, or any suitable IRES. In particular, the IRES may be any IRES described by the "IRESite" which provides a database of experimentally verified IRES structures (http://www.iresite.org/), or as disclosed in "New Messenger RNA Research Communications" (ISBN: 1-60021-488-6).

In a preferred embodiment, the IRES is a foot-and-mouth disease virus (FMDV) IRES, which may be as set out in SEQ ID No:6, or a fragment or variant thereof, as follows:

```
                                         [SEQ ID NO: 6]
AGCAGGTTTCCCCAACTGACACAAAACGTGCAACTTGAAACTCCGCCTG

GTCTTTCCAGGTCTAGAGGGGTAACACTTTGTACTGCGTTTGGCTCCAC

GCTCGATCCACTGGCGAGTGTTAGTAACAGCACTGTTGCTTCGTAGCGG

AGCATGACGGCCGTGGGAACTCCTCCTTGGTAACAAGGACCCACGGGGC
```

-continued

```
CAAAAGCCACGCCCACACGGGCCCGTCATGTGTGCAACCCCAGCACGGC

GACTTTACTGCGAAACCCACTTTAAAGTGACATTGAAACTGGTACCCAC

ACACTGGTGACAGGCTAAGGATGCCCTTCAGGTACCCCGAGGTAACACG

CGACACTCGGGATCTGAGAAGGGGACTGGGGCTTCTATAAAAGCGCTCG

GTTTAAAAAGCTTCTATGCCTGAATAGGTGACCGGAGGTCGGCACCTTT

CCTTTGCAATTACTGACCAC
```

In another preferred embodiment, the IRES is an encephalomyocarditis virus (EMCV) IRES. The EMCV IRES may be as set out in SEQ ID No:7, or a fragment or variant thereof, as follows:

```
                                       [SEQ ID NO: 7]
cgttactggccgaagccgcttggaataaggccggtgtgcgtttgtctat

atgttattttccaccatattgccgtcttttggcaatgtgagggcccgga

aacctggccctgtcttcttgacgagcattcctaggggtctttcccctct

cgccaaaggaatgcaaggtctgttgaatgtcgtgaaggaagcagttcct

ctggaagcttcttgaagacaaacaacgtctgtagcgaccctttgcaggc

agcggaaccccccacctggcgacaggtgcctctgcggccaaaagccacg

tgtataagatacacctgcaaaggcggcacaaccccagtgccacgttgtg

agttggatagttgtggaaagagtcaaatggctcccctcaagcgtattca

acaaggggctgaaggatgcccagaaggtaccccattgtatgggatctga

tctggggcctcggtgcacatgctttcatgtgtttagtcgaggttaaaa

aacgtctaggccccccgaaccacggggacgtggttttcctttgaaaaac

acgatgataata
```

Therefore, preferably the IRES comprises a nucleotide sequence substantially as set out in SEQ ID No: 6 or 7, or a fragment or variant thereof.

Alternatively, instead of an IRES, the spacer sequence may comprise a nucleotide sequence encoding a peptide spacer that is configured to be digested to thereby produce the TH and GCH1 as separate molecules. Preferably, the spacer sequence comprises and encodes a viral peptide spacer sequence, more preferably a viral 2A peptide spacer sequence (Furler S, Paterna J-C, Weibel M and Bueler H Recombinant AAV vectors containing the foot and mouth disease virus 2A sequence confer efficient bicistronic gene expression in cultured cells and rat substantia nigra neurons Gene Ther. 2001, vol. 8, PP: 864-873). Preferably, the spacer sequence encoding the 2A peptide sequence connects the first coding sequence to the second coding sequence. This enables the construct to overcome the size restrictions that occur with expression in various vectors and enables expression of all of the peptides encoded by the construct of the first aspect to occur under control of a single promoter, as a single protein. Thus, following the translation of the single protein comprising the sequences of TH, the 2A peptide, and GCH1, cleavage occurs in the viral 2A peptide sequence at the terminal glycine-proline link, thereby liberating two proteins. The data presented herein demonstrate that a construct including a 5' TH and a 3' GCH1 separated by a viral 2A peptide spacer sequence leads to a surprisingly effective genetic construct (FIG. 1 and FIG. 2).

In an embodiment, the spacer comprises a viral 2A peptide spacer and further comprises a furin cleavage site. Insertion of an upstream furin cleavage site allows the removal of 2A residues that would otherwise remain attached to the upstream protein.

In an embodiment, the nucleotide sequence of a peptide spacer encoding both a viral 2A sequence and a furin cleavage site may be referred to herein as SEQ ID No:8, or a fragment or variant thereof, as follows:

```
                                       [SEQ ID NO: 8]
cgcgcgaaacgcgcgccggtgaaacagaccctgaactttgatctgctga

aactggcgggcgatgtggaaagcaacccgggcccg
```

Preferably, therefore, the spacer sequence comprises a nucleotide sequence substantially as set out in SEQ ID No: 8, or a fragment or variant thereof.

The 2A spacer sequence may be any known variant, which includes those sequences referred to as E2A, F2A, P2A and T2A, as disclosed in Wang Y et al. Scientific Reports 2015, 5.

In one embodiment, the sequence is E2A, referred to herein as SEQ ID No: 27, as follows:

```
                                      [SEQ ID NO: 27]
CAGTGTACTAATTATGCTCTCTTGAAATTGGCTGGAGATGTTGAGAGCA

ACCCTGGACCT
```

Preferably, therefore, the spacer sequence comprises a nucleotide sequence substantially as set out in SEQ ID No: 27, or a fragment or variant thereof.

In one embodiment, the sequence is F2A, referred to herein as SEQ ID No: 28, as follows:

```
                                      [SEQ ID NO: 28]
GTGAAACAGACTTTGAATTTTGACCTTCTCAAGTTGGCGGGAGACGTGG

AGTCCAACCCTGGACCT
```

Preferably, therefore, the spacer sequence comprises a nucleotide sequence substantially as set out in SEQ ID No: 28, or a fragment or variant thereof.

In one embodiment, the sequence is P2A, referred to herein as SEQ ID No: 29, as follows:

```
                                      [SEQ ID NO: 29]
GCCACGAACTTCTCTCTGTTAAAGCAAGCAGGAGATGTTGAAGAAAACC

CCGGGCCT
```

Preferably, therefore, the spacer sequence comprises a nucleotide sequence substantially as set out in SEQ ID No: 29, or a fragment or variant thereof.

In one embodiment, the sequence is T2A, referred to herein as SEQ ID No: 30, as follows:

```
                                      [SEQ ID NO: 30]
GAGGGCAGGGGAAGTCTTCTAACATGCGGGGACGTGGAGGAAAATCCCG

GCCCC
```

Preferably, therefore, the spacer sequence comprises a nucleotide sequence substantially as set out in SEQ ID No: 30, or a fragment or variant thereof.

In an embodiment, the 2A sequence may be preceded by any sequence that improves the efficiency of 2A, i.e. the sequence is positioned 5' to the 2A sequence. In an embodiment, the sequence that improves the efficiency of 2A is a glycine-serine-glycine spacer (GSG), referred to herein as SEQ ID No: 31, as follows:

```
[SEQ ID NO: 31]
GGAAGCGGA
```

Preferably, the 2A sequence is preceded by a nucleotide sequence substantially as set out in SEQ ID No: 31, or a fragment or variant thereof.

Alternatively, instead of an IRES or a viral 2A spacer, the spacer sequence may comprise a sequence encoding a flexible linker, which allows for the expression of both TH and GCH1 as a single polypeptide chain, but wherein the TH and GCH1 act as independent proteins. Hence, the proteins exert their effects in the same manner as if they were singly expressed. The data presented herein demonstrate that a construct including a 5' TH and a 3' GCH1 separated by spacer sequence comprising a flexible linker sequence leads to a surprisingly effective genetic construct (FIG. 1).

The flexible linker sequence may be as disclosed by WO 2013/061076 A1 (Oxford Biomedica), where this known linker was included in a tricistronic construct. The flexible linker sequence may be referred to herein as SEQ ID No:9, or a fragment or variant thereof, as follows:

```
[SEQ ID NO: 9]
ggaggtggcgggtccgggggcgggggtagcggtggcgggggctcc
```

Preferably, therefore, the flexible linker sequence comprises a nucleotide sequence substantially as set out in SEQ ID No: 9, or a fragment or variant thereof.

In one preferred embodiment, the flexible linker sequence comprises a nucleotide sequence encoding an amino acid sequence referred to herein as SEQ ID NO: 24, or a fragment or variant thereof, as set out below:

```
[SEQ ID NO: 24]
GGGGSGGGGSGGGGS
```

Preferably, therefore, the flexible linker sequence encodes an amino acid sequence substantially as set out in SEQ ID No: 24, or a fragment or variant thereof.

In an embodiment, the genetic construct may further comprise a nucleotide sequence encoding Woodchuck Hepatitis Virus Post-transcriptional Regulatory Element (WPRE), which enhances the expression of the two transgenes. Preferably, the WPRE coding sequence is disposed 3' of the transgene coding sequence. In particular, the WPRE sequence is preferably 3' of the GCH1 sequence.

One embodiment of the WPRE is 592 bp long, including gamma-alpha-beta elements, and is referred to herein as SEQ ID No: 10, as follows:

```
[SEQ ID NO: 10]
AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC
```

-continued

```
CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAGCTGACGTCCTTTCCATGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTG
```

Preferably, the WPRE comprises a nucleic acid sequence substantially as set out in SEQ ID No: 10, or a fragment or variant thereof.

However, in a preferred embodiment, a truncated WPRE is used, which is 247 bp long due to deletion of the beta element, and which is referred to herein as SEQ ID No: 11, as follows:

```
[SEQ ID NO: 11]
AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTAGTTCTTGCCACGGCGGAACTCATCGCCGCCTGCCTTG

CCCGCTGCTGGACAGGGGCTCGGCTGTTGGGCACTGACAATTCCGTGGT

GT
```

Preferably, the WPRE comprises a nucleic acid sequence substantially as set out in SEQ ID No: 11, or a fragment or variant thereof.

Preferably, the genetic construct comprises a nucleotide sequence encoding a polyA tail. Preferably, the polyA tail coding sequence is disposed 3' of the transgene coding sequence, and preferably 3' of the WHPE coding sequence.

Preferably, the polyA tail comprises the simian virus 40 poly-A 224 bp sequence. One embodiment of the polyA tail is referred to herein as SEQ ID No: 12, as follows:

```
[SEQ ID NO: 12]
AGCAGACATGATAAGATACATTGATGAGTTTGGACAAACCACAACTAGA

ATGCAGTGAAAAAAATGCTTTATTTGTGAAATTTGTGATGCTATTGCTT

TATTTGTAACCATTATAAGCTGCAATAAACAAGTTAACAACAACAATTG

CATTCATTTTATGTTTCAGGTTCAGGGGGAGGTGTGGGAGGTTTTTTAA

AGCAAGTAAAACCTCTACAAATGTGGTA
```

Preferably, the polyA tail comprises a nucleic acid sequence substantially as set out in SEQ ID No: 12, or a fragment or variant thereof.

Preferably, the genetic construct comprises left and/or right Inverted Terminal Repeat sequences (ITRs). Preferably, each ITR is disposed at the 5' and/or 3' end of the construct.

In a preferred embodiment, the genetic construct comprises, in this specified order, a 5' human synapsin 1 promoter or a CMV promoter; a sequence encoding human truncated TH; an IRES; and a 3' sequence encoding human GCH1. The use of 5' and 3' indicates that the features are either upstream or downstream, and is not intended to indicate that the features are necessarily terminal features.

In a preferred embodiment, the genetic construct may comprise, in this specified order, a 5' ITR; a human synapsin 1 promoter or a CMV promoter; a sequence encoding human truncated TH; an IRES; a sequence encoding human GCH1; a sequence encoding WPRE; a sequence encoding a poly A tail; and a 3' ITR.

In a particular embodiment the genetic construct may comprise, in this specified order, 5' ITR; a human synapsin 1 promoter or a CMV promoter; a sequence encoding human truncated TH; a Furin-2A sequence; a sequence encoding human GCH1; a sequence encoding WPRE; a sequence encoding a poly A tail; and a 3' ITR.

In a particular embodiment the genetic construct may comprise, in this specified order, a 5' ITR; a human synapsin 1 promoter or a CMV promoter; a sequence encoding human truncated TH; a flexible linker; a sequence encoding human GCH1; a sequence encoding WPRE; a sequence encoding a poly A tail; and a 3' ITR.

One embodiment of the genetic construct is shown in FIG. 10, and is referred to herein as SEQ ID No: 18. This particular embodiment includes a CMV promoter and murine GCH1; these features would be easily replaceable by the skilled person for other variants as disclosed herein.

```
                                          [SEQ ID NO: 18]
ggcgatcgcggctcccgacatcttggaccattagctccacaggtatctt

cttccctctagtggtcataacagcagcttcagctacctctcaattcaaa

aaacccctcaagacccgtttagaggccccaaggggttatgctatcaatc

gttgcgttacacacacaaaaaaccaacacacatccatcttcgatggata

gcgattttattatctaactgctgatcgagtgtagccagatctagtaatc

aattacggggtcattagttcatagcccatatatggagttccgcgttaca

taacttacggtaaatggcccgcctggctgaccgcccaacgacccccgcc

cattgacgtcaataatgacgtatgttcccatagtaacgccaatagggac

tttccattgacgtcaatgggtggagtatttacggtaaactgcccacttg

gcagtacatcaagtgtatcatatgccaagtacgccccctattgacgtca

atgacggtaaatggcccgcctggcattatgcccagtacatgaccttatg

ggactttcctacttggcagtacatctacgtattagtcatcgctattacc

atgctgatgcggttttggcagtacatcaatgggcgtggatagcggtttg

actcacggggatttccaagtctccaccccattgacgtcaatgggagttt

gttttggcaccaaaatcaacgggactttccaaaatgtcgtaacaactcc

gccccattgacgcaaatgggcggtaggcgtgtacggtgggaggtctata

taagcagagctggtttagtgaaccgtcagatcagatctagagatcccgg

gaccgccaccatgagccccgcggggcccaaggtcccctggttcccaaga

aaagtgtcagagctggacaagtgtcatcacctggtcaccaagttcgacc

ctgacctggacttggaccacccgggcttctcggaccaggtgtaccgcca

gcgcaggaagctgattgctgagatcgccttccagtacaggcacggcgac

ccgattccccgtgtggagtacaccgccgaggagattgccacctggaagg

aggtctacaccacgctgaagggcctctacgccacgcacgcctgcgggga

gcacctggaggcctttgctttgctggagcgcttcagcggctaccgggaa

gacaatatcccccagctggaggacgtctcccgcttcctgaaggagcgca
```

-continued

```
cgggcttccagctgcggcctgtggccggcctgctgtccgcccgggactt

cctggccagcctggccttccgcgtgttccagtgcacccagtatatccgc

cacgcgtcctcgcccatgcactcccctgagccggactgctgccacgagc

tgctggggcacgtgcccatgctggccgaccgcaccttcgcgcagttctc

gcaggacattggcctggcgtccctgggggcctcggatgaggaaattgag

aagctgtccacgctgtactggttcacggtggagttcgggctgtgtaagc

agaacggggaggtgaaggcctatggtgccgggctgctgtcctcctacgg

ggagctcctgcactgcctgtctgaggagcctgagattcgggccttcgac

cctgaggctgcggccgtgcagccctaccaagaccagacgtaccagtcag

tctacttcgtgtctgagagcttcagtgacgccaaggacaagctcaggag

ctatgcctcacgcatccagcgccccttctccgtgaagttcgacccgtac

acgctggccatcgacgtgctggacagcccccaggccgtgcggcgctccc

tggagggtgtccaggatgagctggacacccttgcccatgcgctgagtgc

cattggctaaagcaggtttccccaactgacacaaaacgtgcaacttgaa

actccgcctggtctttccaggtctagaggggtaacactttgtactgcgt

ttggctccacgctcgatccactggcgagtgttagtaacagcactgttgc

ttcgtagcggagcatgacggccgtgggaactcctccttggtaacaagga

cccacggggccaaaagccacgcccacacgggcccgtcatgtgtgcaacc

ccagcacggcgactttactgcgaaacccactttaaagtgacattgaaac

tggtacccacacactggtgacaggctaaggatgcccttcaggtaccccg

aggtaacacgcgacactcgggatctgagaaggggactggggcttctata

aaagcgctcggtttaaaaagcttctatgcctgaataggtgaccggaggt

cggcacctttcctttgcaattactgaccacgccaccatggagaagccgc

ggggagtcaggtgcaccaatgggttctccgagcgggagctgccgcggcc

cggggccagcccgcctgccgagaagtcccggccgcccgaggccaagggc

gcacagccggccgacgcctggaaggcagggcggcaccgcagcgaggagg

aaaaccaggtgaacctccccaaactggcggctgcttactcgtccattct

gctctcgctgggcgaggacccccagcggcaggggctgctcaagacgccc

tggagggcggccaccgccatgcagtacttcaccaagggataccaggaga

ccatctcagatgtcctgaatgatgctatatttgatgaagatcatgacga

gatggtgattgtgaaggacatagatatgttctccatgtgtgagcatcac

cttgttccatttgtaggaagggtccatattggctatcttcctaacaagc

aagtccttggtctcagtaaacttgccaggattgtagaaatctacagtag

acgactacaagttcaagagcgcctcaccaaacagattgcggtggccatc

acagaagccttgcagcctgctggcgttggagtagtgattgaagcgacac

acatgtgcatggtaatgcgaggcgtgcagaaaatgaacagcaagactgt

cactagcaccatgctgggcgtgttccgggaagaccccaagactcgggag

gagttcctcacactaatcaggagctgaggccacctaatcaacctctgga

ttacaaaatttgtgaaagattgactggtattcttaactatgttgctcct

tttacgctatgtggatacgctgctttaatgcctttgtatcatgctattg

cttcccgtatggctttcattttctcctccttgtataaatcctggttgct
```

-continued

```
gtctctttatgaggagttgtggcccgttgtcaggcaacgtggcgtggtg

tgcactgtgtttgctgacgcaacccccactggttggggcattgccacca

cctgtcagctcctttccgggactttcgctttccccctccctattgccac

ggcggaactcatcgccgcctgccttgcccgctgctggacaggggctcgg

ctgttgggcactgacaattccgtggtgttgtcggggaaatcatcgtcct

ttcccatatgcagctcacagacatgataagatacattgatgagtttgga

caaaccacaactagaatgcagtgaaaaaaatgctttatttgtgaaattt

gtgatgctattgctttatttgtaaccattataagctgcaataaacaagt

taacaacaacaattgcattcattttatgtttcaggttcagggggaggtg

tgggaggttttttaaagcaagtaaaacctctacaaatgtggtattggcc

catctctatcggtatcgtagcataaccccttggggcctctaaacgggtc

ttgaggggttttttgtgcccctcgggccggattgctatctaccggcatt

ggcgcagaaaaaaatgcctgatgcgacgctgcgcgtcttatactcccac

atatgccagattcagcaacggatacggcttccccaacttgcccacttcc

atacgtgtcctccttaccagaaatttatccttaaggtcgtcagctatcc

tgcaggcgatctctcgatttcgatcaagacattcctttaatggtctttt

ctggacaccactaggggtcagaagtagttcatcaaactttcttccctcc

ctaatctcattggttaccttgggctatcgaaacttaattaaccagtcaa

gtcagctacttggcgagatcgacttgtctgggtttcgactacgctcaga

attgcgtcagtcaagttcgatctggtccttgctattgcacccgttctcc

gattacgagtttcatttaaatcatgtgagcaaaaggccagcaaaaggcc

aggaaccgtaaaaaggccgcgttgctggcgtttttccataggctccgcc

cccctgacgagcatcacaaaaatcgacgctcaagtcagaggtggcgaaa

cccgacaggactataaagataccaggcgtttccccctggaagctccctc

gtgcgctctcctgttccgaccctgccgcttaccggatacctgtccgcct

ttctcccttcgggaagcgtggcgctttctcatagctcacgctgtaggta

tctcagttcggtgtaggtcgttcgctccaagctgggctgtgtgcacgaa

ccccccgttcagcccgaccgctgcgccttatccggtaactatcgtcttg

agtccaacccggtaagacacgacttatcgccactggcagcagccactgg

taacaggattagcagagcgaggtatgtaggcggtgctacagagttcttg

aagtggtggcctaactacggctacactagaagaacagtatttggtatct

gcgctctgctgaagccagttaccttcggaaaaagagttggtagctcttg

atccggcaaacaaaccaccgctggtagcggtggtttttttgtttgcaag

cagcagattacgcgcagaaaaaaaggatctcaagaagatcctttgatct

tttctacggggtctgacgctcagtggaacgaaaactcacgttaagggat

tttggtcatgagattatcaaaaaggatcttcacctagatccttttaaat

taaaaatgaagttttaaatcaatctaaagtatatatgagtaaacttggt

ctgacagttaccaatgcttaatcagtgaggcacctatctcagcgatctg

tctatttcgttcatccatagttgcatttaaatttccgaactctccaagg

ccctcgtcggaaaatcttcaaacctttcgtccgatccatcttgcaggct
```

-continued

```
acctctcgaacgaactatcgcaagtctcttggccggccttgcgccttgg

ctattgcttggcagcgcctatcgccaggtattactccaatcccgaatat

ccgagatcgggatcacccgagagaagttcaacctacatcctcaatcccg

atctatccgagatccgaggaatatcgaaatcggggcgcgcctggtgtac

cgagaacgatcctctcagtgcgagtctcgacgatccatatcgttgcttg

gcagtcagccagtcggaatccagcttgggacccaggaagtccaatcgtc

agatattgtactcaagcctggtcacggcagcgtaccgatctgtttaaac

ctagatattgatagtctgatcggtcaacgtataatcgagtcctagcttt

tgcaaacatctatcaagagacaggatcagcaggaggctttcgcatgagt

attcaacatttccgtgtcgcccttattcccttttttgcggcattttgcc

ttcctgtttttgctcacccagaaacgctggtgaaagtaaaagatgctga

agatcagttgggtgcgcgagtgggttacatcgaactggatctcaacagc

ggtaagatccttgagagttttcgccccgaagaacgctttccaatgatga

gcacttttaaagttctgctatgtggcgcggtattatcccgtattgacgc

cgggcaagagcaactcggtcgccgcatacactattctcagaatgacttg

gttgagtattcaccagtcacagaaaagcatcttacggatggcatgacag

taagagaattatgcagtgctgccataaccatgagtgataacactgcggc

caacttacttctgacaacgattggaggaccgaaggagctaaccgctttt

ttgcacaacatgggggatcatgtaactcgccttgatcgttgggaaccgg

agctgaatgaagccataccaaacgacgagcgtgacaccacgatgcctgt

agcaatggcaacaaccttgcgtaaactattaactggcgaactacttact

ctagcttcccggcaacagttgatagactggatggaggcggataaagttg

caggaccacttctgcgctcggcccttccggctggctggtttattgctga

taaatctggagccggtgagcgtgggtctcgcggtatcattgcagcactg

gggccagatggtaagccctcccgtatcgtagttatctacacgacgggga

gtcaggcaactatggatgaacgaaatagacagatcgctgagataggtgc

ctcactgattaagcattggtaaccgattctaggtgcattggcgcagaaa

aaaatgcctgatgcgacgctgcgcgtcttatactcccacatatgccaga

ttcagcaacggatacggcttccccaacttgcccacttccatacgtgtcc

tccttaccagaaatttatccttagatcccgaatcgtttaaactcgact

ctggctctatcgaatctccgtcgtttcgagcttacgcgaacagccgtgg

cgctcatttgctcgtcgggcatcgaatctcgtcagctatcgtcagctta

ccttttggca
```

Preferably, the genetic construct comprises a nucleic acid sequence substantially as set out in SEQ ID No: 18, or a fragment or variant thereof.

One embodiment of the genetic construct is shown in FIG. 11, and is referred to herein as SEQ ID No: 19. This particular embodiment includes a CMV promoter and murine GCH1; these features would be easily replaceable by the skilled person for other variants as disclosed herein. The murine form of GCH1 is to facilitate preclinical testing of the construct. The murine form of GCH1 could be easily replaced by a skilled person, for instance the murine form could be replaced by the human form of GCH1.

[SEQ ID NO: 19]

ggcgatcgcggctcccgacatcttggaccattagctccacaggtatctt
cttccctctagtggtcataacagcagcttcagctacctctcaattcaaa
aaacccctcaagacccgtttagaggccccaaggggttatgctatcaatc
gttgcgttacacacacaaaaaaccaacacacatccatcttcgatggata
gcgattttattatctaactgctgatcgagtgtagccagatctagtaatc
aattacggggtcattagttcatagcccatatatggagttccgcgttaca
taacttacggtaaatggcccgcctggctgaccgcccaacgacccccgcc
cattgacgtcaataatgacgtatgttcccatagtaacgccaatagggac
tttccattgacgtcaatgggtggagtatttacggtaaactgcccacttg
gcagtacatcaagtgtatcatatgccaagtacgccccctattgacgtca
atgacggtaaatggcccgcctggcattatgcccagtacatgaccttatg
ggactttcctacttggcagtacatctacgtattagtcatcgctattacc
atgctgatgcggttttggcagtacatcaatgggcgtggatagcggtttg
actcacggggatttccaagtctccaccccattgacgtcaatgggagttt
gttttggcaccaaaatcaacgggactttccaaaatgtcgtaacaactcc
gccccattgacgcaaatgggcggtaggcgtgtacggtgggaggtctata
taagcagagctggtttagtgaaccgtcagatcagatctagagatcccgg
gaccgccaccatgagccccgcggggcccaaggtcccctggttcccaaga
aaagtgtcagagctggacaagtgtcatcacctggtcaccaagttcgacc
ctgacctggacttggaccacccgggcttctcggaccaggtgtaccgcca
gcgcaggaagctgattgctgagatcgccttccagtacaggcacggcgac
ccgattccccgtgtggagtacaccgccgaggagattgccacctggaagg
aggtctacaccacgctgaagggcctctacgccacgcacgcctgcgggga
gcacctggaggcctttgctttgctggagcgcttcagcggctaccgggaa
gacaatatcccccagctggaggacgtctcccgcttcctgaaggagcgca
cgggcttccagctgcggcctgtggccggcctgctgtccgcccgggactt
cctggccagcctggccttccgcgtgttccagtgcacccagtatatccgc
cacgcgtcctcgcccatgcactcccctgagccggactgctgccacgagc
tgctggggcacgtgcccatgctggccgaccgcaccttcgcgcagttctc
gcaggacattggcctggcgtccctgggggcctcggatgaggaaattgag
aagctgtccacgctgtactggttcacggtggagttcgggctgtgtaagc
agaacggggaggtgaaggcctatggtgccgggctgctgtcctcctacgg
ggagctcctgcactgcctgtctgaggagcctgagattcgggccttcgac
cctgaggctgcggccgtgcagccctaccaagaccagacgtaccagtcag
tctacttcgtgtctgagagcttcagtgacgccaaggacaagctcaggag
ctatgcctcacgcatccagcgccccttctccgtgaagttcgacccgtac
acgctggccatcgacgtgctggacagcccccaggccgtgcggcgctccc
tggagggtgtccaggatgagctggacacccttgcccatgcgctgagtgc
cattggctaacgcgcgaaacgcgcgccggtgaaacagaccctgaacttt
gatctgctgaaactggcgggcgatgtggaaagcaacccgggcccgatgg -continued agaagccgcggggagtcaggtgcaccaatgggttctccgagcgggagct
gccgcggcccggggccagcccgcctgccgagaagtcccggccgcccgag
gccaagggcgcacagccggccgacgcctggaaggcagggcggcaccgca
gcgaggaggaaaaccaggtgaacctccccaaactggcggctgcttactc
gtccattctgctctcgctgggcgaggacccccagcggcaggggctgctc
aagacgccctggagggcggccaccgccatgcagtacttcaccaagggat
accaggagaccatctcagatgtcctgaatgatgctatatttgatgaaga
tcatgacgagatggtgattgtgaaggacatagatatgttctccatgtgt
gagcatcaccttgttccatttgtaggaagggtccatattggctatcttc
ctaacaagcaagtccttggtctcagtaaacttgccaggattgtagaaat
ctacagtagacgactacaagttcaagagcgcctcaccaaacagattgcg
gtggccatcacagaagccttgcagcctgctggcgttggagtagtgattg
aagcgacacacatgtgcatggtaatgcgaggcgtgcagaaaatgaacag
caagactgtcactagcaccatgctgggcgtgttccgggaagaccccaag
actcgggaggagttcctcacactaatcaggagctgaggccacctaatca
acctctggattacaaaatttgtgaaagattgactggtattcttaactat
gttgctccttttacgctatgtggatacgctgctttaatgcctttgtatc
atgctattgcttcccgtatggctttcattttctcctccttgtataaatc
ctggttgctgtctctttatgaggagttgtggcccgttgtcaggcaacgt
ggcgtggtgtgcactgtgtttgctgacgcaacccccactggttggggca
ttgccaccacctgtcagctcctttccgggactttcgctttccccctccc
tattgccacggcggaactcatcgccgcctgccttgcccgctgctggaca
ggggctcggctgttgggcactgacaattccgtggtgttgtcggggaaat
catcgtcctttcccatatgcagctcacagacatgataagatacattgat
gagtttggacaaaccacaactagaatgcagtgaaaaaaatgctttattt
gtgaaatttgtgatgctattgctttatttgtaaccattataagctgcaa
taaacaagttaacaacaacaattgcattcattttatgtttcaggttcag
ggggaggtgtgggaggttttttaaagcaagtaaaacctctacaaatgtg
gtattggcccatctctatcggtatcgtagcataaccccttggggcctct
aaacgggtcttgagggggttttttgtgcccctcgggccggattgctatct
accggcattggcgcagaaaaaaatgcctgatgcgacgctgcgcgtctta
tactcccacatatgccagattcagcaacggatacggcttccccaacttg
cccacttccatacgtgtcctccttaccagaaatttatccttaaggtcgt
cagctatcctgcaggcgatctctcgatttcgatcaagacattcctttaa
tggtcttttctggacaccactaggggtcagaagtagttcatcaaacttt
cttccctccctaatctcattggttaccttgggctatcgaaacttaatta
accagtcaagtcagctacttggcgagatcgacttgtctgggtttcgact
acgctcagaattgcgtcagtcaagttcgatctggtccttgctattgcac
ccgttctccgattacgagtttcatttaaatcatgtgagcaaaaggccag
caaaaggccaggaaccgtaaaaaggccgcgttgctggcgtttttccata
ggctccgcccccctgacgagcatcacaaaaatcgacgctcaagtcagag -continued gtggcgaaacccgacaggactataaagataccaggcgtttccccctgga agctccctcgtgcgctctcctgttccgaccctgccgcttaccggatacc tgtccgcctttctcccttcgggaagcgtggcgctttctcatagctcacg ctgtaggtatctcagttcggtgtaggtcgttcgctccaagctgggctgt gtgcacgaaccccccgttcagcccgaccgctgcgccttatccggtaact atcgtcttgagtccaacccggtaagacacgacttatcgccactggcagc agccactggtaacaggattagcagagcgaggtatgtaggcggtgctaca gagttcttgaagtggtggcctaactacggctacactagaagaacagtat ttggtatctgcgctctgctgaagccagttaccttcggaaaaagagttgg tagctcttgatccggcaaacaaaccaccgctggtagcggtggtttttt gtttgcaagcagcagattacgcgcagaaaaaaaggatctcaagaagatc ctttgatcttttctacggggtctgacgctcagtggaacgaaaactcacg ttaagggattttggtcatgagattatcaaaaaggatcttcacctagatc cttttaaattaaaaatgaagttttaaatcaatctaaagtatatatgagt aaacttggtctgacagttaccaatgcttaatcagtgaggcacctatctc agcgatctgtctatttcgttcatccatagttgcatttaaatttccgaac tctccaaggccctcgtcggaaaatcttcaaacctttcgtccgatccatc ttgcaggctacctctcgaacgaactatcgcaagtctcttggccggcctt gcgccttggctattgcttggcagcgcctatcgccaggtattactccaat cccgaatatccgagatcgggatcacccgagagaagttcaacctacatcc tcaatcccgatctatccgagatccgaggaatatcgaaatcggggcgcgc ctggtgtaccgagaacgatcctctcagtgcgagtctcgacgatccatat cgttgcttggcagtcagccagtcggaatccagcttgggacccaggaagt ccaatcgtcagatattgtactcaagcctggtcacggcagcgtaccgatc tgtttaaacctagatattgatagtctgatcggtcaacgtataatcgagt cctagcttttgcaaacatctatcaagagacaggatcagcaggaggcttt cgcatgagtattcaacatttccgtgtcgcccttattcccttttttgcgg cattttgccttcctgtttttgctcacccagaaacgctggtgaaagtaaa agatgctgaagatcagttgggtgcgcgagtgggttacatcgaactggat ctcaacagcggtaagatccttgagagttttcgccccgaagaacgctttc caatgatgagcacttttaaagttctgctatgtggcgcggtattatcccg tattgacgccgggcaagagcaactcggtcgccgcatacactattctcag aatgacttggttgagtattcaccagtcacagaaaagcatcttacggatg gcatgacagtaagagaattatgcagtgctgccataaccatgagtgataa cactgcggccaacttacttctgacaacgattggaggaccgaaggagcta accgcttttttgcacaacatgggggatcatgtaactcgccttgatcgtt gggaaccggagctgaatgaagccataccaaacgacgagcgtgacaccac gatgcctgtagcaatggcaacaaccttgcgtaaactattaactggcgaa ctacttactctagcttcccggcaacagttgatagactggatggaggcgg ataaagttgcaggaccacttctgcgctcggcccttccggctggctggtt -continued tattgctgataaatctggagccggtgagcgtgggtctcgcggtatcatt gcagcactggggccagatggtaagccctcccgtatcgtagttatctaca cgacggggagtcaggcaactatggatgaacgaaatagacagatcgctga gataggtgcctcactgattaagcattggtaaccgattctaggtgcattg gcgcagaaaaaaatgcctgatgcgacgctgcgcgtcttatactcccaca tatgccagattcagcaacggatacggcttccccaacttgcccacttcca tacgtgtcctccttaccagaaatttatccttaagatcccgaatcgttta aactcgactctggctctatcgaatctccgtcgtttcgagcttacgcgaa cagccgtggcgctcatttgctcgtcgggcatcgaatctcgtcagctatc gtcagcttaccttttggca Preferably, the genetic construct comprises a nucleic acid sequence substantially as set out in SEQ ID No: 19, or a fragment or variant thereof.

One embodiment of the genetic construct is shown in FIG. 12, and is referred to herein as SEQ ID No: 20. This particular embodiment includes a CMV promoter and murine GCH1; these features would be easily replaceable by the skilled person for other variants as disclosed herein. The murine form of GCH1 is to facilitate preclinical testing of the construct. The murine form of GCH1 could be easily replaced by a skilled person, for instance the murine form could be replaced by the human form of GCH1.

[SEQ ID NO: 20]

ggcgatcgcggctcccgacatcttggaccattagctccacaggtatctt cttccctctagtggtcataacagcagcttcagctacctctcaattcaaa aaacccctcaagacccgtttagaggccccaaggggttatgctatcaatc gttgcgttacacacacaaaaaaccaacacacatccatcttcgatggata gcgattttattatctaactgctgatcgagtgtagccagatctagtaatc aattacggggtcattagttcatagcccatatatggagttccgcgttaca taacttacggtaaatggcccgcctggctgaccgcccaacgacccccgcc cattgacgtcaataatgacgtatgttcccatagtaacgccaatagggac tttccattgacgtcaatgggtggagtatttacggtaaactgcccacttg gcagtacatcaagtgtatcatatgccaagtacgccccctattgacgtca atgacggtaaatggcccgcctggcattatgcccagtacatgaccttatg ggactttcctacttggcagtacatctacgtattagtcatcgctattacc atgctgatgcggttttggcagtacatcaatgggcgtggatagcggtttg actcacggggatttccaagtctccaccccattgacgtcaatgggagttt gttttggcaccaaaatcaacgggactttccaaaatgtcgtaacaactcc gccccattgacgcaaatgggcggtaggcgtgtacggtgggaggtctata taagcagagctggtttagtgaaccgtcagatcagatctagagatcccgg gaccgccaccatgagccccgcggggcccaaggtcccctggttcccaaga aaagtgtcagagctggacaagtgtcatcacctggtcaccaagttcgacc ctgacctggacttggaccacccgggcttctcggaccaggtgtaccgcca gcgcaggaagctgattgctgagatcgccttccagtacaggcacggcgac ccgattccccgtgtggagtacaccgccgaggagattgccacctggaagg -continued

```
aggtctacaccacgctgaagggcctctacgccacgcacgcctgcgggga
gcacctggaggcctttgctttgctggagcgcttcagcggctaccgggaa
gacaatatcccccagctggaggacgtctcccgcttcctgaaggagcgca
cgggcttccagctgcggcctgtggccggcctgctgtccgcccgggactt
cctggccagcctggccttccgcgtgttccagtgcacccagtatatccgc
cacgcgtcctcgcccatgcactcccctgagccggactgctgccacgagc
tgctggggcacgtgcccatgctggccgaccgcaccttcgcgcagttctc
gcaggacattggcctggcgtccctgggggcctcggatgaggaaattgag
aagctgtccacgctgtactggttcacggtggagttcgggctgtgtaagc
agaacggggaggtgaaggcctatggtgccgggctgctgtcctcctacgg
ggagctcctgcactgcctgtctgaggagcctgagattcgggccttcgac
cctgaggctgcggccgtgcagccctaccaagaccagacgtaccagtcag
tctacttcgtgtctgagagcttcagtgacgccaaggacaagctcaggag
ctatgcctcacgcatccagcgccccttctccgtgaagttcgacccgtac
acgctggccatcgacgtgctggacagccccccaggccgtgcggcgctccc
tggagggtgtccaggatgagctggacacccttgcccatgcgctgagtgc
cattggcggaggtggcgggtccgggggcgggggtagcggtggcgggggc
tccgccaccatggagaagggccctgtgcgggcaccggcggagaagccgc
ggggcgccaggtgcagcaatgggttccccgagcgggatccgccgcggcc
cgggcccagcaggccggcggagaagcccccgcggcccgaggccaagagc
gcgcagcccgcggacggctggaagggcgagcggccccgcagcgaggagg
ataacgagctgaacctccctaacctggcagccgcctactcgtccatcct
gagctcgctgggcgagaaccccccagcggcaagggctgctcaagacgccc
tggagggcggcctcggccatgcagttcttcaccaagggctaccaggaga
ccatctcagatgtcctaaacgatgctatatttgatgaagatcatgatga
gatggtgattgtgaaggacatagacatgttttccatgtgtgagcatcac
ttggttccatttgttggaaaggtccatattggttatcttcctaacaagc
aagtccttggcctcagcaaacttgcgaggattgtagaaatctatagtag
aagactacaagttcaggagcgccttacaaaacaaattgctgtagcaatc
acggaagccttgcggcctgctggagtcggggtagtggttgaagcaacac
acatgtgtatggtaatgcgaggtgtacagaaaatgaacagcaaaactgt
gaccagcacaatgttgggtgtgttccgggaggatccaaagactcgggaa
gagttcctgactctcattaggagctgagccacctaatcaacctctggat
tacaaaatttgtgaaagattgactggtattcttaactatgttgctcctt
ttacgctatgtggatacgctgctttaatgcctttgtatcatgctattgc
ttcccgtatggctttcattttctcctccttgtataaatcctggttgctg
tctctttatgaggagttgtggcccgttgtcaggcaacgtggcgtggtgt
gcactgtgtttgctgacgcaacccccactggttggggcattgccaccac
ctgtcagctcctttccgggactttcgctttccccctccctattgccacg
gcggaactcatcgccgcctgccttgcccgctgctggacaggggctcggc
```

-continued

```
tgttgggcactgacaattccgtggtgttgtcggggaaatcatcgtcctt
tcccatatgcagctcacagacatgataagatacattgatgagtttggac
aaaccacaactagaatgcagtgaaaaaaatgctttatttgtgaaatttg
tgatgctattgctttatttgtaaccattataagctgcaataaacaagtt
aacaacaacaattgcattcattttatgtttcaggttcagggggaggtgt
gggaggtttttttaaagcaagtaaaacctctacaaatgtggtattggccc
atctctatcggtatcgtagcataaccccttggggcctctaaacgggtct
tgaggggttttttgtgcccctcgggccggattgctatctaccggcattg
gcgcagaaaaaaatgcctgatgcgacgctgcgcgtcttatactcccaca
tatgccagattcagcaacggatacggcttccccaacttgcccacttcca
tacgtgtcctccttaccagaaatttatccttaaggtcgtcagctatcct
gcaggcgatctctcgatttcgatcaagacattcctttaatggtcttttc
tggacaccactaggggtcagaagtagttcatcaaactttcttccctccc
taatctcattggttaccttgggctatcgaaacttaattaaccagtcaag
tcagctacttggcgagatcgacttgtctgggtttcgactacgctcagaa
ttgcgtcagtcaagttcgatctggtccttgctattgcacccgttctccg
attacgagtttcatttaaatcatgtgagcaaaaggccagcaaaaggcca
ggaaccgtaaaaaggccgcgttgctggcgtttttccataggctccgccc
ccctgacgagcatcacaaaaatcgacgctcaagtcagaggtggcgaaac
ccgacaggactataaagataccaggcgtttccccctggaagctccctcg
tgcgctctcctgttccgaccctgccgcttaccggatacctgtccgcctt
tctcccttcgggaagcgtggcgctttctcatagctcacgctgtaggtat
ctcagttcggtgtaggtcgttcgctccaagctgggctgtgtgcacgaac
cccccgttcagcccgaccgctgcgccttatccggtaactatcgtcttga
gtccaacccggtaagacacgacttatcgccactggcagcagccactggt
aacaggattagcagagcgaggtatgtaggcggtgctacagagttcttga
agtggtggcctaactacggctacactagaagaacagtatttggtatctg
cgctctgctgaagccagttaccttcggaaaaagagttggtagctcttga
tccggcaaacaaaccaccgctggtagcggtggtttttttgtttgcaagc
agcagattacgcgcagaaaaaaaggatctcaagaagatcctttgatctt
ttctacggggtctgacgctcagtggaacgaaaactcacgttaagggatt
ttggtcatgagattatcaaaaaggatcttcacctagatccttttaaatt
aaaaatgaagttttaaatcaatctaaagtatatatgagtaaacttggtc
tgacagttaccaatgcttaatcagtgaggcacctatctcagcgatctgt
ctatttcgttcatccatagttgcatttaaatttccgaactctccaaggc
cctcgtcggaaaatcttcaaacctttcgtccgatccatcttgcaggcta
cctctcgaacgaactatcgcaagtctcttggccggccttgcgccttggc
tattgcttggcagcgcctatcgccaggtattactccaatcccgaatatc
cgagatcgggatcacccgagagaagttcaacctacatcctcaatcccga
tctatccgagatccgaggaatatcgaaatcggggcgcgcctggtgtacc
gagaacgatcctctcagtgcgagtctcgacgatccatatcgttgcttgg
```

-continued

```
cagtcagccagtcggaatccagcttgggacccaggaagtccaatcgtca

gatattgtactcaagcctggtcacggcagcgtaccgatctgtttaaacc

tagatattgatagtctgatcggtcaacgtataatcgagtcctagctttt

gcaaacatctatcaagagacaggatcagcaggaggctttcgcatgagta

ttcaacatttccgtgtcgcccttattcccttttttgcggcattttgcct

tcctgtttttgctcacccagaaacgctggtgaaagtaaaagatgctgaa

gatcagttgggtgcgcgagtgggttacatcgaactggatctcaacagcg

gtaagatccttgagagttttcgccccgaagaacgctttccaatgatgag

cacttttaaagttctgctatgtggcgcggtattatcccgtattgacgcc

gggcaagagcaactcggtcgccgcatacactattctcagaatgacttgg

ttgagtattcaccagtcacagaaaagcatcttacggatggcatgacagt

aagagaattatgcagtgctgccataaccatgagtgataacactgcggcc

aacttacttctgacaacgattggaggaccgaaggagctaaccgcttttt

tgcacaacatgggggatcatgtaactcgccttgatcgttgggaaccgga

gctgaatgaagccataccaaacgacgagcgtgacaccacgatgcctgta

gcaatggcaacaaccttgcgtaaactattaactggcgaactacttactc

tagcttcccggcaacagttgatagactggatggaggcggataaagttgc

aggaccacttctgcgctcggcccttccggctggctggtttattgctgat

aaatctggagccggtgagcgtgggtctcgcggtatcattgcagcactgg

ggccagatggtaagccctcccgtatcgtagttatctacacgacggggag

tcaggcaactatggatgaacgaaatagacagatcgctgagataggtgcc

tcactgattaagcattggtaaccgattctaggtgcattggcgcagaaaa

aaatgcctgatgcgacgctgcgcgtcttatactcccacatatgccagat

tcagcaacggatacggcttccccaacttgcccacttccatacgtgtcct

ccttaccagaaatttatccttaagatcccgaatcgtttaaactcgactc

tggctctatcgaatctccgtcgtttcgagcttacgcgaacagccgtggc

gctcatttgctcgtcgggcatcgaatctcgtcagctatcgtcagcttac

ctttttggca
```

Preferably, the genetic construct comprises a nucleic acid sequence substantially as set out in SEQ ID No: 20, or a fragment or variant thereof.

The inventors have created a series of recombinant expression vectors comprising the construct of the invention.

Thus, according to a second aspect, there is provided a recombinant vector comprising the genetic construct according to the first aspect.

The recombinant vector may be a recombinant AAV (rAAV) vector. The rAAV may be a naturally occurring vector or a vector with a hybrid AAV serotype. The rAAV may be AAV-1, AAV-2, AAV-3A, AAV-3B, AAV-4, AAV-5, AAV-6, AAV-7, AAV-8, AAV-9, AAV-10, and AAV-ii. Preferably, the rAAV has tropism to neural tissue. In a preferred embodiment, the rAAV may be AAV1, AAV9, and more preferably AAV5.

The term "recombinant AAV (rAAV) vector" as used herein can mean a recombinant AAV-derived nucleic acid containing at least one terminal repeat sequence.

In an embodiment, the vector may be an AAV1 vector, comprising a human synapsin 1 promoter, a sequence encoding human truncated TH, an IRES, a sequence encoding human GCH1, a sequence encoding WPRE, a sequence encoding a poly A tail. The following sequence, referred to herein as SEQ ID NO: 13, depicts such a vector. This particular embodiment includes a CMV promoter, a CMV enhancer, an EMCV IRES, and a SV40 poly A tail. The individual features would be easily replaceable by the skilled person for alternatives as disclosed herein.

A map showing the features of a plasmid comprising SEQ ID NO: 13 is shown in FIG. 3.

[SEQ ID NO: 13]

```
CCTGCAGGCAGCTGCGCGCTCGCTCGCTCACTGAGGCCGCCCGGGCGTC

GGGCGACCTTTGGTCGCCCGGCCTCAGTGAGCGAGCGAGCGCGCAGAGA

GGGAGTGGCCAACTCCATCACTAGGGGTTCCTGCGGCCGGTCGCGTACT

AGTAATCAATTACGGGGTCATTAGTTCATAGCCCATATATGGAGTTCCG

CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGCTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTGGTTTAGTGAACCGTCAGATCAGATCTTTGT

CGATCCTACCATCCACTCGACACACCCGCCAGCGGCCGCTGCCAAGCTT

CCGAGCTCTCGAATTCAAAGGAGGTACCCACCATGGCCACCATGAGCCC

CGCGGGGCCCAAGGTCCCCTGGTTCCCAAGAAAAGTGTCAGAGCTGGAC

AAGTGTCATCACCTGGTCACCAAGTTCGACCCTGACCTGGACTTGGACC

ACCCGGGCTTCTCGGACCAGGTGTACCGCCAGCGCAGGAAGCTGATTGC

TGAGATCGCCTTCCAGTACAGGCACGGCGACCCGATTCCCCGTGTGGAG

TACACCGCCGAGGAGATTGCCACCTGGAAGGAGGTCTACACCACGCTGA

AGGGCCTCTACGCCACGCACGCCTGCGGGGAGCACCTGGAGGCCTTTGC

TTTGCTGGAGCGCTTCAGCGGCTACCGGGAAGACAATATCCCCCAGCTG

GAGGACGTCTCCCGCTTCCTGAAGGAGCGCACGGGCTTCCAGCTGCGGC

CTGTGGCCGGCCTGCTGTCCGCCCGGGACTTCCTGGCCAGCCTGGCCTT

CCGCGTGTTCCAGTGCACCCAGTATATCCGCCACGCGTCCTCGCCCATG

CACTCCCCTGAGCCGGACTGCTGCCACGAGCTGCTGGGGCACGTGCCCA

TGCTGGCCGACCGCACCTTCGCGCAGTTCTCGCAGGACATTGGCCTGGC

GTCCCTGGGGGCCTCGGATGAGGAAATTGAGAAGCTGTCCACGCTGTAC

TGGTTCACGGTGGAGTTCGGGCTGTGTAAGCAGAACGGGGAGGTGAAGG

CCTATGGTGCCGGGCTGCTGTCCTCCTACGGGGAGCTCCTGCACTGCCT
```

-continued

```
GTCTGAGGAGCCTGAGATTCGGGCCTTCGACCCTGAGGCTGCGGCCGTG
CAGCCCTACCAAGACCAGACGTACCAGTCAGTCTACTTCGTGTCTGAGA
GCTTCAGTGACGCCAAGGACAAGCTCAGGAGCTATGCCTCACGCATCCA
GCGCCCCTTCTCCGTGAAGTTCGACCCGTACACGCTGGCCATCGACGTG
CTGGACAGCCCCCAGGCCGTGCGGCGCTCCCTGGAGGGTGTCCAGGATG
AGCTGGACACCCTTGCCCATGCGCTGAGTGCCATTGGCTAAACGTTACT
GGCCGAAGCCGCTTGGAATAAGGCCGGTGTGCGTTTGTCTATATGTTAT
TTTCCACCATATTGCCGTCTTTTGGCAATGTGAGGGCCCGGAAACCTGG
CCCTGTCTTCTTGACGAGCATTCCTAGGGGTCTTTCCCCTCTCGCCAAA
GGAATGCAAGGTCTGTTGAATGTCGTGAAGGAAGCAGTTCCTCTGGAAG
CTTCTTGAAGACAAACAACGTCTGTAGCGACCCTTTGCAGGCAGCGGAA
CCCCCCACCTGGCGACAGGTGCCTCTGCGGCCAAAAGCCACGTGTATAA
GATACACCTGCAAAGGCGGCACAACCCCAGTGCCACGTTGTGAGTTGGA
TAGTTGTGGAAAGAGTCAAATGGCTCCCCTCAAGCGTATTCAACAAGGG
GCTGAAGGATGCCCAGAAGGTACCCCATTGTATGGGATCTGATCTGGGG
CCTCGGTGCACATGCTTTTCATGTGTTTAGTCGAGGTTAAAAAACGTCT
AGGCCCCCCGAACCACGGGGACGTGGTTTTCCTTTGAAAAACACGATGA
TAATAGCCACCATGGAGAAGGGCCCTGTGCGGGCACCGGCGGAGAAGCC
GCGGGGCGCCAGGTGCAGCAATGGGTTCCCCGAGCGGGATCCGCCGCGG
CCCGGGCCCAGCAGGCCGGCGGAGAAGCCCCCGCGGCCCGAGGCCAAGA
GCGCGCAGCCCGCGGACGGCTGGAAGGGCGAGCGGCCCCGCAGCGAGGA
GGATAACGAGCTGAACCTCCCTAACCTGGCAGCCGCCTACTCGTCCATC
CTGAGCTCGCTGGGCGAGAACCCCCAGCGGCAAGGGCTGCTCAAGACGC
CCTGGAGGGCGGCCTCGGCCATGCAGTTCTTCACCAAGGGCTACCAGGA
GACCATCTCAGATGTCCTAAACGATGCTATATTTGATGAAGATCATGAT
GAGATGGTGATTGTGAAGGACATAGACATGTTTTCCATGTGTGAGCATC
ACTTGGTTCCATTTGTTGGAAAGGTCCATATTGGTTATCTTCCTAACAA
GCAAGTCCTTGGCCTCAGCAAACTTGCGAGGATTGTAGAAATCTATAGT
AGAAGACTACAAGTTCAGGAGCGCCTTACAAAACAAATTGCTGTAGCAA
TCACGGAAGCCTTGCGGCCTGCTGGAGTCGGGGTAGTGGTTGAAGCAAC
ACACATGTGTATGGTAATGCGAGGTGTACAGAAAATGAACAGCAAAACT
GTGACCAGCACAATGTTGGGTGTGTTCCGGGAGGATCCAAAGACTCGGG
AAGAGTTCCTGACTCTCATTAGGAGCTGAGCCACCTAATCAACCTCTGG
ATTACAAAATTTGTGAAAGATTGACTGGTATTCTTAACTATGTTGCTCC
TTTTACGCTATGTGGATACGCTGCTTTAATGCCTTTGTATCATGCTATT
GCTTCCCGTATGGCTTTCATTTTCTCCTCCTTGTATAAATCCTGGTTGC
TGTCTCTTTATGAGGAGTTGTGGCCCGTTGTCAGGCAACGTGGCGTGGT
GTGCACTGTGTTTGCTGACGCAACCCCCACTGGTTGGGGCATTGCCACC
ACCTGTCAGCTCCTTTCCGGGACTTTCGCTTTCCCCCTCCCTATTGCCA
CGGCGGAACTCATCGCCGCCTGCCTTGCCCGCTGCTGGACAGGGGCTCG
GCTGTTGGGCACTGACAATTCCGTGGTGTTGTCGGGGAAATCATCGTCC
```

-continued

```
TTTCCCTGGCTGACTGATACAATCGATTTCTGGATCCGCAGGCCTCTGC
TAGCTTGACTGACTGAGATACAGCGTACCTTCAGCTCACAGACATGATA
AGATACATTGATGAGTTTGGACAAACCACAACTAGAATGCAGTGAAAAA
AATGCTTTATTTGTGAAATTTGTGATGCTATTGCTTTATTTGTAACCAT
TATAAGCTGCAATAAACAAGTTAACAACAACAATTGCATTCATTTTATG
TTTCAGGTTCAGGGGGAGGTGTGGGAGGTTTTTTAAGCTTAACGCGGTA
ACCACGTGCGGACCCAACGGCCGCAGGAACCCCTAGTGATGGAGTTGGC
CACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAG
CGCGCAGCTGCCTGCAGGGGCGCCTGATGCGGTATTTTCTCCTTACGCA
TCTGTGCGGTATTTCACACCGCATACGTCAAAGCAACCATAGTACGCGC
CCTGTAGCGGCGCATTAAGCGCGGCGGGTGTGGTGGTTACGCGCAGCGT
GACCGCTACACTTGCCAGCGCCCTAGCGCCCGCTCCTTTCGCTTTCTTC
CCTTCCTTTCTCGCCACGTTCGCCGGCTTTCCCCGTCAAGCTCTAAATC
GGGGGCTCCCTTTAGGGTTCCGATTTAGTGCTTTACGGCACCTCGACCC
CAAAAAACTTGATTTGGGTGATGGTTCACGTAGTGGGCCATCGCCCTGA
TAGACGGTTTTTCGCCCTTTGACGTTGGAGTCCACGTTCTTTAATAGTG
GACTCTTGTTCCAAACTGGAACAACACTCAACCCTATCTCGGGCTATTC
TTTTGATTTATAAGGGATTTTGCCGATTTCGGCCTATTGGTTAAAAAAT
GAGCTGATTTAACAAAAATTTAACGCGAATTTTAACAAAATATTAACGT
TTACAATTTTATGGTGCACTCTCAGTACAATCTGCTCTGATGCCGCATA
GTTAAGCCAGCCCCGACACCCGCCAACACCCGCTGACGCGCCCTGACGG
GCTTGTCTGCTCCCGGCATCCGCTTACAGACAAGCTGTGACCGTCTCCG
GGAGCTGCATGTGTCAGAGGTTTTCACCGTCATCACCGAAACGCGCGAG
ACGAAAGGGCCTCGTGATACGCCTATTTTTATAGGTTAATGTCATGATA
ATAATGGTTTCTTAGACGTCAGGTGGCACTTTTCGGGGAAATGTGCGCG
GAACCCCTATTTGTTTATTTTTCTAAATACATTCAAATATGTATCCGCT
CATGAGACAATAACCCTGATAAATGCTTCAATAATATTGAAAAAGGAAG
AGTATGAGTATTCAACATTTCCGTGTCGCCCTTATTCCCTTTTTTGCGG
CATTTTGCCTTCCTGTTTTTGCTCACCCAGAAACGCTGGTGAAAGTAAA
AGATGCTGAAGATCAGTTGGGTGCACGAGTGGGTTACATCGAACTGGAT
CTCAACAGCGGTAAGATCCTTGAGAGTTTTCGCCCCGAAGAACGTTTTC
CAATGATGAGCACTTTTAAAGTTCTGCTATGTGGCGCGGTATTATCCCG
TATTGACGCCGGGCAAGAGCAACTCGGTCGCCGCATACACTATTCTCAG
AATGACTTGGTTGAGTACTCACCAGTCACAGAAAAGCATCTTACGGATG
GCATGACAGTAAGAGAATTATGCAGTGCTGCCATAACCATGAGTGATAA
CACTGCGGCCAACTTACTTCTGACAACGATCGGAGGACCGAAGGAGCTA
ACCGCTTTTTTGCACAACATGGGGGATCATGTAACTCGCCTTGATCGTT
GGGAACCGGAGCTGAATGAAGCCATACCAAACGACGAGCGTGACACCAC
GATGCCTGTAGCAATGGCAACAACGTTGCGCAAACTATTAACTGGCGAA
```

-continued

```
CTACTTACTCTAGCTTCCCGGCAACAATTAATAGACTGGATGGAGGCGG
ATAAAGTTGCAGGACCACTTCTGCGCTCGGCCCTTCCGGCTGGCTGGTT
TATTGCTGATAAATCTGGAGCCGGTGAGCGTGGGTCTCGCGGTATCATT
GCAGCACTGGGGCCAGATGGTAAGCCCTCCCGTATCGTAGTTATCTACA
CGACGGGGAGTCAGGCAACTATGGATGAACGAAATAGACAGATCGCTGA
GATAGGTGCCTCACTGATTAAGCATTGGTAACTGTCAGACCAAGTTTAC
TCATATATACTTTAGATTGATTTAAAACTTCATTTTTAATTTAAAAGGA
TCTAGGTGAAGATCCTTTTTGATAATCTCATGACCAAAATCCCTTAACG
TGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAA
AAAAACCACCGCTACCAGCGGTGGTTTGTTTGCCGGATCAAGAGCTACC
AACTCTTTTTCCGAAGGTAACTGGCTTCAGCAGAGCGCAGATACCAAAT
ACTGTCCTTCTAGTGTAGCCGTAGTTAGGCCACCACTTCAAGAACTCTG
TAGCACCGCCTACATACCTCGCTCTGCTAATCCTGTTACCAGTGGCTGC
TGCCAGTGGCGATAAGTCGTGTCTTACCGGGTTGGACTCAAGACGATAG
TTACCGGATAAGGCGCAGCGGTCGGGCTGAACGGGGGGTTCGTGCACAC
AGCCCAGCTTGGAGCGAACGACCTACACCGAACTGAGATACCTACAGCG
TGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTA
TGGAAAAACGCCAGCAACGCGGCCTTTTTACGGTTCCTGGCCTTTTGCT
GGCCTTTTGCTCACATGT
```

Preferably, the vector comprises a nucleic acid sequence substantially as set out in SEQ ID No: 13, or a fragment or variant thereof.

The following sequence, referred to herein as SEQ ID NO: 14, depicts a vector similar to SEQ ID NO: 13, but this particular embodiment includes an FMDV IRES instead of the EMCV IRES. A map showing the features of a plasmid comprising SEQ ID NO: 14 is shown in FIG. 4.

[SEQ ID NO: 14]

```
CCTGCAGGCAGCTGCGCGCTCGCTCGCTCACTGAGGCCGCCCGGGCGTC
GGGCGACCTTTGGTCGCCCGGCCTCAGTGAGCGAGCGAGCGCGCAGAGA
GGGAGTGGCCAACTCCATCACTAGGGGTTCCTGCGGCCGGTCGCGTACT
AGTAATCAATTACGGGGTCATTAGTTCATAGCCCATATATGGAGTTCCG
CGTTACATAACTTACGGTAAATGGCCCGCCTGGCTGACCGCCCAACGAC
CCCCGCCCATTGACGTCAATAATGACGTATGTTCCCATAGTAACGCCAA
TAGGGACTTTCCATTGACGTCAATGGGTGGAGTATTTACGGTAAACTGC
CCACTTGGCAGTACATCAAGTGTATCATATGCCAAGTACGCCCCCTATT
GACGTCAATGACGGTAAATGGCCCGCCTGGCATTATGCCCAGTACATGA
CCTTATGGGACTTTCCTACTTGGCAGTACATCTACGTATTAGTCATCGC
TATTACCATGCTGATGCGGTTTTGGCAGTACATCAATGGGCGTGGATAG
```

-continued

```
CGGTTTGACTCACGGGGATTTCCAAGTCTCCACCCCATTGACGTCAATG
GGAGTTTGTTTTGGCACCAAAATCAACGGGACTTTCCAAAATGTCGTAA
CAACTCCGCCCCATTGACGCAAATGGGCGGTAGGCGTGTACGGTGGGAG
GTCTATATAAGCAGAGCTGGTTTAGTGAACCGTCAGATCAGATCTTTGT
CGATCCTACCATCCACTCGACACACCCGCCAGCGGCCGCTGCCAAGCTT
CCGAGCTCTCGAATTCAAAGGAGGTACCCACCATGGCCACCATGAGCCC
CGCGGGGCCCAAGGTCCCCTGGTTCCCAAGAAAAGTGTCAGAGCTGGAC
AAGTGTCATCACCTGGTCACCAAGTTCGACCCTGACCTGGACTTGGACC
ACCCGGGCTTCTCGGACCAGGTGTACCGCCAGCGCAGGAAGCTGATTGC
TGAGATCGCCTTCCAGTACAGGCACGGCGACCCGATTCCCCGTGTGGAG
TACACCGCCGAGGAGATTGCCACCTGGAAGGAGGTCTACACCACGCTGA
AGGGCCTCTACGCCACGCACGCCTGCGGGGAGCACCTGGAGGCCTTTGC
TTTGCTGGAGCGCTTCAGCGGCTACCGGGAAGACAATATCCCCCAGCTG
GAGGACGTCTCCCGCTTCCTGAAGGAGCGCACGGGCTTCCAGCTGCGGC
CTGTGGCCGGCCTGCTGTCCGCCCGGGACTTCCTGGCCAGCCTGGCCTT
CCGCGTGTTCCAGTGCACCCAGTATATCCGCCACGCGTCCTCGCCCATG
CACTCCCCTGAGCCGGACTGCTGCCACGAGCTGCTGGGGCACGTGCCCA
TGCTGGCCGACCGCACCTTCGCGCAGTTCTCGCAGGACATTGGCCTGGC
GTCCCTGGGGGCCTCGGATGAGGAAATTGAGAAGCTGTCCACGCTGTAC
TGGTTCACGGTGGAGTTCGGGCTGTGTAAGCAGAACGGGGAGGTGAAGG
CCTATGGTGCCGGGCTGCTGTCCTCCTACGGGGAGCTCCTGCACTGCCT
GTCTGAGGAGCCTGAGATTCGGGCCTTCGACCCTGAGGCTGCGGCCGTG
CAGCCCTACCAAGACCAGACGTACCAGTCAGTCTACTTCGTGTCTGAGA
GCTTCAGTGACGCCAAGGACAAGCTCAGGAGCTATGCCTCACGCATCCA
GCGCCCCTTCTCCGTGAAGTTCGACCCGTACACGCTGGCCATCGACGTG
CTGGACAGCCCCCAGGCCGTGCGGCGCTCCCTGGAGGGTGTCCAGGATG
AGCTGGACACCCTTGCCCATGCGCTGAGTGCCATTGGCTAAAGCAGGTT
TCCCCAACTGACACAAAACGTGCAACTTGAAACTCCGCCTGGTCTTTCC
AGGTCTAGAGGGGTAACACTTTGTACTGCGTTTGGCTCCACGCTCGATC
CACTGGCGAGTGTTAGTAACAGCACTGTTGCTTCGTAGCGGAGCATGAC
GGCCGTGGGAACTCCTCCTTGGTAACAAGGACCCACGGGGCCAAAAGCC
ACGCCCACACGGGCCCGTCATGTGTGCAACCCCAGCACGGCGACTTTAC
TGCGAAACCCACTTTAAAGTGACATTGAAACTGGTACCCACACACTGGT
GACAGGCTAAGGATGCCCTTCAGGTACCCCGAGGTAACACGCGACACTC
GGGATCTGAGAAGGGGACTGGGGCTTCTATAAAAGCGCTCGGTTTAAAA
AGCTTCTATGCCTGAATAGGTGACCGGAGGTCGGCACCTTTCCTTTGCA
ATTACTGACCACGCCACCATGGAGAAGGGCCCTGTGCGGGCACCGGCGG
AGAAGCCGCGGGGCGCCAGGTGCAGCAATGGGTTCCCCGAGCGGGATCC
GCCGCGGCCCGGGCCCAGCAGGCCGGCGGAGAAGCCCCCGCGGCCCGAG
GCCAAGAGCGCGCAGCCCGCGGACGGCTGGAAGGGCGAGCGGCCCCGCA
GCGAGGAGGATAACGAGCTGAACCTCCCTAACCTGGCAGCCGCCTACTC
```

-continued

GTCCATCCTGAGCTCGCTGGGCGAGAACCCCCAGCGGCAAGGGCTGCTC
AAGACGCCCTGGAGGGCGGCCTCGGCCATGCAGTTCTTCACCAAGGGCT
ACCAGGAGACCATCTCAGATGTCCTAAACGATGCTATATTTGATGAAGA
TCATGATGAGATGGTGATTGTGAAGGACATAGACATGTTTTCCATGTGT
GAGCATCACTTGGTTCCATTTGTTGGAAAGGTCCATATTGGTTATCTTC
CTAACAAGCAAGTCCTTGGCCTCAGCAAACTTGCGAGGATTGTAGAAAT
CTATAGTAGAAGACTACAAGTTCAGGAGCGCCTTACAAAACAAATTGCT
GTAGCAATCACGGAAGCCTTGCGGCCTGCTGGAGTCGGGGTAGTGGTTG
AAGCAACACACATGTGTATGGTAATGCGAGGTGTACAGAAAATGAACAG
CAAAACTGTGACCAGCACAATGTTGGGTGTGTTCCGGGAGGATCCAAAG
ACTCGGGAAGAGTTCCTGACTCTCATTAGGAGCTGAGCCACCTAATCAA
CCTCTGGATTACAAAATTTGTGAAAGATTGACTGGTATTCTTAACTATG
TTGCTCCTTTTACGCTATGTGGATACGCTGCTTTAATGCCTTTGTATCA
TGCTATTGCTTCCCGTATGGCTTTCATTTTCTCCTCCTTGTATAAATCC
TGGTTGCTGTCTCTTTATGAGGAGTTGTGGCCCGTTGTCAGGCAACGTG
GCGTGGTGTGCACTGTGTTTGCTGACGCAACCCCCACTGGTTGGGGCAT
TGCCACCACCTGTCAGCTCCTTTCCGGGACTTTCGCTTTCCCCCTCCCT
ATTGCCACGGCGGAACTCATCGCCGCCTGCCTTGCCCGCTGCTGGACAG
GGGCTCGGCTGTTGGGCACTGACAATTCCGTGGTGTTGTCGGGGAAATC
ATCGTCCTTTCCCTGGCTGACTGATACAATCGATTTCTGGATCCGCAGG
CCTCTGCTAGCTTGACTGACTGAGATACAGCGTACCTTCAGCTCACAGA
CATGATAAGATACATTGATGAGTTTGGACAAACCACAACTAGAATGCAG
TGAAAAAAATGCTTTATTTGTGAAATTTGTGATGCTATTGCTTTATTTG
TAACCATTATAAGCTGCAATAAACAAGTTAACAACAACAATTGCATTCA
TTTTATGTTTCAGGTTCAGGGGGAGGTGTGGGAGGTTTTTTAAGCTTAA
CGCGGTAACCACGTGCGGACCCAACGGCCGCAGGAACCCCTAGTGATGG
AGTTGGCCACTCCCTCTCTGCGCGCTCGCTCGCTCACTGAGGCCGGGCG
ACCAAAGGTCGCCCGACGCCCGGGCTTTGCCCGGGCGGCCTCAGTGAGC
GAGCGAGCGCGCAGCTGCCTGCAGGGGCGCCTGATGCGGTATTTTCTCC
TTACGCATCTGTGCGGTATTTCACACCGCATACGTCAAAGCAACCATAG
TACGCGCCCTGTAGCGGCGCATTAAGCGCGGCGGGTGTGGTGGTTACGC
GCAGCGTGACCGCTACACTTGCCAGCGCCCTAGCGCCCGCTCCTTTCGC
TTTCTTCCCTTCCTTTCTCGCCACGTTCGCCGGCTTTCCCCGTCAAGCT
CTAAATCGGGGGCTCCCTTTAGGGTTCCGATTTAGTGCTTTACGGCACC
TCGACCCCAAAAAACTTGATTTGGGTGATGGTTCACGTAGTGGGCCATC
GCCCTGATAGACGGTTTTTCGCCCTTTGACGTTGGAGTCCACGTTCTTT
AATAGTGGACTCTTGTTCCAAACTGGAACAACACTCAACCCTATCTCGG
GCTATTCTTTTGATTTATAAGGGATTTTGCCGATTTCGGCCTATTGGTT
AAAAAATGAGCTGATTTAACAAAAATTTAACGCGAATTTTAACAAAATA
TTAACGTTTACAATTTTATGGTGCACTCTCAGTACAATCTGCTCTGATG

-continued

CCGCATAGTTAAGCCAGCCCCGACACCCGCCAACACCCGCTGACGCGCC
CTGACGGGCTTGTCTGCTCCCGGCATCCGCTTACAGACAAGCTGTGACC
GTCTCCGGGAGCTGCATGTGTCAGAGGTTTTCACCGTCATCACCGAAAC
GCGCGAGACGAAAGGGCCTCGTGATACGCCTATTTTTATAGGTTAATGT
CATGATAATAATGGTTTCTTAGACGTCAGGTGGCACTTTTCGGGGAAAT
GTGCGCGGAACCCCTATTTGTTTATTTTTCTAAATACATTCAAATATGT
ATCCGCTCATGAGACAATAACCCTGATAAATGCTTCAATAATATTGAAA
AAGGAAGAGTATGAGTATTCAACATTTCCGTGTCGCCCTTATTCCCTTT
TTTGCGGCATTTTGCCTTCCTGTTTTTGCTCACCCAGAAACGCTGGTGA
AAGTAAAAGATGCTGAAGATCAGTTGGGTGCACGAGTGGGTTACATCGA
ACTGGATCTCAACAGCGGTAAGATCCTTGAGAGTTTTCGCCCCGAAGAA
CGTTTTCCAATGATGAGCACTTTTAAAGTTCTGCTATGTGGCGCGGTAT
TATCCCGTATTGACGCCGGGCAAGAGCAACTCGGTCGCCGCATACACTA
TTCTCAGAATGACTTGGTTGAGTACTCACCAGTCACAGAAAAGCATCTT
ACGGATGGCATGACAGTAAGAGAATTATGCAGTGCTGCCATAACCATGA
GTGATAACACTGCGGCCAACTTACTTCTGACAACGATCGGAGGACCGAA
GGAGCTAACCGCTTTTTTGCACAACATGGGGGATCATGTAACTCGCCTT
GATCGTTGGGAACCGGAGCTGAATGAAGCCATACCAAACGACGAGCGTG
ACACCACGATGCCTGTAGCAATGGCAACAACGTTGCGCAAACTATTAAC
TGGCGAACTACTTACTCTAGCTTCCCGGCAACAATTAATAGACTGGATG
GAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGG
TATCATTGCAGCACTGGGGCCAGATGGTAAGCCCTCCCGTATCGTAGTT
ATCTACACGACGGGGAGTCAGGCAACTATGGATGAACGAAATAGACAGA
TCGCTGAGATAGGTGCCTCACTGATTAAGCATTGGTAACTGTCAGACCA
AGTTTACTCATATATACTTTAGATTGATTTAAAACTTCATTTTTAATTT
AAAAGGATCTAGGTGAAGATCCTTTTTGATAATCTCATGACCAAAATCC
CTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTG
CAAACAAAAAAACCACCGCTACCAGCGGTGGTTTGTTTGCCGGATCAAG
AGCTACCAACTCTTTTTCCGAAGGTAACTGGCTTCAGCAGAGCGCAGAT
ACCAAATACTGTCCTTCTAGTGTAGCCGTAGTTAGGCCACCACTTCAAG
AACTCTGTAGCACCGCCTACATACCTCGCTCTGCTAATCCTGTTACCAG
TGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCG
TGCACACAGCCCAGCTTGGAGCGAACGACCTACACCGAACTGAGATACC
TACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTC
GCCACCTCTGACTTGAGCGTCGATTTTTGTGATGCTCGTCAGGGGGGCG

-continued

GAGCCTATGGAAAAACGCCAGCAACGCGGCCTTTTTACGGTTCCTGGCC

TTTTGCTGGCCTTTTGCTCACATGT

Preferably, the vector comprises a nucleic acid sequence substantially as set out in SEQ ID No: 14, or a fragment or variant thereof.

The following sequence, referred to herein as SEQ ID NO: 15, depicts a vector similar to SEQ ID NO: 13, but this particular embodiment includes a Furin cleavage site and a viral 2A peptide spacer, instead of the EMCV IRES. A map showing the features of a plasmid comprising SEQ ID NO: 15 is shown in FIG. 5.

[SEQ ID NO: 15]

CCTGCAGGCAGCTGCGCGCTCGCTCGCTCACTGAGGCCGCCCGGGCGTC

GGGCGACCTTTGGTCGCCCGGCCTCAGTGAGCGAGCGAGCGCGCAGAGA

GGGAGTGGCCAACTCCATCACTAGGGGTTCCTGCGGCCGGTCGCGTACT

AGTAATCAATTACGGGGTCATTAGTTCATAGCCCATATATGGAGTTCCG

CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGCTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTGGTTTAGTGAACCGTCAGATCAGATCTTTGT

CGATCCTACCATCCACTCGACACACCCGCCAGCGGCCGCTGCCAAGCTT

CCGAGCTCTCGAATTCAAAGGAGGTACCCACCATGGCCACCATGAGCCC

CGCGGGGCCCAAGGTCCCCTGGTTCCCAAGAAAAGTGTCAGAGCTGGAC

AAGTGTCATCACCTGGTCACCAAGTTCGACCCTGACCTGGACTTGGACC

ACCCGGGCTTCTCGGACCAGGTGTACCGCCAGCGCAGGAAGCTGATTGC

TGAGATCGCCTTCCAGTACAGGCACGGCGACCCGATTCCCCGTGTGGAG

TACACCGCCGAGGAGATTGCCACCTGGAAGGAGGTCTACACCACGCTGA

AGGGCCTCTACGCCACGCACGCCTGCGGGGAGCACCTGGAGGCCTTTGC

TTTGCTGGAGCGCTTCAGCGGCTACCGGGAAGACAATATCCCCCAGCTG

GAGGACGTCTCCCGCTTCCTGAAGGAGCGCACGGGCTTCCAGCTGCGGC

CTGTGGCCGGCCTGCTGTCCGCCCGGGACTTCCTGGCCAGCCTGGCCTT

CCGCGTGTTCCAGTGCACCCAGTATATCCGCCACGCGTCCTCGCCCATG

CACTCCCCTGAGCCGGACTGCTGCCACGAGCTGCTGGGGCACGTGCCCA

TGCTGGCCGACCGCACCTTCGCGCAGTTCTCGCAGGACATTGGCCTGGC

GTCCCTGGGGGCCTCGGATGAGGAAATTGAGAAGCTGTCCACGCTGTAC

TGGTTCACGGTGGAGTTCGGGCTGTGTAAGCAGAACGGGGAGGTGAAGG

-continued

CCTATGGTGCCGGGCTGCTGTCCTCCTACGGGGAGCTCCTGCACTGCCT

GTCTGAGGAGCCTGAGATTCGGGCCTTCGACCCTGAGGCTGCGGCCGTG

CAGCCCTACCAAGACCAGACGTACCAGTCAGTCTACTTCGTGTCTGAGA

GCTTCAGTGACGCCAAGGACAAGCTCAGGAGCTATGCCTCACGCATCCA

GCGCCCCTTCTCCGTGAAGTTCGACCCGTACACGCTGGCCATCGACGTG

CTGGACAGCCCCCAGGCCGTGCGGCGCTCCCTGGAGGGTGTCCAGGATG

AGCTGGACACCCTTGCCCATGCGCTGAGTGCCATTGGCTAACGCGCGAA

ACGCGCGCCGGTGAAACAGACCCTGAACTTTGATCTGCTGAAACTGGCG

GGCGATGTGGAAAGCAACCCGGGCCCGGCCACCATGGAGAAGGGCCCTG

TGCGGGCACCGGCGGAGAAGCCGCGGGGCGCCAGGTGCAGCAATGGGTT

CCCCGAGCGGGATCCGCCGCGGCCCGGGCCCAGCAGGCCGGCGGAGAAG

CCCCCGCGGCCCGAGGCCAAGAGCGCGCAGCCCGCGGACGGCTGGAAGG

GCGAGCGGCCCCGCAGCGAGGAGGATAACGAGCTGAACCTCCCTAACCT

GGCAGCCGCCTACTCGTCCATCCTGAGCTCGCTGGGCGAGAACCCCCAG

CGGCAAGGGCTGCTCAAGACGCCCTGGAGGGCGGCCTCGGCCATGCAGT

TCTTCACCAAGGGCTACCAGGAGACCATCTCAGATGTCCTAAACGATGC

TATATTTGATGAAGATCATGATGAGATGGTGATTGTGAAGGACATAGAC

ATGTTTTCCATGTGTGAGCATCACTTGGTTCCATTTGTTGGAAAGGTCC

ATATTGGTTATCTTCCTAACAAGCAAGTCCTTGGCCTCAGCAAACTTGC

GAGGATTGTAGAAATCTATAGTAGAAGACTACAAGTTCAGGAGCGCCTT

ACAAAACAAATTGCTGTAGCAATCACGGAAGCCTTGCGGCCTGCTGGAG

TCGGGGTAGTGGTTGAAGCAACACACATGTGTATGGTAATGCGAGGTGT

ACAGAAAATGAACAGCAAAACTGTGACCAGCACAATGTTGGGTGTGTTC

CGGGAGGATCCAAAGACTCGGGAAGAGTTCCTGACTCTCATTAGGAGCT

GAGCCACCTAATCAACCTCTGGATTACAAAATTTGTGAAAGATTGACTG

GTATTCTTAACTATGTTGCTCCTTTTACGCTATGTGGATACGCTGCTTT

AATGCCTTTGTATCATGCTATTGCTTCCCGTATGGCTTTCATTTTCTCC

TCCTTGTATAAATCCTGGTTGCTGTCTCTTTATGAGGAGTTGTGGCCCG

TTGTCAGGCAACGTGGCGTGGTGTGCACTGTGTTTGCTGACGCAACCCC

CACTGGTTGGGGCATTGCCACCACCTGTCAGCTCCTTTCCGGGACTTTC

GCTTTCCCCCTCCCTATTGCCACGGCGGAACTCATCGCCGCCTGCCTTG

CCCGCTGCTGGACAGGGGCTCGGCTGTTGGGCACTGACAATTCCGTGGT

GTTGTCGGGGAAATCATCGTCCTTTCCCTGGCTGACTGATACAATCGAT

TTCTGGATCCGCAGGCCTCTGCTAGCTTGACTGACTGAGATACAGCGTA

CCTTCAGCTCACAGACATGATAAGATACATTGATGAGTTTGGACAAACC

ACAACTAGAATGCAGTGAAAAAAATGCTTTATTTGTGAAATTTGTGATG

CTATTGCTTTATTTGTAACCATTATAAGCTGCAATAAACAAGTTAACAA

CAACAATTGCATTCATTTTATGTTTCAGGTTCAGGGGGAGGTGTGGGAG

GTTTTTTAAGCTTAACGCGGTAACCACGTGCGGACCCAACGGCCGCAGG

AACCCCTAGTGATGGAGTTGGCCACTCCCTCTCTGCGCGCTCGCTCGCT

CACTGAGGCCGGGCGACCAAAGGTCGCCCGACGCCCGGGCTTTGCCCGG

-continued

GCGGCCTCAGTGAGCGAGCGAGCGCGCAGCTGCCTGCAGGGGCGCCTGA

TGCGGTATTTTCTCCTTACGCATCTGTGCGGTATTTCACACCGCATACG

TCAAAGCAACCATAGTACGCGCCCTGTAGCGGCGCATTAAGCGCGGCGG

GTGTGGTGGTTACGCGCAGCGTGACCGCTACACTTGCCAGCGCCCTAGC

GCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTA

GTGCTTTACGGCACCTCGACCCCAAAAAACTTGATTTGGGTGATGGTTC

ACGTAGTGGGCCATCGCCCTGATAGACGGTTTTTCGCCCTTTGACGTTG

GAGTCCACGTTCTTTAATAGTGGACTCTTGTTCCAAACTGGAACAACAC

TCAACCCTATCTCGGGCTATTCTTTTGATTTATAAGGGATTTTGCCGAT

TTCGGCCTATTGGTTAAAAAATGAGCTGATTTAACAAAAATTTAACGCG

AATTTTAACAAAATATTAACGTTTACAATTTTATGGTGCACTCTCAGTA

CAATCTGCTCTGATGCCGCATAGTTAAGCCAGCCCCGACACCCGCCAAC

ACCCGCTGACGCGCCCTGACGGGCTTGTCTGCTCCCGGCATCCGCTTAC

AGACAAGCTGTGACCGTCTCCGGGAGCTGCATGTGTCAGAGGTTTTCAC

CGTCATCACCGAAACGCGCGAGACGAAAGGGCCTCGTGATACGCCTATT

TTTATAGGTTAATGTCATGATAATAATGGTTTCTTAGACGTCAGGTGGC

ACTTTTCGGGGAAATGTGCGCGGAACCCCTATTTGTTTATTTTTCTAAA

TACATTCAAATATGTATCCGCTCATGAGACAATAACCCTGATAAATGCT

TCAATAATATTGAAAAAGGAAGAGTATGAGTATTCAACATTTCCGTGTC

GCCCTTATTCCCTTTTTTGCGGCATTTTGCCTTCCTGTTTTTGCTCACC

CAGAAACGCTGGTGAAAGTAAAAGATGCTGAAGATCAGTTGGGTGCACG

AGTGGGTTACATCGAACTGGATCTCAACAGCGGTAAGATCCTTGAGAGT

TTTCGCCCCGAAGAACGTTTTCCAATGATGAGCACTTTTAAAGTTCTGC

TATGTGGCGCGGTATTATCCCGTATTGACGCCGGGCAAGAGCAACTCGG

TCGCCGCATACACTATTCTCAGAATGACTTGGTTGAGTACTCACCAGTC

ACAGAAAAGCATCTTACGGATGGCATGACAGTAAGAGAATTATGCAGTG

CTGCCATAACCATGAGTGATAACACTGCGGCCAACTTACTTCTGACAAC

GATCGGAGGACCGAAGGAGCTAACCGCTTTTTTGCACAACATGGGGGAT

CATGTAACTCGCCTTGATCGTTGGGAACCGGAGCTGAATGAAGCCATAC

CAAACGACGAGCGTGACACCACGATGCCTGTAGCAATGGCAACAACGTT

GCGCAAACTATTAACTGGCGAACTACTTACTCTAGCTTCCCGGCAACAA

TTAATAGACTGGATGGAGGCGGATAAAGTTGCAGGACCACTTCTGCGCT

CGGCCCTTCCGGCTGGCTGGTTTATTGCTGATAAATCTGGAGCCGGTGA

GCGTGGGTCTCGCGGTATCATTGCAGCACTGGGGCCAGATGGTAAGCCC

TCCCGTATCGTAGTTATCTACACGACGGGGAGTCAGGCAACTATGGATG

AACGAAATAGACAGATCGCTGAGATAGGTGCCTCACTGATTAAGCATTG

GTAACTGTCAGACCAAGTTTACTCATATATACTTTAGATTGATTTAAAA

CTTCATTTTTAATTTAAAAGGATCTAGGTGAAGATCCTTTTTGATAATC

TCATGACCAAAATCCCTTAACGTGAGTTTTCGTTCCACTGAGCGTCAGA

-continued

CCCCGTAGAAAAGATCAAAGGATCTTCTTGAGATCCTTTTTTTCTGCGC

GTAATCTGCTGCTTGCAAACAAAAAAACCACCGCTACCAGCGGTGGTTT

GTTTGCCGGATCAAGAGCTACCAACTCTTTTTCCGAAGGTAACTGGCTT

CAGCAGAGCGCAGATACCAAATACTGTCCTTCTAGTGTAGCCGTAGTTA

GGCCACCACTTCAAGAACTCTGTAGCACCGCCTACATACCTCGCTCTGC

TAATCCTGTTACCAGTGGCTGCTGCCAGTGGCGATAAGTCGTGTCTTAC

CGGGTTGGACTCAAGACGATAGTTACCGGATAAGGCGCAGCGGTCGGGC

TGAACGGGGGGTTCGTGCACACAGCCCAGCTTGGAGCGAACGACCTACA

CCGAACTGAGATACCTACAGCGTGAGCTATGAGAAAGCGCCACGCTTCC

CGAAGGGAGAAAGGCGGACAGGTATCCGGTAAGCGGCAGGGTCGGAACA

GGAGAGCGCACGAGGGAGCTTCCAGGGGGAAACGCCTGGTATCTTTATA

GTCCTGTCGGGTTTCGCCACCTCTGACTTGAGCGTCGATTTTTGTGATG

CTCGTCAGGGGGGCGGAGCCTATGGAAAAACGCCAGCAACGCGGCCTTT

TTACGGTTCCTGGCCTTTTGCTGGCCTTTTGCTCACATGT

Preferably, the vector comprises a nucleic acid sequence substantially as set out in SEQ ID No: 15, or a fragment or variant thereof.

The following sequence, referred to herein as SEQ ID NO:16, depicts a vector similar to SEQ ID NO: 13, but this particular embodiment includes a flexible linker, instead of the EMCV IRES. A map showing the features of a plasmid comprising SEQ ID NO: 16 is shown in FIG. 6.

[SEQ ID NO: 16]

CCTGCAGGCAGCTGCGCGCTCGCTCGCTCACTGAGGCCGCCCGGGCGTC

GGGCGACCTTTGGTCGCCCGGCCTCAGTGAGCGAGCGAGCGCGCAGAGA

GGGAGTGGCCAACTCCATCACTAGGGGTTCCTGCGGCCGGTCGCGTACT

AGTAATCAATTACGGGGTCATTAGTTCATAGCCCATATATGGAGTTCCG

CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGCTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTGGTTTAGTGAACCGTCAGATCAGATCTTTGT

CGATCCTACCATCCACTCGACACACCCGCCAGCGGCCGCTGCCAAGCTT

CCGAGCTCTCGAATTCAAAGGAGGTACCCACCATGGCCACCATGAGCCC

CGCGGGGCCCAAGGTCCCCTGGTTCCCAAGAAAAGTGTCAGAGCTGGAC

AAGTGTCATCACCTGGTCACCAAGTTCGACCCTGACCTGGACTTGGACC

ACCCGGGCTTCTCGGACCAGGTGTACCGCCAGCGCAGGAAGCTGATTGC

-continued

```
TGAGATCGCCTTCCAGTACAGGCACGGCGACCCGATTCCCCGTGTGGAG
TACACCGCCGAGGAGATTGCCACCTGGAAGGAGGTCTACACCACGCTGA
AGGGCCTCTACGCCACGCACGCCTGCGGGGAGCACCTGGAGGCCTTTGC
TTTGCTGGAGCGCTTCAGCGGCTACCGGGAAGACAATATCCCCCAGCTG
GAGGACGTCTCCCGCTTCCTGAAGGAGCGCACGGGCTTCCAGCTGCGGC
CTGTGGCCGGCCTGCTGTCCGCCCGGGACTTCCTGGCCAGCCTGGCCTT
CCGCGTGTTCCAGTGCACCCAGTATATCCGCCACGCGTCCTCGCCCATG
CACTCCCCTGAGCCGGACTGCTGCCACGAGCTGCTGGGGCACGTGCCCA
TGCTGGCCGACCGCACCTTCGCGCAGTTCTCGCAGGACATTGGCCTGGC
GTCCCTGGGGGCCTCGGATGAGGAAATTGAGAAGCTGTCCACGCTGTAC
TGGTTCACGGTGGAGTTCGGGCTGTGTAAGCAGAACGGGGAGGTGAAGG
CCTATGGTGCCGGGCTGCTGTCCTCCTACGGGGAGCTCCTGCACTGCCT
GTCTGAGGAGCCTGAGATTCGGGCCTTCGACCCTGAGGCTGCGGCCGTG
CAGCCCTACCAAGACCAGACGTACCAGTCAGTCTACTTCGTGTCTGAGA
GCTTCAGTGACGCCAAGGACAAGCTCAGGAGCTATGCCTCACGCATCCA
GCGCCCCTTCTCCGTGAAGTTCGACCCGTACACGCTGGCCATCGACGTG
CTGGACAGCCCCCAGGCCGTGCGGCGCTCCCTGGAGGGTGTCCAGGATG
AGCTGGACACCCTTGCCCATGCGCTGAGTGCCATTGGCTAAGGAGGTGG
CGGGTCCGGGGGCGGGGGTAGCGGTGGCGGGGGCTCCGCCACCATGGAG
AAGGGCCCTGTGCGGGCACCGGCGGAGAAGCCGCGGGGCGCCAGGTGCA
GCAATGGGTTCCCCGAGCGGGATCCGCCGCGGCCCGGGCCCAGCAGGCC
GGCGGAGAAGCCCCCGCGGCCCGAGGCCAAGAGCGCGCAGCCCGCGGAC
GGCTGGAAGGGCGAGCGGCCCCGCAGCGAGGAGGATAACGAGCTGAACC
TCCCTAACCTGGCAGCCGCCTACTCGTCCATCCTGAGCTCGCTGGGCGA
GAACCCCCAGCGGCAAGGGCTGCTCAAGACGCCCTGGAGGGCGGCCTCG
GCCATGCAGTTCTTCACCAAGGGCTACCAGGAGACCATCTCAGATGTCC
TAAACGATGCTATATTTGATGAAGATCATGATGAGATGGTGATTGTGAA
GGACATAGACATGTTTTCCATGTGTGAGCATCACTTGGTTCCATTTGTT
GGAAAGGTCCATATTGGTTATCTTCCTAACAAGCAAGTCCTTGGCCTCA
GCAAACTTGCGAGGATTGTAGAAATCTATAGTAGAAGACTACAAGTTCA
GGAGCGCCTTACAAAACAAATTGCTGTAGCAATCACGGAAGCCTTGCGG
CCTGCTGGAGTCGGGGTAGTGGTTGAAGCAACACACATGTGTATGGTAA
TGCGAGGTGTACAGAAAATGAACAGCAAAACTGTGACCAGCACAATGTT
GGGTGTGTTCCGGGAGGATCCAAAGACTCGGGAAGAGTTCCTGACTCTC
ATTAGGAGCTGAGCCACCTAATCAACCTCTGGATTACAAAATTTGTGAA
AGATTGACTGGTATTCTTAACTATGTTGCTCCTTTTACGCTATGTGGAT
ACGCTGCTTTAATGCCTTTGTATCATGCTATTGCTTCCCGTATGGCTTT
CATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTC
CGGGACTTTCGCTTTCCCCCTCCCTATTGCCACGGCGGAACTCATCGCC
```

-continued

```
GCCTGCCTTGCCCGCTGCTGGACAGGGGCTCGGCTGTTGGGCACTGACA
ATTCCGTGGTGTTGTCGGGGAAATCATCGTCCTTTCCCTGGCTGACTGA
TACAATCGATTTCTGGATCCGCAGGCCTCTGCTAGCTTGACTGACTGAG
ATACAGCGTACCTTCAGCTCACAGACATGATAAGATACATTGATGAGTT
TGGACAAACCACAACTAGAATGCAGTGAAAAAAATGCTTTATTTGTGAA
ATTTGTGATGCTATTGCTTTATTTGTAACCATTATAAGCTGCAATAAAC
AAGTTAACAACAACAATTGCATTCATTTTATGTTTCAGGTTCAGGGGGA
GGTGTGGGAGGTTTTTTAAGCTTAACGCGGTAACCACGTGCGGACCCAA
CGGCCGCAGGAACCCCTAGTGATGGAGTTGGCCACTCCCTCTCTGCGCG
CTCGCTCGCTCACTGAGGCCGGGCGACCAAAGGTCGCCCGACGCCCGGG
CTTTGCCCGGGCGGCCTCAGTGAGCGAGCGAGCGCGCAGCTGCCTGCAG
GGGCGCCTGATGCGGTATTTTCTCCTTACGCATCTGTGCGGTATTTCAC
ACCGCATACGTCAAAGCAACCATAGTACGCGCCCTGTAGCGGCGCATTA
AGCGCGGCGGGTGTGGTGGTTACGCGCAGCGTGACCGCTACACTTGCCA
GCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGG
TTCCGATTTAGTGCTTTACGGCACCTCGACCCCAAAAAACTTGATTTGG
GTGATGGTTCACGTAGTGGGCCATCGCCCTGATAGACGGTTTTTCGCCC
TTTGACGTTGGAGTCCACGTTCTTTAATAGTGGACTCTTGTTCCAAACT
GGAACAACACTCAACCCTATCTCGGGCTATTCTTTTGATTTATAAGGGA
TTTTGCCGATTTCGGCCTATTGGTTAAAAAATGAGCTGATTTAACAAAA
ATTTAACGCGAATTTTAACAAAATATTAACGTTTACAATTTTATGGTGC
ACTCTCAGTACAATCTGCTCTGATGCCGCATAGTTAAGCCAGCCCCGAC
ACCCGCCAACACCCGCTGACGCGCCCTGACGGGCTTGTCTGCTCCCGGC
ATCCGCTTACAGACAAGCTGTGACCGTCTCCGGGAGCTGCATGTGTCAG
AGGTTTTCACCGTCATCACCGAAACGCGCGAGACGAAAGGGCCTCGTGA
TACGCCTATTTTTATAGGTTAATGTCATGATAATAATGGTTTCTTAGAC
GTCAGGTGGCACTTTTCGGGGAAATGTGCGCGGAACCCCTATTTGTTTA
TTTTTCTAAATACATTCAAATATGTATCCGCTCATGAGACAATAACCCT
GATAAATGCTTCAATAATATTGAAAAAGGAAGAGTATGAGTATTCAACA
TTTCCGTGTCGCCCTTATTCCCTTTTTTGCGGCATTTTGCCTTCCTGTT
TTTGCTCACCCAGAAACGCTGGTGAAAGTAAAAGATGCTGAAGATCAGT
TGGGTGCACGAGTGGGTTACATCGAACTGGATCTCAACAGCGGTAAGAT
CCTTGAGAGTTTTCGCCCCGAAGAACGTTTTCCAATGATGAGCACTTTT
AAAGTTCTGCTATGTGGCGCGGTATTATCCCGTATTGACGCCGGGCAAG
AGCAACTCGGTCGCCGCATACACTATTCTCAGAATGACTTGGTTGAGTA
CTCACCAGTCACAGAAAAGCATCTTACGGATGGCATGACAGTAAGAGAA
TTATGCAGTGCTGCCATAACCATGAGTGATAACACTGCGGCCAACTTAC
TTCTGACAACGATCGGAGGACCGAAGGAGCTAACCGCTTTTTTGCACAA
CATGGGGGATCATGTAACTCGCCTTGATCGTTGGGAACCGGAGCTGAAT
```

-continued

```
GAAGCCATACCAAACGACGAGCGTGACACCACGATGCCTGTAGCAATGG
CAACAACGTTGCGCAAACTATTAACTGGCGAACTACTTACTCTAGCTTC
CCGGCAACAATTAATAGACTGGATGGAGGCGGATAAAGTTGCAGGACCA
CTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGA
TGGTAAGCCCTCCCGTATCGTAGTTATCTACACGACGGGGAGTCAGGCA
ACTATGGATGAACGAAATAGACAGATCGCTGAGATAGGTGCCTCACTGA
TTAAGCATTGGTAACTGTCAGACCAAGTTTACTCATATATACTTTAGAT
TGATTTAAAACTTCATTTTTAATTTAAAAGGATCTAGGTGAAGATCCTT
TTTGATAATCTCATGACCAAAATCCCTTAACGTGAGTTTTCGTTCCACT
GAGCGTCAGACCCCGTAGAAAAGATCAAAGGATCTTCTTGAGATCCTTT
TTTTCTGCGCGTAATCTGCTGCTTGCAAACAAAAAAACCACCGCTACCA
GCGGTGGTTTGTTTGCCGGATCAAGAGCTACCAACTCTTTTTCCGAAGG
TAACTGGCTTCAGCAGAGCGCAGATACCAAATACTGTCCTTCTAGTGTA
GCCGTAGTTAGGCCACCACTTCAAGAACTCTGTAGCACCGCCTACATAC
CTCGCTCTGCTAATCCTGTTACCAGTGGCTGCTGCCAGTGGCGATAAGT
CGTGTCTTACCGGGTTGGACTCAAGACGATAGTTACCGGATAAGGCGCA
GCGGTCGGGCTGAACGGGGGGTTCGTGCACACAGCCCAGCTTGGAGCGA
ACGACCTACACCGAACTGAGATACCTACAGCGTGAGCTATGAGAAAGCG
CCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGG
TATCTTTATAGTCCTGTCGGGTTTCGCCACCTCTGACTTGAGCGTCGAT
TTTTGTGATGCTCGTCAGGGGGGCGGAGCCTATGGAAAAACGCCAGCAA
CGCGGCCTTTTTACGGTTCCTGGCCTTTTGCTGGCCTTTTGCTCACATG
T
```

Preferably, the vector comprises a nucleic acid sequence substantially as set out in SEQ ID No: 16, or a fragment or variant thereof.

The following sequence, referred to herein as SEQ ID NO: 17, encodes a vector carrying AAV2 right and left ITRs. This vector is suitable for the production of AAV vectors; the genetic constructs of the first aspect can be subcloned into this vector. A map showing the features of a plasmid comprising SEQ ID NO: 17 is shown in FIG. 7. This vector is purely for illustrative purposes, and the skilled person would be aware of other suitable vectors. The pAV-FH vector sequence shown in FIG. 7, and other suitable vectors for the production of AAV vectors, are commercially available.

[SEQ ID NO: 17]

```
CCTGCAGGCAGCTGCGCGCTCGCTCGCTCACTGAGGCCGCCCGGGCGTC
GGGCGACCTTTGGTCGCCCGGCCTCAGTGAGCGAGCGAGCGCGCAGAGA
GGGAGTGGCCAACTCCATCACTAGGGGTTCCTGCGGCCGGTCGCGTCTA
GTTATTAATAGTAATCAATTACGGGGTCATTAGTTCATAGCCCATATAT
GGAGTTCCGCGTTACATAACTTACGGTAAATGGCCCGCCTGGCTGACCG
```

-continued

```
CCCAACGACCCCCGCCCATTGACGTCAATAATGACGTATGTTCCCATAG
TAACGCAATAGGGACTTTCCATTGACGTCAATGGGTGGAGTATTTACGG
TAAACTGCCCACTTGGCAGTACATCAAGTGTATCATATGCCAAGTACGC
CCCCTATTGACGTCAATGACGGTAAATGGCCCGCCTGGCATTATGCCCA
GTACATGACCTTATGGGACTTTCCTACTTGGCAGTACATCTACGTATTA
GTCATCGCTATTACCATGGTGATGCGGTTTTGGCAGTACATCAATGGGC
GTGGATAGCGGTTTGACTCACGGGGATTTCCAAGTCTCCACCCCATTGA
CGTCAATGGGAGTTTGTTTTGCACCAAAATCAACGGGACTTTCCAAAAT
GTCGTAACAACTCCGCCCCATTGACGCAAATGGGCGGTAGGCGTGTACG
GTGGGAGGTCTATATAAGCAGAGCTGTTTAGTGAACCGTCAGATCGCCT
GGAGACGCCATCCACGCTGTTTTGACCTCCATAGAAGACACCGGGACCG
ATCCAGCCTCCGCGGATTCGAATCCCGGCCGGGAACGGTGCATTGGAAC
GCGGATTCCCCGTGCCAAGAGTGACGTAAGTACCGCCTATAGAGTCTAT
AGGCCCACAAAAAATGCTTTCTTCTTTTAATATACTTTTTTGTTTATCT
TATTTCTAATACTTTCCCTAATCTCTTTCTTTCAGGGCAATAATGATAC
AATGTATCATGCCTCTTTGCACCATTCTAAAGAATAACAGTGATAATTT
CTGGGTTAAGGCAATAGCAATATTTCTGCATATAAATATTTCTGCATAT
AAATTGTAACTGATGTAAGAGGTTTCATATTGCTAATAGCAGCTACAAT
CCAGCTACCATTCTGCTTTTATTTTATGGTTGGGATAAGGCTGGATTAT
TCTGAGTCCAAGCTAGGCCCTTTTGCTAATCATGTTCATACCTCTTATC
TTCCTCCCACAGCTCCTGGGCAACGTGCTGGTCTGTGTGCTGGCCCATC
ACTTTGGCAAAGAATTGGGATTCGAACATCGATTGAATTCAGATCCGCT
AGTAATACGACTCACTATAGGGAGAGGATCCGGTACCGAGGAGATCTGC
CGCCGCGATCGCCGGCGCGCCAGATCTCACGCTTAACTAGCTAGCGGAC
CGACGCGTACGCGGCCGCTCGAGGATTATAAGGATGACGACGATAAATT
CGTCGAGCACCACCACCACCACCACTAATAAGGTTTATCCGATCCACCG
GATCTAGATAAGATATCCGATCCACCGGATCTAGATAACTGATCATAAT
CAGCCATACCACATTTGTAGAGGTTTTACTTGCTTTAAAAAACCTCCCA
CACCTCCCCCTGAACCTGAAACATAAAATGAATGCAATTGTTGTTGTTA
ACTTGTTTATTGCAGCTTATAATGGTTACAAATAAAGCAATAGCATCAC
AAATTTCACAAATAAAGCATTTTTTTCACTGCATTCTAGTTGTGGTTTG
TCCAAACTCATCAATGTATCTTAACGCGGTAACCACGTGCGGACCCAAC
GGCCGCAGGAACCCCTAGTGATGGAGTTGGCCACTCCCTCTagagCTGC
GCGCTCGCTCGCTCACTGAGGCCGGGCGACCAAAGGTCGCCCGACGCCC
GGGCTTTGCCCGGGCGGCCTCAGTGAGCGAGCGAGCGCGCAGCTGCCTG
CAGGGGCGCCTGATGCGGTATTTTCTCCTTACGCATCTGTGCGGTATTT
CACACCGCATACGTCAAAGCAACCATAGTACGCGCCCTGTAGCGGCGCA
TTAAGCGCGGCGGGTGTGGTGGTTACGCGCAGCGTGACCGCTACACTTG
CCAGCGCCCTAGCGCCCGCTCCTTTCGCTTTCTTCCCTTCCTTTCTCGC
CACGTTCGCCGGCTTTCCCCGTCAAGCTCTAAATCGGGGGCTCCCTTTA
GGGTTCCGATTTAGTGCTTTACGGCACCTCGACCCCAAAAAACTTGATT
```

-continued

TGGGTGATGGTTCACGTAGTGGGCCATCGCCCTGATAGACGGTTTTTCG
CCCTTTGACGTTGGAGTCCACGTTCTTTAATAGTGGACTCTTGTTCCAA
ACTGGAACAACACTCAACCCTATCTCGGGCTATTCTTTTGATTTATAAG
GGATTTTGCCGATTTCGGCCTATTGGTTAAAAAATGAGCTGATTTAACA
AAAATTTAACGCGAATTTTAACAAAATATTAACGTTTACAATTTTATGG
TGCACTCTCAGTACAATCTGCTCTGATGCCGCATAGTTAAGCCAGCCCC
GACACCCGCCAACACCCGCTGACGCGCCCTGACGGGCTTGTCTGCTCCC
GGCATCCGCTTACAGACAAGCTGTGACCGTCTCCGGGAGCTGCATGTGT
CAGAGGTTTTCACCGTCATCACCGAAACGCGCGAGACGAAAGGGCCTCG
TGATACGCCTATTTTTATAGGTTAATGTCATGATAATAATGGTTTCTTA
GACGTCAGGTGGCACTTTTCGGGGAAATGTGCGCGGAACCCCTATTTGT
TTATTTTTCTAAATACATTCAAATATGTATCCGCTCATGAGACAATAAC
CCTGATAAATGCTTCAATAATATTGAAAAAGGAAGAGTATGAGTATTCA
ACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATC
AGTTGGGTGCACGAGTGGGTTACATCGAACTGGATCTCAACAGCGGTAA
GATCCTTGAGAGTTTTCGCCCCGAAGAACGTTTTCCAATGATGAGCACT
TTTAAAGTTCTGCTATGTGGCGCGGTATTATCCCGTATTGACGCCGGGC
AAGAGCAACTCGGTCGCCGCATACACTATTCTCAGAATGACTTGGTTGA
GTACTCACCAGTCACAGAAAAGCATCTTACGGATGGCATGACAGTAAGA
GAATTATGCAGTGCTGCCATAACCATGAGTGATAACACTGCGGCCAACT
TACTTCTGACAACGATCGGAGGACCGAAGGAGCTAACCGCTTTTTTGCA
CAACATGGGGGATCATGTAACTCGCCTTGATCGTTGGGAACCGGAGCTG
AATGAAGCCATACCAAACGACGAGCGTGACACCACGATGCCTGTAGCAA
TGGCAACAACGTTGCGCAAACTATTAACTGGCGAACTACTTACTCTAGC
TTCCCGGCAACAATTAATAGACTGGATGGAGGCGGATAAAGTTGCAGGA
CCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCC
AGATGGTAAGCCCTCCCGTATCGTAGTTATCTACACGACGGGGAGTCAG
GCAACTATGGATGAACGAAATAGACAGATCGCTGAGATAGGTGCCTCAC
TGATTAAGCATTGGTAACTGTCAGACCAAGTTTACTCATATATACTTTA
GATTGATTTAAAACTTCATTTTTAATTTAAAAGGATCTAGGTGAAGATC
CTTTTTGATAATCTCATGACCAAAATCCCTTAACGTGAGTTTTCGTTCC
ACTGAGCGTCAGACCCCGTAGAAAAGATCAAAGGATCTTCTTGAGATCC
TTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGA
AGGTAACTGGCTTCAGCAGAGCGCAGATACCAAATACTGTCCTTCTAGT
GTAGCCGTAGTTAGGCCACCACTTCAAGAACTCTGTAGCACCGCCTACA
TACCTCGCTCTGCTAATCCTGTTACCAGTGGCTGCTGCCAGTGGCGATA
AGTCGTGTCTTACCGGGTTGGACTCAAGACGATAGTTACCGGATAAGGC

-continued

GCAGCGGTCGGGCTGAACGGGGGGTTCGTGCACACAGCCCAGCTTGGAG
CGAACGACCTACACCGAACTGAGATACCTACAGCGTGAGCTATGAGAAA
GCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTC
GATTTTTGTGATGCTCGTCAGGGGGGCGGAGCCTATGGAAAAACGCCAG
CAACGCGGCCTTTTTACGGTTCCTGGCCTTTTGCTGGCCTTTTGCTCAC
ATGT

Preferably, the recombinant vector of the invention may comprise a nucleic acid sequence which enhances expression of tyrosine hydroxylase (TH) and GTP cyclohydrolase 1 (GCH1). More preferably, the nucleic acid sequence comprises or consists of an optimised intron with pUC origin and RNA-OUT (OIPR) sequence, as described in Lu et al, 2017, "A 5' Noncoding Exon Containing Engineered Intron Enhances Transgene Expression from Recombinant AAV Vectors in vivo", Human Gene Therapy, Volume 28, Page 125-134 and WO2013119371.

The OIPR sequence may be referred to herein as SEQ ID No: 26, as follows:

[SEQ ID No: 26]

ATTGGGATCTTCACACAGCAGGTAAGGTTGCGGGCCGGGCCTGGGCCGG
GTCCGGGCCGGGTATTGCCCGCCTAATGAGCGGGCTTTTTTTTCTTACC
CCTTCTTCCGCTTCCTCGCTCACTGACTCGCTGCGCTCGGTCGTTCGGC
TGCGGCGAGCGGTATCAGCTCACTCAAAGGCGGTAATACGGTTATCCAC
AGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGC
TCCGCCCCCCTGACGAGCATCACAAAAATCGACGCTCAAGTCAGAGGTG
GCGAAACCCGACAGGACTATAAAGATACCAGGCGTTTCCCCCTGGAAGC
TCCCTCGTGCGCTCTCCTGTTCCGACCCTGCCGCTTACCGGATACCTGT
CCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATC
GTCTTGAGTCCAACCCGGTAAGACACGACTTATCGCCACTGGCAGCAGC
CACTGGTAACAGGATTAGCAGAGCGAGGTATGTAGGCGGTGCTACAGAG
TTCTTGAAGTGGTGGCCTAACTACGGCTACACTAGAAGAACAGTATTTG
GTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTT
TGCAAGCAGCAGATTACGCGCAGAAAAAAAGGATCTCAAGAAGATCCTT
TGATCTTTTCTACGGGGTCTGACGCTCAGTGGAACGAAAACTCACGTTA
AGGGATTTTGGTCATGAGATTATCAAAAAGGATCTTCACCTAGATCCTT
TTAAATTAAAAATGAAGTTTTAAATCAATCTAAAGTATATATGAGTAAA
CTTGGTCTGACAGTTACCAATGCTTAATCAGTGAGGCACCTATCTCAGC
GATCTGTCTATTTCGTTCATCCATAGTTGCCTGACTCCTGCAAACCACG
TTGTGGTAGAATTGGTAAAGAGAGTCGTGTAAAATATCGAGTTCGCACA

-continued

```
TCTTGTTGTCTGATTATTGATTTTTGGCGAAACCATTTGATCATATGAC

AAGATGTGTATCTACCTTAACTTAATGATTTTGATAAAAATCATTAGGT

ACCCCGGCCCGCACTGACCCCTGGTGTTGCTTTTTTTTTTTAGGCCGCA

AGCTGAAGCGTGTCC
```

Preferably, the OIPR sequence comprises a nucleic acid sequence substantially as set out in SEQ ID No: 26, or a fragment or variant thereof.

Preferably, the OIPR sequence is located within the main cassette and is disposed 3' of the promoter sequence, and 5' of the coding sequences of tyrosine hydroxylase (TH) and GTP cyclohydrolase 1 (GCH1).

The gene therapy vectors may be produced by any technique known in the art. For instance, the rAAV vectors may be produced using classic triple transfection methodology. Methods for the production of adeno-associated virus vectors are disclosed in Matsushita et al. (Matsushita et al., Adeno-associated virus vectors can be efficiently produced without helper virus. Gene Therapy (1998) 5, 938-945)

Hence, according to a third aspect, there is provided a method of manufacturing a gene therapy vector, the method comprising, (i) introducing into a host cell a nucleic acid sequence comprising a genetic construct according to the first aspect or a recombinant vector according to the second aspect, and (ii) culturing the host cell under conditions to result in the production of a gene therapy vector comprising the genetic construct according to the first aspect or the recombinant vector according to the second aspect.

The recombinant vectors of the second aspect are particularly suitable for therapy.

Hence, according to a fourth aspect, there is provided the genetic construct according to the first aspect, or the recombinant vector according to the second aspect, for use as a medicament or in therapy.

According to a fifth aspect, there is provided the genetic construct according to the first aspect, or the recombinant vector according to the second aspect, for use in treating, preventing, or ameliorating a neurodegenerative disorder.

According to a sixth aspect, there is provided a method of treating, preventing, or ameliorating a neurodegenerative disorder in a subject, the method comprising administering, to a subject in need of such treatment, a therapeutically effective amount of the genetic construct according to the first aspect, or the recombinant vector according to the second aspect.

Preferably, the genetic construct or the recombinant vector according to the invention are used in a gene therapy technique.

In an embodiment, the neurodegenerative disorder to be treated is a disease associated with catecholamine dysfunction. In a preferred embodiment, the catecholamine dysfunction may be characterised by a dopamine deficiency. In another embodiment, the disorder to be treated is selected from the group consisting of Parkinson's disease, DOPA responsive dystonia, vascular parkinsonism, side effects associated with L-DOPA treatment, L-DOPA induced dyskinesia, Segawa syndrome, or genetic dopamine receptor abnormalities. In a more preferred embodiment, the disease to be treated is Parkinson's disease.

The disclosed gene therapy technique leads to a constant level of production of L-DOPA in the striatum. This removes or reduces the need for oral L-DOPA and so results in reduced peak to trough variation. Hence, the disclosed gene therapy can be used for the treatment of side effects associated with L-DOPA treatment and of L-DOPA induced dyskinesia.

The disclosed gene therapy technique may be used for the treatment of Segawa syndrome. Although it would be possible to treat Segawa syndrome with a gene therapy delivering only GCH1, the inclusion of TH is not expected to be prejudicial and may be beneficial. The disclosed treatment is especially advantageous as, due to the rareness of Segawa syndrome, it may not be commercially attractive or viable to develop a treatment solely for this indication. Production of the disclosed invention for this indication as well as for other neurodegenerative diseases, such as Parkinson's disease, will reduce the unit cost of the therapy.

In a preferred embodiment, medicaments according to the invention may be administered to a subject by injection into the blood stream, a nerve, or directly into a site requiring treatment. For instance, the vector may be delivered to the brain. Specific regions of the brain may be targeted, such as striatum. The putamen or caudate nucleus may be targeted. The treatment may be centred on the dopaminergic neurons of the pars compacta region in the substantia nigra.

The delivery method may be direct injection. Methods for injection into the brain (for instance the striatum) are well known in the art (Bilang-Bleuel et al (1997) Proc. Acad. Nati. Sci. USA 94:8818-8823; Choi-Lundberg et al (1998) Exp. Neurol. 154:261-275; Choi-Lundberg et al (1997) Science 275:838-841; and Mandel et al (1997)) Proc. Acad. Natl. Sci. USA 94:14083-14088). Alternatively, or in addition, the vector chosen may have a tropism that is targeted towards a specific desired tissue, such as a neurone.

Modifications of the vector capsid properties could enable targeting of the vector to the striatal region also after intrathecal (IT) injection or injection into the cerebral ventricles (ICV). An alternative approach is to generate chimeric AAV serotypes that would inherit different binding properties from the two serotypes mixed.

In one embodiment the genome sequence described herein, i.e. the promoter-TH-linker-GCH1 sequence, may be administered by injection directly as naked DNA without a viral vector. The naked DNA may be administered as a plasmid. The naked DNA may be delivered as a plasmid administered in any suitable non-viral carrier that would be known to those skilled in the art.

Preferably, the non-viral carrier is selected from the groups consisting of: poly(2-ethyl-2-oxazoline)-PLA-g-PEI amphiphilic triblock micelles, a Poly(β-amino ester)-based biodegradable nanoparticle, a Pluronic® block-copolymer such as Pluronic F27, Pluronic F68 or Pluronic F85 a mixture of Pluronics such as SP1017, and a carrier such as BrainFectIn® (OZ Biosciences, Marseille, France).

It will be appreciated that the amount of the genetic construct or the recombinant vector that is required is determined by its biological activity and bioavailability, which in turn depends on the mode of administration, the physiochemical properties of the genetic construct or the recombinant vector and whether it is being used as a monotherapy or in a combined therapy. Optimal dosages to be administered may be determined by those skilled in the art, and will vary with the particular genetic construct or the recombinant vector in use, the strength of the pharmaceutical composition, the mode of administration, and the advancement of the neurodegenerative disorder. Additional factors depending on the particular subject being treated will result in a need to adjust dosages, including subject age, weight, gender, diet, and time of administration.

The dose delivered may be 300 μl to 4500 μl, 400 μl to 4000 μl, 500 μl to 3500 μl, 600 μl to 3000 μl, 700 μl to 2500 μl, 750 μl to 2000 μl, 800 μl to 1500 μl, 850 μl to 1000 μl, or roughly 900 μl. For delivery methods involving direct injection into the striatum, the two doses may be delivered, one per striatum. For example, one dose, such as 900 μl, may be delivered to the left side of the brain, and a further dose, such as 900 μl, may be delivered to the right side of the brain.

The titre of the dose may be 1E8 to 5E14, 1E9 to 1E14, 1E10 to 5E13, 1E11 to 1E13, 1E12 to 8E12, 4E12 to 6E12, or roughly 5E12 genome copies per ml (GC/ml).

The genetic construct or the recombinant vector may be administered before, during or after onset of the disorder. Doses may be given as a single administration, or multiple doses may be given over the course of the treatment. A dose may be administered to a patient, and the patient may be monitored in order to assess the necessity for a second or further doses. Repeat use delivery of the same genome may be facilitated by the switching the AAV capsid serotype to reduce the probability of interference by an antibody or cell mediated immune response induced by the previous treatment.

In some embodiments, the therapeutic methods may include, prior to gene therapy treatment, a test infusion of L-DOPA. The test infusion may be used to demonstrate that a subject is responsive to L-DOPA, and so may allow the selection of subjects most likely to benefit from gene therapy treatment. The L-DOPA test infusion may be by any means capable of creating a steady blood level over hours or days. Examples of suitable infusion methods include by nasogastric tube, i.v. infusion, infusion via a pump, by the use of DuoDOPA, or any other suitable means.

It will be appreciated that the genetic construct according to the first aspect, or the recombinant vector according to the second aspect may be used in a medicament, which may be used as a monotherapy (i.e. use of the genetic construct according to the first aspect or the vector according to the second aspect of the invention), for treating, ameliorating, or preventing any disorder as disclosed herein. Alternatively, the genetic construct or the recombinant vector according to the invention may be used as an adjunct to, or in combination with, known therapies for treating, ameliorating, or preventing any disorder as disclosed herein. In some cases, the genetic construct may be used as an adjunct to, in combination with, or alongside a treatment designed to improve the gene therapy. For instance, the genetic construct may be used in combination with an immunosuppressive treatment, in order to reduce, prevent, or control an immune response induced by the gene therapy itself. For example, the immunosuppressive treatment may prevent, reduce, or control an immune response directed to a capsid of a gene therapy vector, a genome comprised within a gene therapy vector, or a product produced by a gene therapy vector during therapy. The immunosuppressive regime may include a general immunosuppressant, such as steroid. The immunosuppressive regime may include more targeted immunosuppression designed to reduce specific immune responses, such as immunotherapy to specific antigens found within, or produced by, a gene therapy construct.

The genetic construct according or the recombinant vector according to the invention may be combined in compositions having a number of different forms depending, in particular, on the manner in which the composition is to be used. Thus, for example, the composition may be in the form of a powder, liquid, aerosol, spray, micellar solution, liposome suspension or any other suitable form that may be administered to a person or animal in need of treatment. It will be appreciated that the vehicle of medicaments according to the invention should be one which is well-tolerated by the subject to whom it is given.

Known procedures, such as those conventionally employed by the pharmaceutical industry (e.g. in vivo experimentation, clinical trials, etc.), may be used to form specific formulations of the genetic construct or the recombinant vector according to the invention and precise therapeutic regimes.

According to a seventh aspect, there is provided a pharmaceutical composition comprising the genetic construct according to the first aspect, or the recombinant vector according to the second aspect, and a pharmaceutically acceptable vehicle.

According to an eighth aspect, there is provided a method of preparing the pharmaceutical composition according to the seventh aspect, the method comprising contacting the genetic construct according to the first aspect, or the recombinant vector according to the second aspect, with a pharmaceutically acceptable vehicle.

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the genetic construct, the recombinant vector or the pharmaceutical composition is any amount which, when administered to a subject, is the amount of the aforementioned that is needed to treat the neurodegenerative disorder.

For example, the therapeutically effective amount of the genetic construct, the recombinant vector or the pharmaceutical composition used may be from about 0.01 mg to about 800 mg, and preferably from about 0.01 mg to about 500 mg. It is preferred that the amount of the genetic construct, the recombinant vector or the pharmaceutical composition is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In a preferred embodiment, the pharmaceutically acceptable vehicle may be such as to allow injection of the composition directly into a subject. For instance, the vehicle may be suitable for allowing the injection of the composition into the brain.

In one embodiment, the pharmaceutically acceptable vehicle may be a solid, and the composition may be in the form of a powder, or suspension. A solid pharmaceutically acceptable vehicle may include one or more substances which may also act as, lubricants, solubilisers, suspending agents, dyes, fillers, glidants, compression aids, inert binders, preservatives, dyes, coatings, or solid-disintegrating agents. The vehicle may also be an encapsulating material. In powders, the vehicle is a finely divided solid that is in admixture with the finely divided active agents according to the invention. In another embodiment, the pharmaceutical vehicle may be a gel or the like.

However, the pharmaceutical vehicle may be a suspension or a liquid, and the pharmaceutical composition is in the form of a suspension or a solution. Liquid pharmaceutical compositions, which are sterile solutions or suspensions, can be utilized by, for example, intramuscular, intrathecal, epidural, intraperitoneal, intravenous and particularly subcutaneous injection. The genetic construct or the recombinant vector may be prepared as a sterile solid composition that may be dissolved or suspended at the time of administration using sterile water, saline, Dulbecco's Phosphate Buffered Saline (dPBS) with MgCl2 and CaCl2, or other appropriate sterile injectable medium.

Finally, in another aspect of the invention, there is provided a genetic construct comprising a promoter operably linked to a first coding sequence, which encodes tyrosine hydroxylase (TH), and a second coding sequence, which encodes GTP cyclohydrolase 1 (GCH1), wherein the second coding sequence is 3' to the first coding sequence, and the first and second coding sequences are part of a single operon.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID No:1-31, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in, for example, SEQ ID Nos: 3 and 5.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figure, in which:—

EXAMPLES

The inventor has investigated gene therapy for treating neurodegenerative disorders, including dopamine deficiency disorders, and Parkinson's disease. The inventor has developed a novel genetic construct and associated AAV vector for use in treating Parkinson's disease.

Example 1—Assessment of Tyrosine Hydroxylase Gene Expression

Background

A reference plasmid corresponding to the prior art plasmid of WO 2011/054976 A2 was utilised in this study. This plasmid is graphically depicted in the map of FIG. 8.

The reference plasmid contains two separate expression cassettes for the murine GTH cyclohydrase 1 (GCH1) and human tyrosine hydroxylase (TH) genes. The purpose of the study was to compare TH expression of the aforementioned reference plasmid at the mRNA level versus three embodiments of the present invention, or a combination of two plasmids, each expressing a single gene, so as to identify a dual gene expression plasmid with improved TH expression.

Preliminary Experiment

Figure 9:
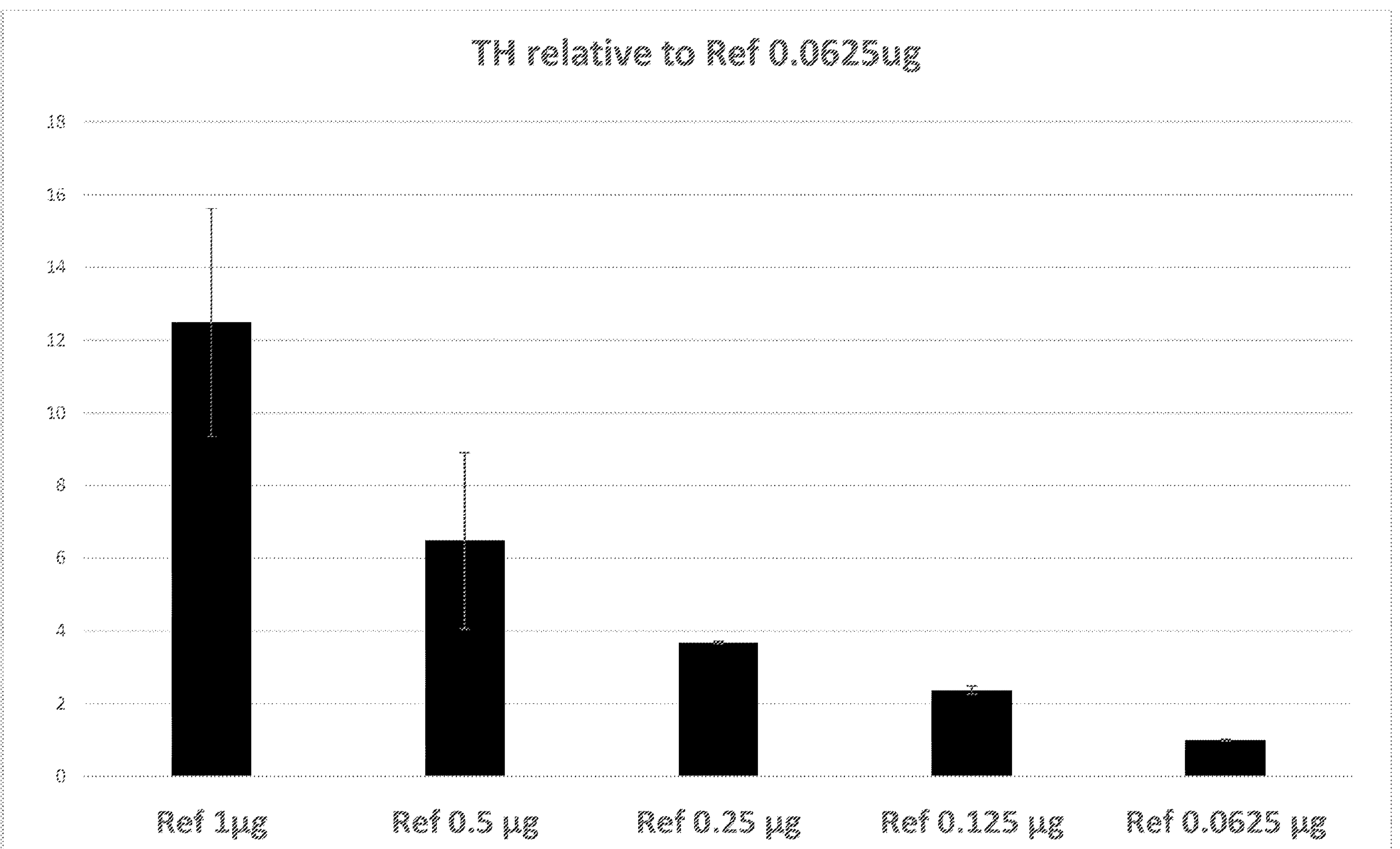
FIG. 9 is a graphical representation of the results of an in vitro assay comparing TH expression at various amounts of DNA.

HEK 293 cells were transfected with five different amounts of the reference plasmid, followed by RNA extraction, cDNA synthesis, and subsequent assessment of mRNA expression of GAPDH (housekeeping gene) and human TH by qPCR. The results of this assay are shown in FIG. 9.

Three DNA amounts, 0.25 μg, 0.125 μg and 0.0625 μg, were selected for use in further experiments.

Comparison between the prior art constructs and embodiments of the invention HEK 293 cells were transfected, at the three DNA doses selected from the preliminary experiment, with either the reference plasmid or the four test conditions (Test1-Test4). This was followed by RNA extractions, cDNA synthesis and subsequent assessment of mRNA expression of GAPDH (housekeeping gene) and human tyrosine kinase by qPCR. The sample Ref 0.0625 μg was selected as the calibrator sample for qPCR analysis.

Test1 comprised transfection with a plasmid of a sequence according to SEQ ID NO: 18. This plasmid is graphically depicted in the map of FIG. 10. This construct comprises a sequence encoding TH, an IRES, and a downstream sequence encoding GCH1.

Test2 comprised transfection with a plasmid of a sequence according to SEQ ID NO: 19. This plasmid is graphically depicted in the map of FIG. 11. This construct comprises a sequence encoding TH, a furin cleavage site, a viral 2A peptide spacer, and a downstream sequence encoding GCH1.

Test3 comprised transfection with a plasmid of a sequence according to SEQ ID NO: 20. This plasmid is graphically depicted in the map of FIG. 12. This construct comprises a sequence encoding TH, a flexible linker, and a downstream sequence encoding GCH1.

Figure 13:
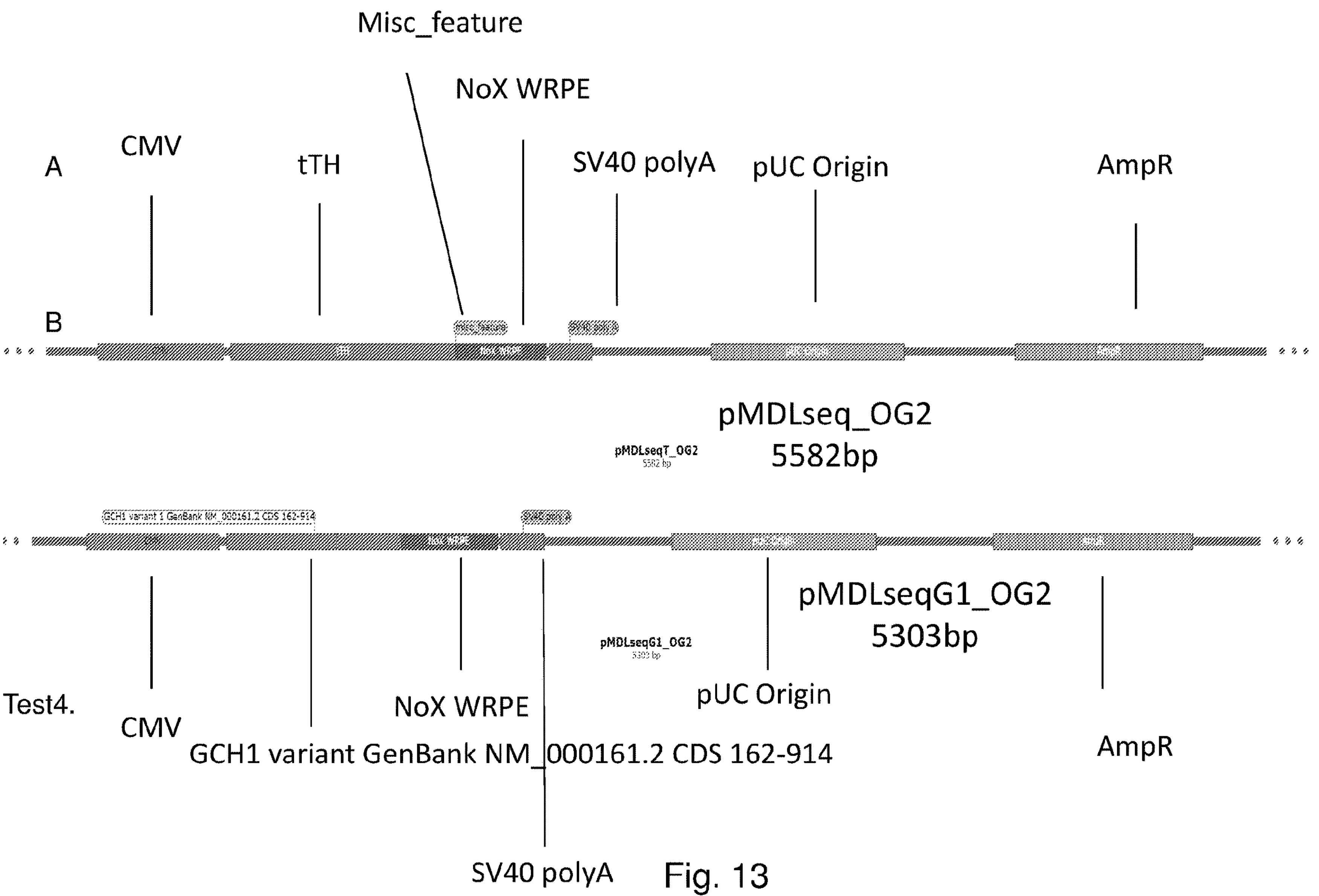
FIG. 13A is a plasmid map of a monocistronic construct which includes TH.
FIG. 13B is a plasmid map of a monocistronic construct which includes GCH1.

Test4 comprised transfection involving co-administration of a plasmid graphically depicted in the map of FIG. 13A and of a plasmid graphically depicted in the map of FIG. 13B. One construct encodes TH (FIG. 13A), whereas the other construct encodes GCH1 (FIG. 13B). Test4 was to allow the testing of the expression achieved by the above bicistronic constructs over these two co-administered monocistronic constructs.

Figure 1:
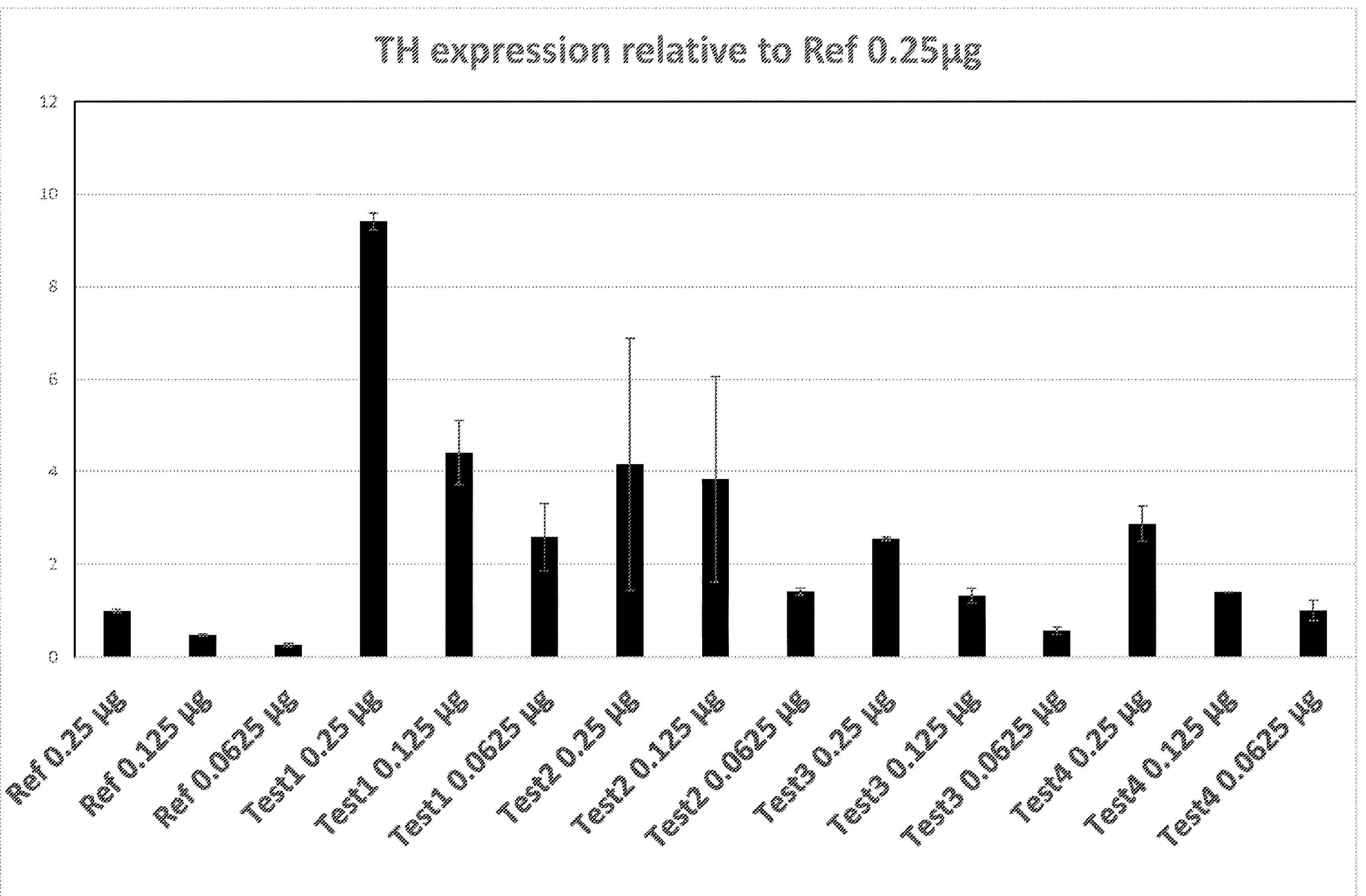
FIG. 1 is a graphical representation of the results of an in vitro assay comparing the TH expression between various embodiments of the constructs of the invention and those described in prior art references.

The results of this experiment are shown in FIG. 1 and Table 1. Test1, Test2, and Test3 (embodiments of the present invention) were all improved over the reference plasmid. Test1 resulted in an up to 9.4-fold increase in mRNA expression over the reference plasmid. It is notable that if sample Ref 0.0625 μg were used as the calibrator sample, up to 9.9-fold increase in mRNA level could be detected.

TABLE 1

| Assessment of Tyrosine Hydroxylase gene expression | | |
|---|---|---|
| | Av | SD |
| Ref 0.25 μg | 1 | 0.032029 |
| Ref 0.125 μg | 0.481388 | 0.024329 |
| Ref 0.0625 μg | 0.261409 | 0.033758 |
| Test1 0.25 μg | 9.411235 | 0.182147 |
| Test1 0.125 μg | 4.417566 | 0.702172 |
| Test1 0.0625 μg | 2.587243 | 0.722136 |
| Test2 0.25 μg | 4.161938 | 2.724108 |
| Test2 0.125 μg | 3.838677 | 2.227054 |
| Test2 0.0625 μg | 1.415666 | 0.075599 |
| Test3 0.25 μg | 2.553369 | 0.039338 |
| Test3 0.125 μg | 1.326091 | 0.157098 |
| Test3 0.0625 μg | 0.574204 | 0.077967 |
| Test4 0.25 μg | 2.877203 | 0.380339 |
| Test4 0.125 μg | 1.401549 | 0.002572 |
| Test4 0.0625 μg | 1.009721 | 0.216553 |

Surprisingly, Test1 and Test2 were also improved over Test4 (the co-administered monocistronic constructs). This is particularly advantageous as therapy with a single biscistronic construct has further advantages over therapy using two monocistronic constructs. These advantages are as disclosed herein, but in short the bicistronic construct ensures that the genes are delivered to the same cell and also has advantages in manufacturing and economy.

Example 2—Assessment of Murine GTP Cyclohydrolase 1 Gene Expression

The purpose of this study was to quantify expression of the murine GCH1 gene from vectors featuring a number of gene configurations. In particular, two embodiments of the invention were compared to a reference plasmid corresponding to the prior art plasmid of WO2011/054976 A2.

Figure 8:
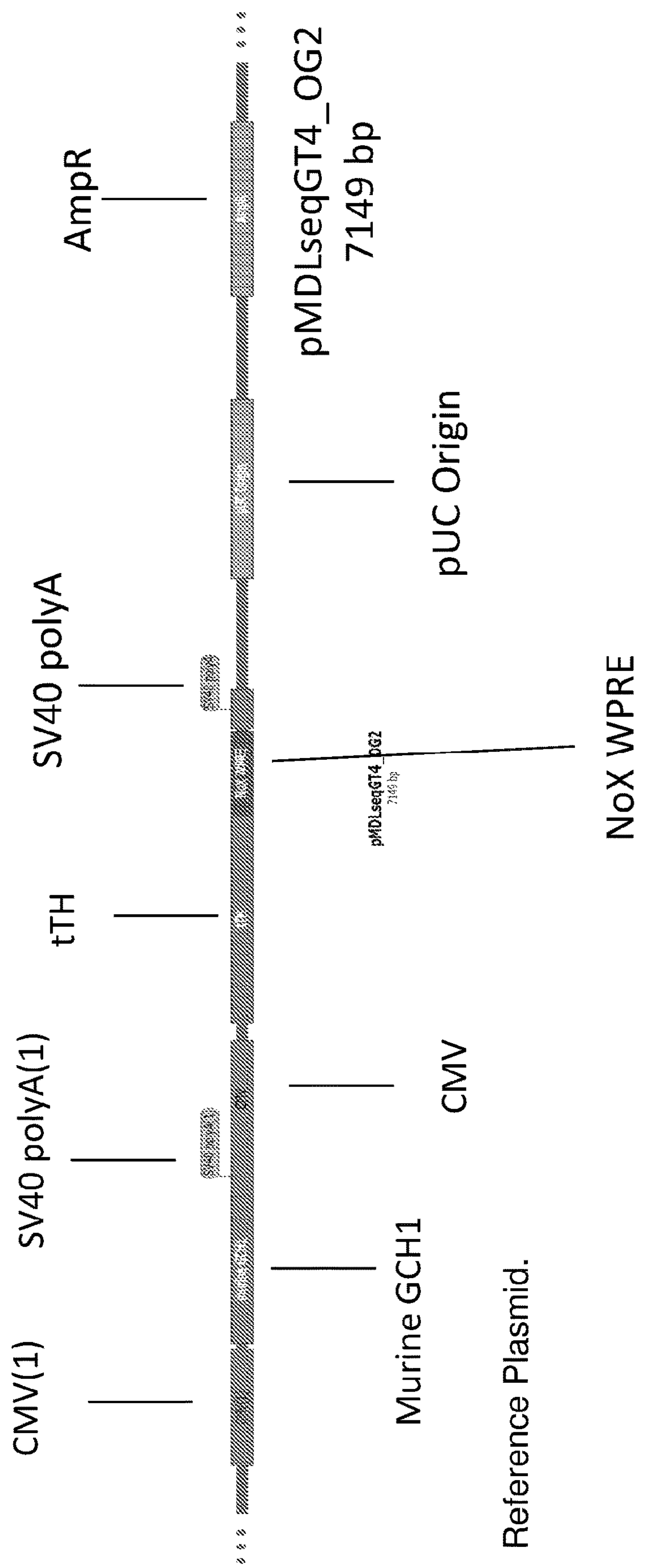
FIG. 8 is a plasmid map of a construct corresponding to the construct of WO2011/054976, and used herein as a reference plasmid.

The reference plasmid was the same as that described in Example 1 and FIG. 8.

Figure 10:
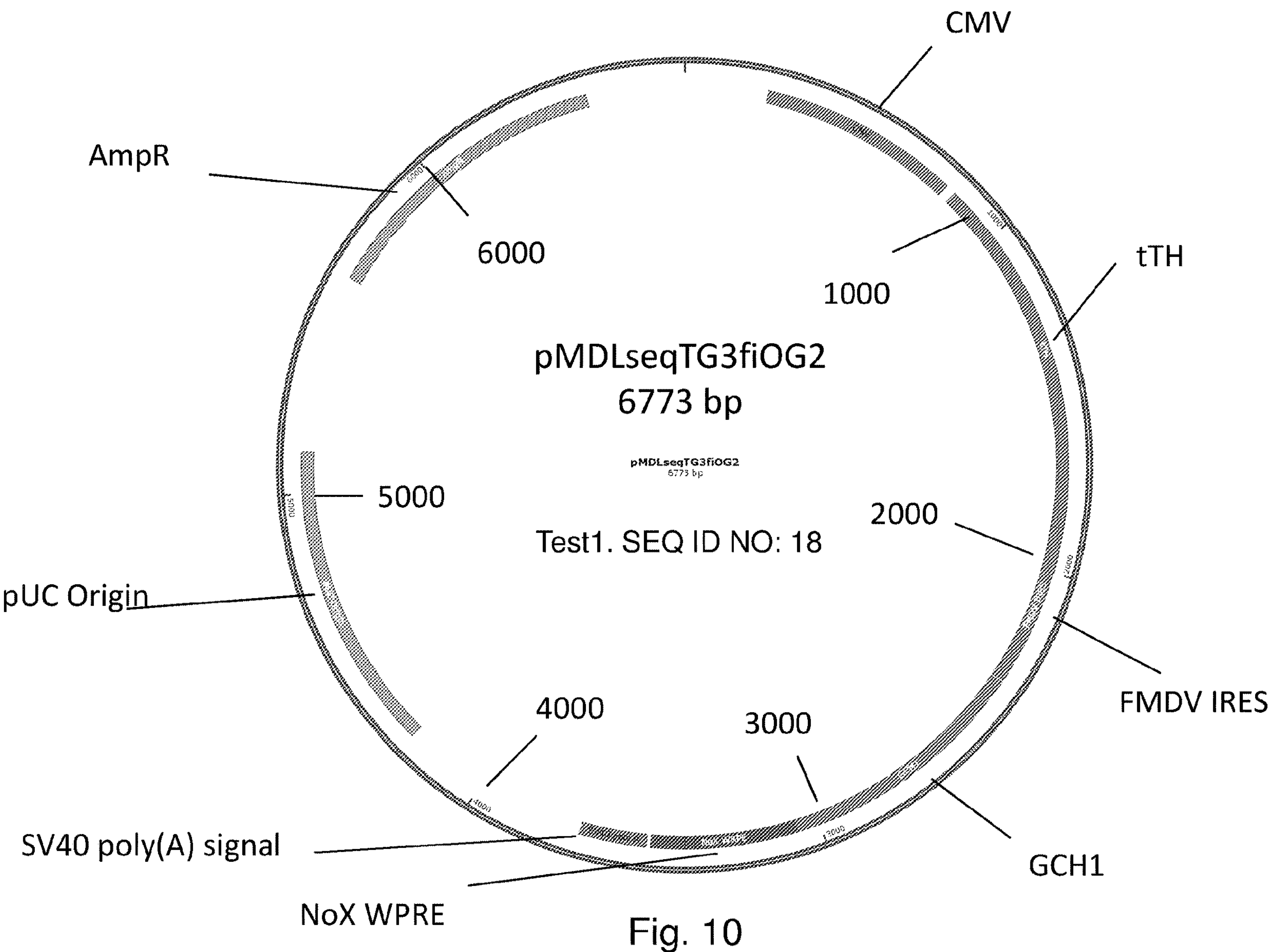
FIG. 10 is a plasmid map of a sixth embodiment of the construct of the invention, showing the features of SEQ ID NO: 18.

The plasmid used in Test1 was the same as that described in Example 1, FIG. 10, and SEQ ID NO: 18.

Figure 11:
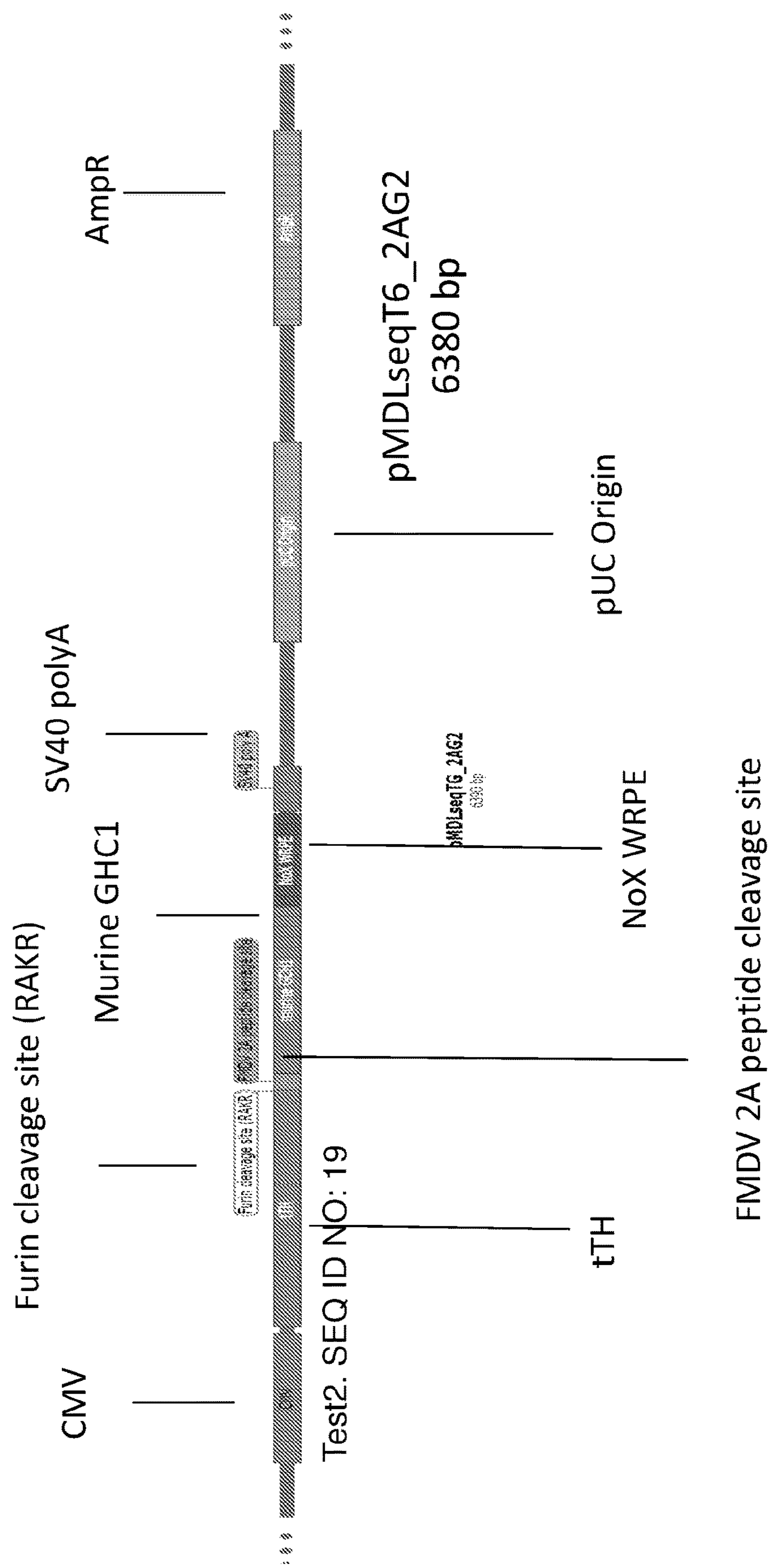
FIG. 11 is a plasmid map of a seventh embodiment of the construct of the invention, showing the features of SEQ ID NO: 19.

The plasmid used in Test2 was the same as that described in Example 1, FIG. 11, and SEQ ID NO: 19.

Figure 2:
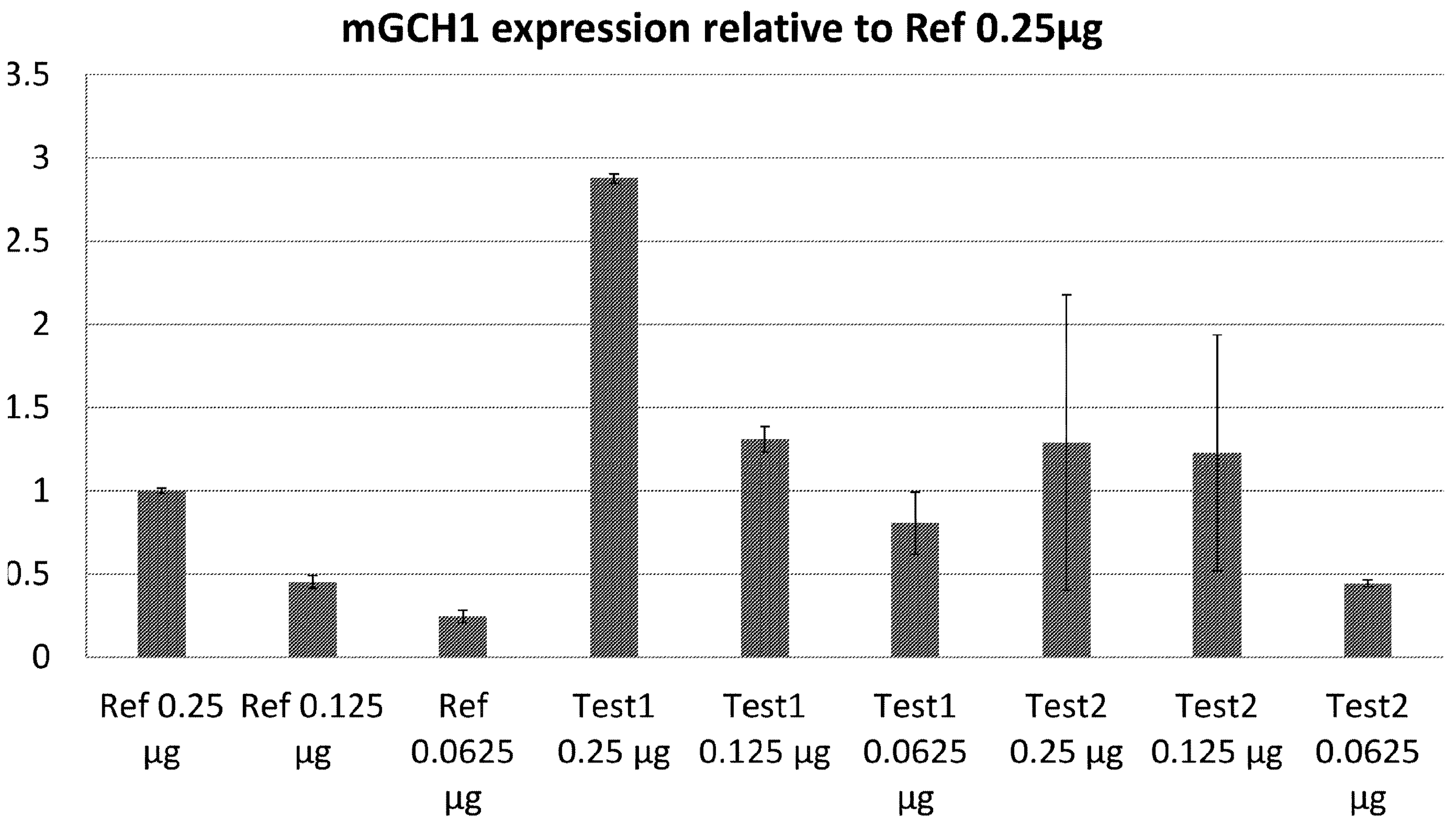
FIG. 2 is a graphical representation of the results of an in vitro assay comparing the GCH1 expression between various embodiments of the construct of the invention and those described in prior art references.

The results of this experiment are shown in FIG. 2 and Table 2. Test1 and Test2 (embodiments of the present invention) were improved over the reference plasmid. Notably, an up to 2.9-fold increase in mRNA expression was observed for Test1 plasmid over the reference plasmid, and if using sample Ref 0.0625 μg as the calibrator sample, up to 3.3-fold increase in mRNA level could be detected.

TABLE 2

| Assessment of murine GTP cyclohydrolase 1 gene expression | | |
|---|---|---|
| | Av | SD |
| Ref 0.25 μg | 1 | 0.016089 |
| Ref 0.125 μg | 0.452139 | 0.040327 |
| Ref 0.0625 μg | 0.244783 | 0.037694 |
| Test1 0.25 μg | 2.874335 | 0.029164 |
| Test1 0.125 μg | 1.309529 | 0.077492 |
| Test1 0.0625 μg | 0.8055 | 0.187179 |
| Test2 0.25 μg | 1.289959 | 0.887127 |
| Test2 0.125 μg | 1.226948 | 0.708271 |
| Test2 0.0625 μg | 0.442867 | 0.021152 |

Example 3—In Vivo Assessment of the Construct of the Invention

Figure 3:
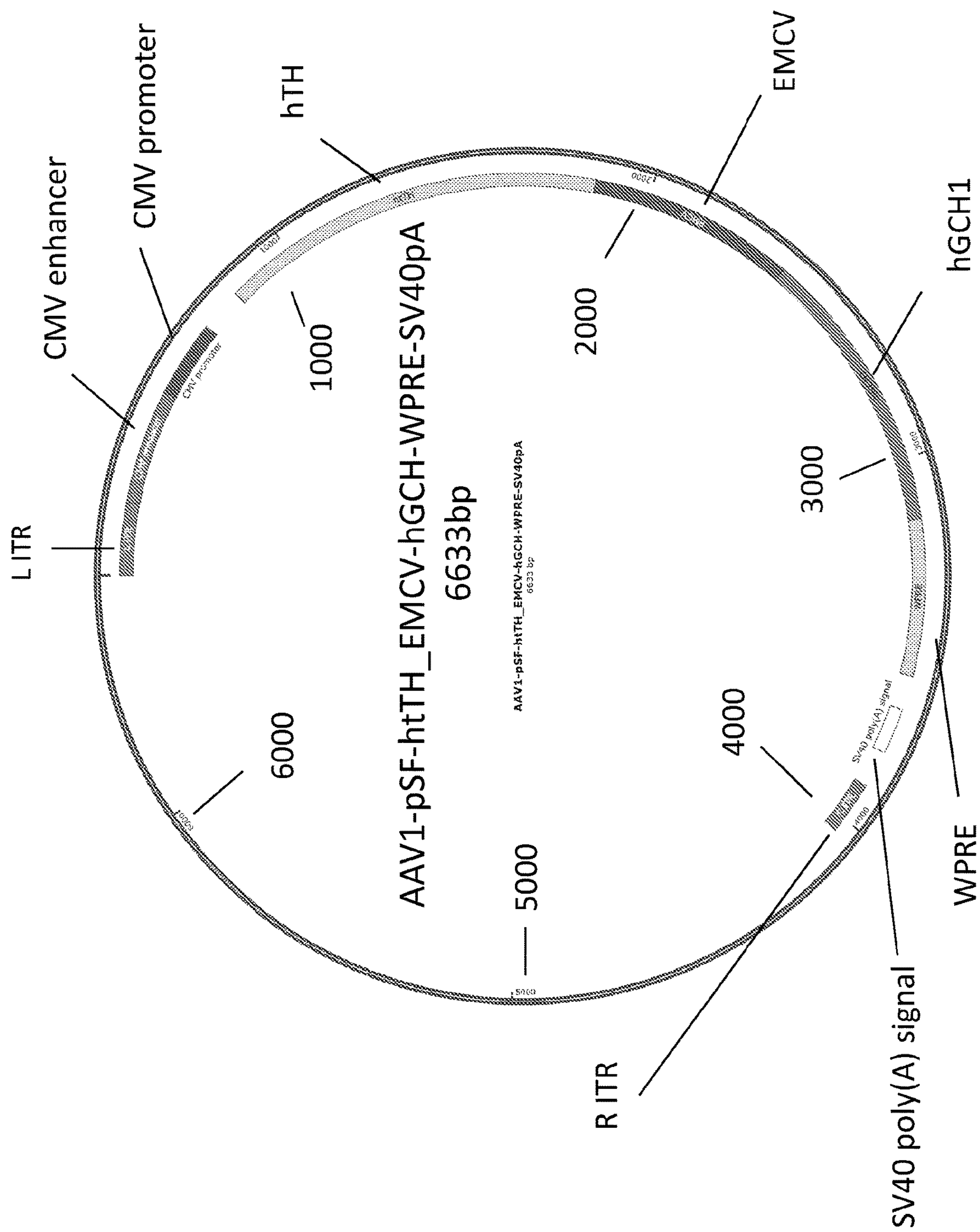
FIG. 3 is a plasmid map of a first embodiment of the construct of the invention, showing the features of SEQ ID NO: 13.
Figure 4:
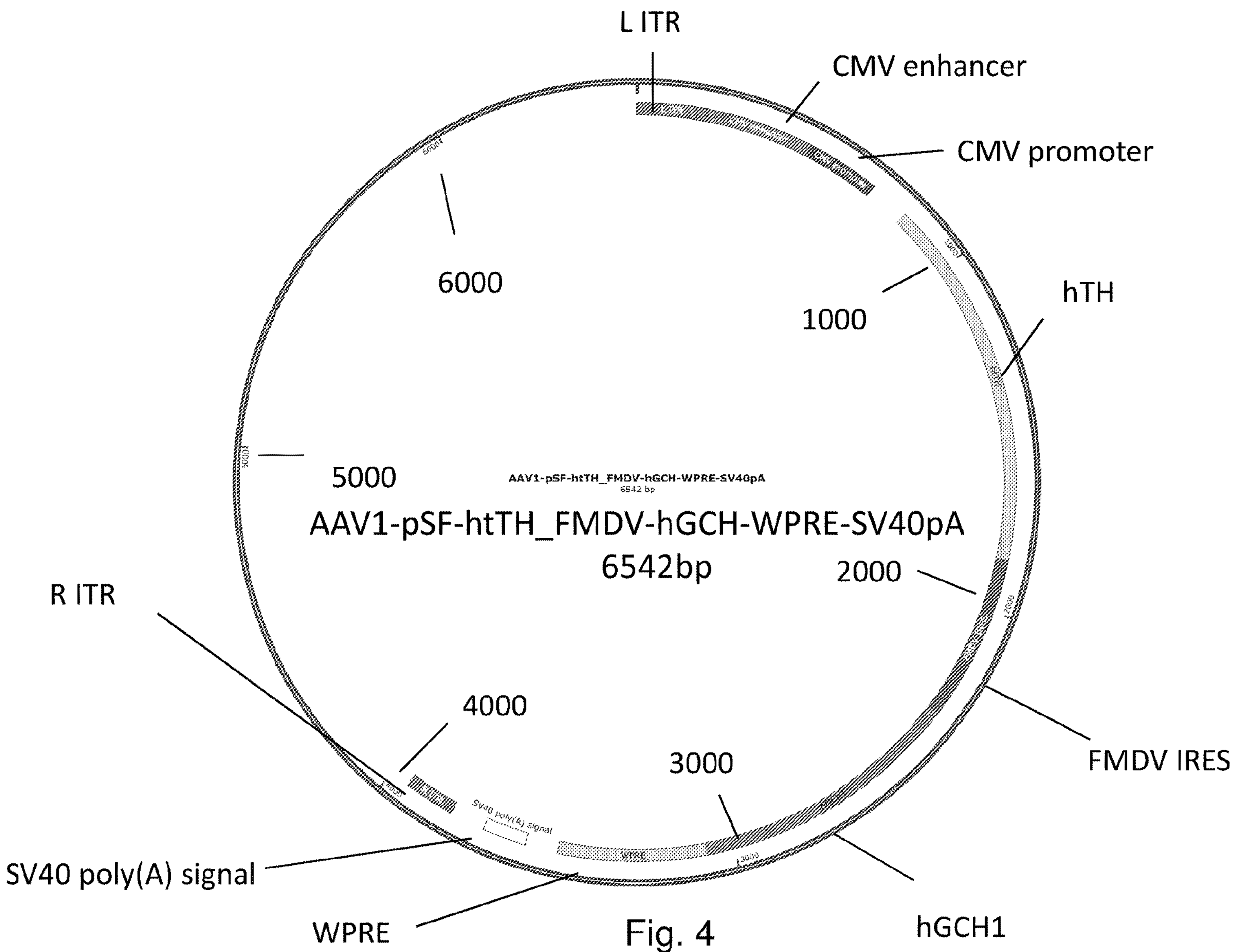
FIG. 4 is a plasmid map of a second embodiment of the construct of the invention, showing the features of SEQ ID NO: 14.
Figure 5:
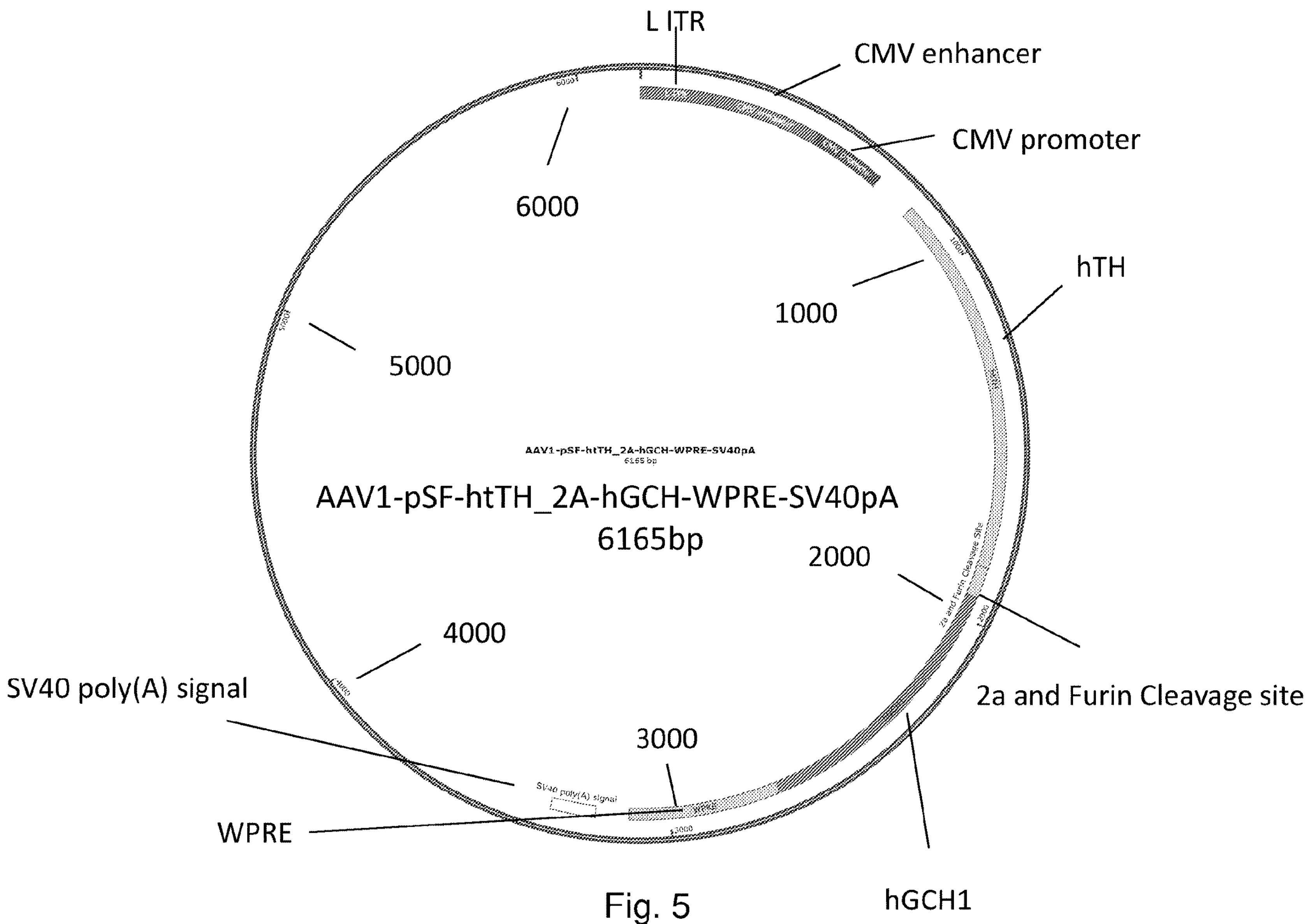
FIG. 5 is a plasmid map of a third embodiment of the construct of the invention, showing the features of SEQ ID NO: 15.
Figure 6:
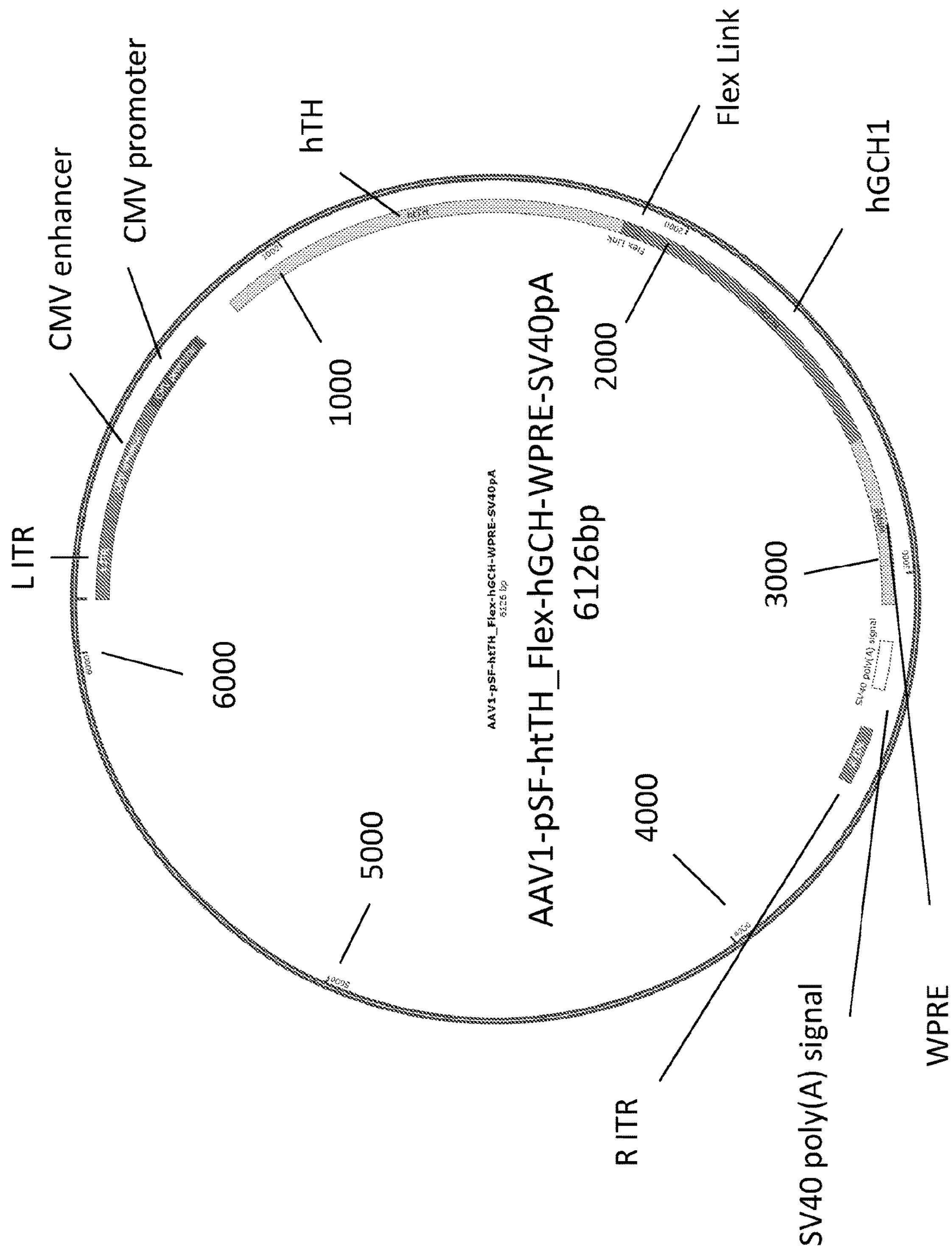
FIG. 6 is a plasmid map of a fourth embodiment of the construct of the invention, showing the features of SEQ ID NO: 16.
Figure 7:
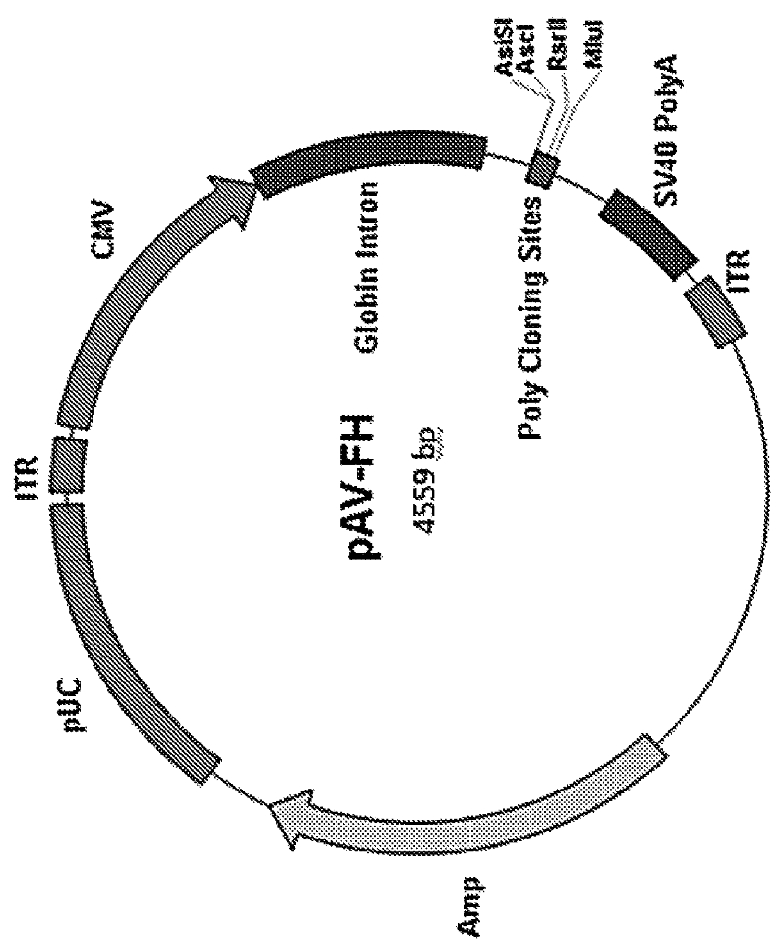
FIG. 7 is a plasmid map of a fifth embodiment of the construct of the invention, showing the features of SEQ ID NO: 17.

The purpose of this study was to compare the ability of the inventor's construct (MRX001, FIG. 3, SEQ ID NO: 13) expressing TH and GCH1 by the same promoter with a comparator based on the prior art construct expressing the two genes by separate promoters, to improve the step count in a rat model of Parkinson's disease, using the gold standard technique of the art.

Materials and Methods

The methods used in this example are described in detail in Cederfjall et al, Scientific Reports, 2013; 3: 2157. Therefore, this experiment represents a robust comparison with the closest prior art construct.

Female Sprague Dawley rats, weighing 200-250 g were used. All rats received unilateral 6-OHDA medial forebrain bundle lesions. Rats were tested for 3 and 4 week post-lesion amphetamine rotations to confirm adequate lesioning. Rats were allocated to the treatment groups to ensure that the magnitude of lesion effect was evenly distributed between the two groups. Rats received intrastriatal infusions of the reference vector (Promoter-GCH1-Promoter-TH) (n=8), the experimental vector (MRX) (n=8) or remained as lesion only controls ($n=_4$).

Each animal in each vector group received a total of 2×109 genome copies of vector in 5 ml of vehicle This was intended to be not to fully restore motor function i.e to be sufficiently high to show activity but not sufficient to achieve optimal results and leaves a clear window to demonstrate enhanced efficacy if present in the comparator. The injections were made at two sites with two 1.5 ml deposits in the ventral tract and two 1.0 ml deposits in the dorsal injection tract. The coordinates were: (1) AP: 11.0 mm; ML: −2.8 mm and DV: −4.5, −3.5 mm and (2) AP: 0.0 mm; ML: −4.0 mm and DV: −5.0, −4.0 mm with the tooth bar set to −2.4 mm. The AAV vector was injected at a speed of 0.4 ml/min and the needle was kept in place for 1 min after the ventral and 3 min after the dorsal deposit was delivered, before it was slowly retracted.

Stepping tests were performed according to the method described in Olsson et al. (Olsson, M., et al. Forelimb akinesia in the rat Parkinson model: differential effects of dopamine agonists and nigral transplants as assessed by a new stepping test. J Neurosci 15, 3863-3875 (1995). An investigator blinded to the group identities of the animals assessed forelimb use by holding the rat with two hands only allowing one forepaw to reach the table surface. The animal was then moved sideways over a defined distance at a constant speed over 4-5 sec. The investigator scored the numbers of adjusting side steps in the forehand direction twice on a testing day, and the average was calculated. The primary endpoint was prospectively defined as the difference in step count at week 4 post injection of vector.

Results

Figure 14:
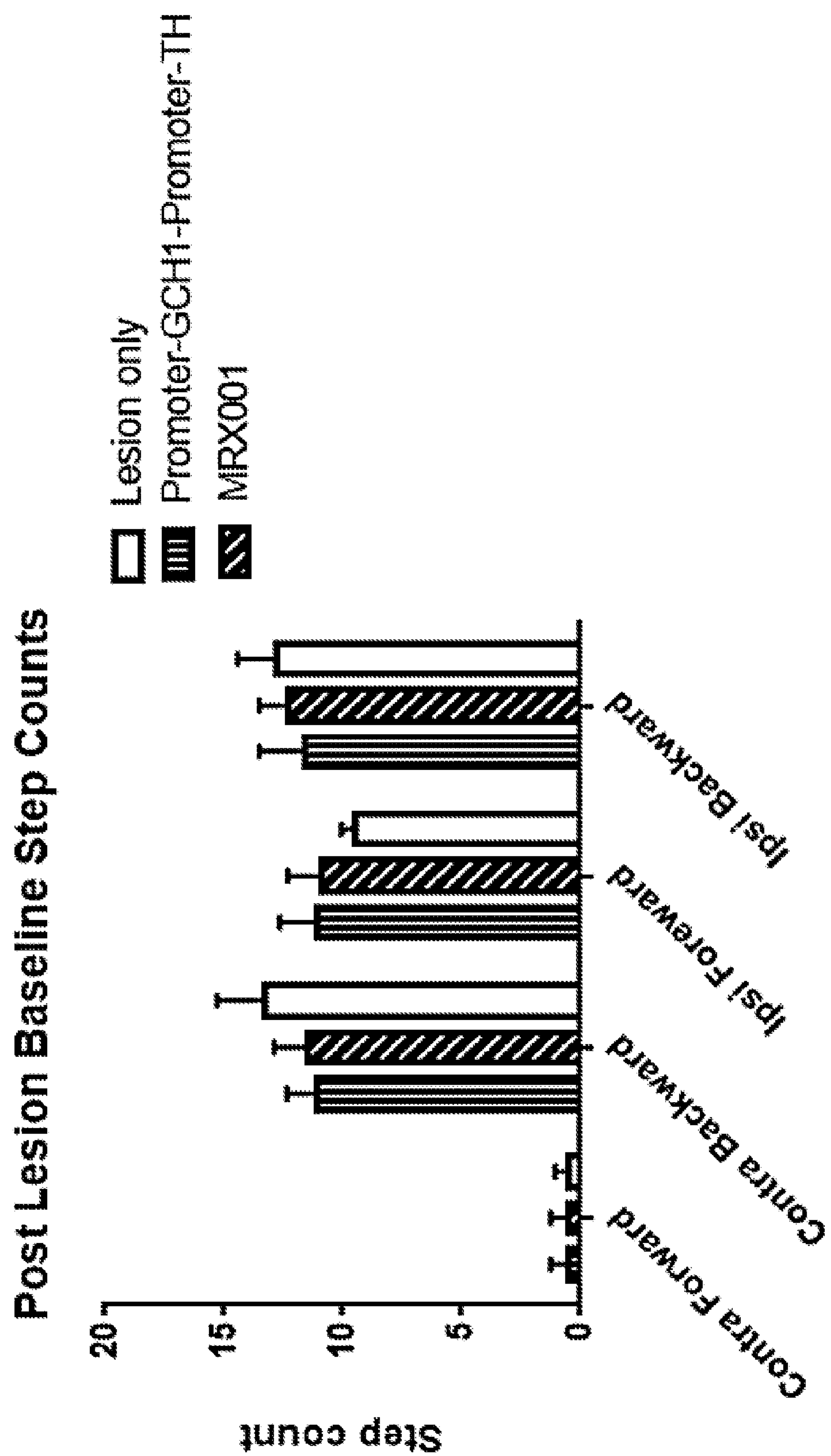
FIG. 14 is a graphical representation of the in vivo stepping assay control experiment showing baseline stepping in rats post-lesion.
Figure 15:
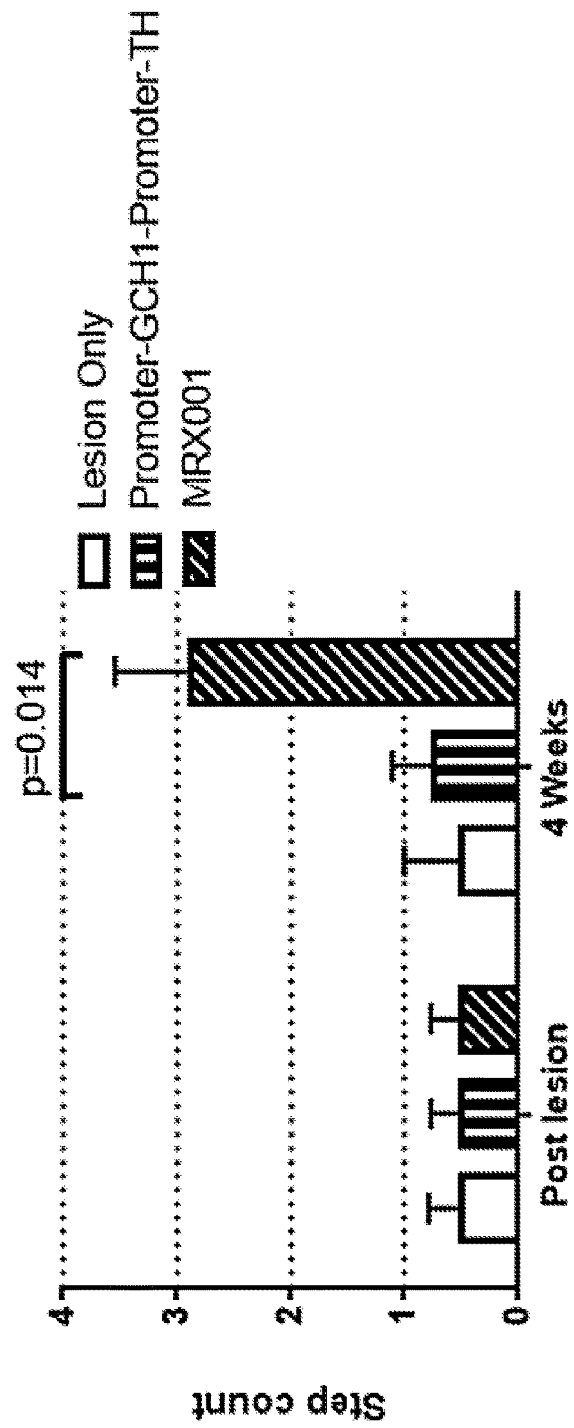
FIG. 15 is a graphical representation of the in vivo stepping assay showing a step count improvement in rats treated with a construct of the invention, when compared to a prior art construct, 4 weeks post treatment.

The results of this experiment are shown in FIGS. 14 and 15. Surprisingly, the inventor has found that the claimed construct is capable of partially restoring the step count in mice models of Parkinson's disease, whereas the prior art construct provides no such effect. This result demonstrates that the inventor's construct is significantly superior, and represents an important improvement in the art.

CONCLUSIONS

WO2013/061076 and WO2010/055209 (Oxford Biomedica) identified three proteins that were potentially effective in the treatment of Parkinson's disease, and all three proteins were regarded as being essential to provide a therapeutic effect. There is no discussion on the advantages of using a single promoter approach, as claimed, over a separate promoter approach. In fact, on page 3 in WO2013/06 1076, in the last line of the second paragraph, it is stated that: " . . . increased levels of L-DOPA and dopamine were not due to increases in protein expression from the fusion design vectors . . . ". Thus, these documents teach that, TH, GCH1 and AADC are required to produce a therapeutic effect. It is silent on the advantages or disadvantages of different promoter set-ups, as are all other relevant publications in relation to such constructs.

Cederfjall and Kirik (including WO2015/152813) moved the art forward to some extent by identifying that only two proteins were required to produce a therapeutic effect, these being TH and GCH1. However, the expression of these two genes is driven by separate promoters, and while WO2015/152813 suggests that this may be an effective means of expressing these genes for therapy, subsequently published work has proven that this approach is ineffective. The separate promoter approach surprisingly results in is sub-optimal expression when translated to results outside of that of murine studies. So much so that it failed to achieve complete reversal of motor symptoms in a primate model of Parkinson's disease. As a result of this defect, the corresponding product never went into full development, and Cederfjall et al. (Scientific reports; 3: 2157; 8 Jul. 2013) stated that "this problem requires a solution prior to the initiation of clinical trials utilizing this approach".

Surprisingly, and without wishing to be bound to any particular theory, the inventor has discovered that a separate promoter approach, as used in the prior art, results in random interference between the promoters, such that the expression of one or both genes is reduced to sub-therapeutic levels. This is not described in the any prior art document in the field, and would not have been considered by the skilled person looking to solve the problem of providing an improved TH and GCH1 expression construct.

The inventor has developed a novel construct for expression of TH and GCH1 (and not AADC), wherein expression of the two genes is driven by a single promoter. This results in significantly higher levels of expression than that of the construct of WO2015/152813. For example, the in vitro data provided in FIGS. 1 and 2 compare the expression levels of TH and GCH1 with that of the control construct which places the same promoter before each gene in the same manner as described WO2015/152813. This comparative data shows that the claimed invention displays surprisingly higher levels of expression of both TH and GCH1.

The in vivo experiments performed in a murine model (FIGS. 14 and 15) confirm the in vitro findings. The methods used in the inventor's in vivo experiments are the same as those disclosed in Cederfjall et al, 2013, the authors being the inventors of WO2015/152813. Therefore, this experiment represents a robust comparison with the closest prior art construct. The control construct places the same promoter before each gene in the same manner as described, in WO2015/152813. The inventor performed the experiments at titers that are sufficiently high to show activity, but not sufficient to achieve optimal results, thus leaving a clear window to demonstrate the enhanced efficacy.

Surprisingly, the inventor has found that the claimed construct is capable of restoring the step count in mice models of Parkinson's disease, whereas construct incorporating a promoter before each gene shows no effect. Moreover, it is particularly surprising that this bicistronic construct has been demonstrated by the inventor to be markedly more effective in vitro than a 1:1 mixture of equivalent tires of a monocistronic TH vector and a monocistronic GCH1 vector.

This result demonstrates that the inventor's construct is far superior, and represents a significant improvement in the art. The inventor's construct results in improved expression of TH and GH1 and this translates to an improved therapeutic effect, as evidenced by the in vitro and in vivo data provided herein.

SEQUENCE LISTING

<160> NUMBER OF SEQ ID NOS: 31

<210> SEQ ID NO 1
<211> LENGTH: 1494
<212> TYPE: DNA
<213> ORGANISM: Homo sapiens

<400> SEQUENCE: 1

```
atgcccaccc ccgacgccac cacgccacag gccaagggct tccgcagggc cgtgtctgag     60
ctggacgcca agcaggcaga ggccatcatg tccccgcggt tcattgggcg caggcagagc    120
ctcatcgagg acgcccgcaa ggagcgggag gcggcggtgg cagcagcggc cgctgcagtc    180
ccctcggagc ccggggaccc cctggaggct gtggcctttg aggagaagga ggggaaggcc    240
gtgctaaacc tgctcttctc cccgagggcc accaagccct cggcgctgtc ccgagctgtg    300
aaggtgtttg agacgtttga agccaaaatc caccatctag agacccggcc cgcccagagg    360
ccgcgagctg gggggcccca cctggagtac ttcgtgcgcc tcgaggtgcg ccgaggggac    420
ctggccgccc tgctcagtgg tgtgcgccag gtgtcagagg acgtgcgcag ccccgcgggg    480
cccaaggtcc cctggttccc aagaaaagtg tcagagctgg acaagtgtca tcacctggtc    540
accaagttcg accctgacct ggacttggac cacccgggct tctcggacca ggtgtaccgc    600
```

```
cagcgcagga agctgattgc tgagatcgcc ttccagtaca ggcacggcga cccgattccc    660

cgtgtggagt acaccgccga ggagattgcc acctggaagg aggtctacac cacgctgaag    720

ggcctctacg ccacgcacgc ctgcggggag cacctggagg cctttgcttt gctggagcgc    780

ttcagcggct accgggaaga caatatcccc cagctggagg acgtctcccg cttcctgaag    840

gagcgcacgg gcttccagct gcggcctgtg gccggcctgc tgtccgcccg ggacttcctg    900

gccagcctgg ccttccgcgt gttccagtgc acccagtata tccgccacgc gtcctcgccc    960

atgcactccc ctgagccgga ctgctgccac gagctgctgg ggcacgtgcc catgctggcc   1020

gaccgcacct tcgcgcagtt ctcgcaggac attggcctgg cgtccctggg ggcctcggat   1080

gaggaaattg agaagctgtc cacgctgtac tggttcacgg tggagttcgg gctgtgtaag   1140

cagaacgggg aggtgaaggc ctatggtgcc gggctgctgt cctcctacgg ggagctcctg   1200

cactgcctgt ctgaggagcc tgagattcgg gccttcgacc ctgaggctgc ggccgtgcag   1260

ccctaccaag accagacgta ccagtcagtc tacttcgtgt ctgagagctt cagtgacgcc   1320

aaggacaagc tcaggagcta tgcctcacgc atccagcgcc ccttctccgt gaagttcgac   1380

ccgtacacgc tggccatcga cgtgctggac agcccccagg ccgtgcggcg ctccctggag   1440

ggtgtccagg atgagctgga cacccttgcc catgcgctga gtgccattgg ctag         1494
```

```
<210> SEQ ID NO 2
<211> LENGTH: 1029
<212> TYPE: DNA
<213> ORGANISM: Homo sapiens

<400> SEQUENCE: 2

atgagccccg cggggcccaa ggtcccctgg ttcccaagaa aagtgtcaga gctggacaag     60

tgtcatcacc tggtcaccaa gttcgaccct gacctggact tggaccaccc gggcttctcg    120

gaccaggtgt accgccagcg caggaagctg attgctgaga tcgccttcca gtacaggcac    180

ggcgacccga ttccccgtgt ggagtacacc gccgaggaga ttgccacctg gaaggaggtc    240

tacaccacgc tgaagggcct ctacgccacg cacgcctgcg gggagcacct ggaggccttt    300

gctttgctgg agcgcttcag cggctaccgg gaagacaata tcccccagct ggaggacgtc    360

tcccgcttcc tgaaggagcg cacgggcttc cagctgcggc ctgtggccgg cctgctgtcc    420

gcccgggact tcctggccag cctggccttc cgcgtgttcc agtgcaccca gtatatccgc    480

cacgcgtcct cgcccatgca ctcccctgag ccggactgct gccacgagct gctggggcac    540

gtgcccatgc tggccgaccg caccttcgcg cagttctcgc aggacattgg cctggcgtcc    600

ctgggggcct cggatgagga aattgagaag ctgtccacgc tgtactggtt cacggtggag    660

ttcgggctgt gtaagcagaa cggggaggtg aaggcctatg gtgccgggct gctgtcctcc    720

tacggggagc tcctgcactg cctgtctgag gagcctgaga ttcgggcctt cgaccctgag    780

gctgcggccg tgcagcccta ccaagaccag acgtaccagt cagtctactt cgtgtctgag    840

agcttcagtg acgccaagga caagctcagg agctatgcct cacgcatcca gcgccccttc    900

tccgtgaagt tcgacccgta cacgctggcc atcgacgtgc tggacagccc ccaggccgtg    960

cggcgctccc tggagggtgt ccaggatgag ctggacaccc ttgcccatgc gctgagtgcc   1020

attggctag                                                           1029

<210> SEQ ID NO 3
<211> LENGTH: 792
<212> TYPE: DNA
```

<213> ORGANISM: Mus musculus

<400> SEQUENCE: 3

```
ggtggttttc ctttgaaaaa cacgatgata atatggccac aaccgcggcc gtagatcccg      60
ggaccatgga gaagccgcgg ggagtcaggt gcaccaatgg gttctccgag cgggagctgc     120
cgcggcccgg ggccagcccg cctgccgaga agtcccggcc gcccgaggcc aagggcgcac     180
agccggccga cgcctggaag gcagggcggc accgcagcga ggaggaaaac caggtgaacc     240
tccccaaact ggcggctgct tactcgtcca ttctgctctc gctgggcgag gacccccagc     300
ggcaggggct gctcaagacg ccctggaggg cggccaccgc catgcagtac ttcaccaagg     360
gataccagga gaccatctca gatgtcctga atgatgctat atttgatgaa gatcatgacg     420
agatggtgat tgtgaaggac atagatatgt tctccatgtg tgagcatcac cttgttccat     480
ttgtaggaag ggtccatatt ggctatcttc ctaacaagca agtccttggt ctcagtaaac     540
ttgccaggat tgtagaaatc tacagtagac gactacaagt tcaagagcgc ctcaccaaac     600
agattgcggt ggccatcaca gaagccttgc agcctgctgg cgttggagta gtgattgaag     660
cgacacacat gtgcatggta atgcgaggcg tgcagaaaat gaacagcaag actgtcacta     720
gcaccatgct gggcgtgttc cgggaagacc ccaagactcg ggaggagttc ctcacactaa     780
tcaggagctg ag                                                         792
```

<210> SEQ ID NO 4
<211> LENGTH: 753
<212> TYPE: DNA
<213> ORGANISM: Homo sapiens

<400> SEQUENCE: 4

```
atggagaagg gccctgtgcg ggcaccggcg gagaagccgc ggggcgccag gtgcagcaat      60
gggttccccg agcgggatcc gccgcggccc gggcccagca ggccggcgga gaagcccccg     120
cggcccgagg ccaagagcgc gcagcccgcg gacggctgga agggcgagcg gccccgcagc     180
gaggaggata acgagctgaa cctccctaac ctggcagccg cctactcgtc catcctgagc     240
tcgctgggcg agaaccccca gcggcaaggg ctgctcaaga cgccctggag ggcggcctcg     300
gccatgcagt tcttcaccaa gggctaccag gagaccatct cagatgtcct aaacgatgct     360
atatttgatg aagatcatga tgagatggtg attgtgaagg acatagacat gttttccatg     420
tgtgagcatc acttggttcc atttgttgga aaggtccata ttggttatct tcctaacaag     480
caagtccttg gcctcagcaa acttgcgagg attgtagaaa tctatagtag aagactacaa     540
gttcaggagc gccttacaaa acaaattgct gtagcaatca cggaagcctt gcggcctgct     600
ggagtcgggg tagtggttga agcaacacac atgtgtatgg taatgcgagg tgtacagaaa     660
atgaacagca aaactgtgac cagcacaatg ttgggtgtgt tccgggagga tccaaagact     720
cgggaagagt tcctgactct cattaggagc tga                                  753
```

<210> SEQ ID NO 5
<211> LENGTH: 469
<212> TYPE: DNA
<213> ORGANISM: Homo sapiens

<400> SEQUENCE: 5

```
ctgcagaggg ccctgcgtat gagtgcaagt gggttttagg accaggatga ggcggggtgg      60
gggtgcctac ctgacgaccg accccgaccc actggacaag cacccaaccc ccattcccca     120
aattgcgcat cccctatcag agagggggag gggaaacagg atgcggcgag gcgcgtgcgc     180
```

```
actgccagct tcagcaccgc ggacagtgcc ttcgccccg cctggcggcg cgcgccaccg    240

ccgcctcagc actgaaggcg cgctgacgtc actcgccggt cccccgcaaa ctccccttcc    300

cggccacctt ggtcgcgtcc gcgccgccgc cggcccagcc ggaccgcacc acgcgaggcg    360

cgagataggg gggcacgggc gcgaccatct gcgctgcggc gccggcgact cagcgctgcc    420

tcagtctgcg gtgggcagcg gaggagtcgt gtcgtgcctg agagcgcag                469


<210> SEQ ID NO 6
<211> LENGTH: 461
<212> TYPE: DNA
<213> ORGANISM: Foot-and-mouth disease virus

<400> SEQUENCE: 6

agcaggtttc cccaactgac acaaaacgtg caacttgaaa ctccgcctgg tctttccagg     60

tctagagggg taacactttg tactgcgttt ggctccacgc tcgatccact ggcgagtgtt    120

agtaacagca ctgttgcttc gtagcggagc atgacggccg tgggaactcc tccttggtaa    180

caaggaccca cggggccaaa agccacgccc acacgggccc gtcatgtgtg caaccccagc    240

acggcgactt tactgcgaaa cccactttaa agtgacattg aaactggtac ccacacactg    300

gtgacaggct aaggatgccc ttcaggtacc ccgaggtaac acgcgacact cgggatctga    360

gaaggggact ggggcttcta taaaagcgct cggtttaaaa agcttctatg cctgaatagg    420

tgaccggagg tcggcacctt tcctttgcaa ttactgacca c                        461


<210> SEQ ID NO 7
<211> LENGTH: 551
<212> TYPE: DNA
<213> ORGANISM: Encephalomyocarditis virus

<400> SEQUENCE: 7

cgttactggc cgaagccgct tggaataagg ccggtgtgcg tttgtctata tgttattttc     60

caccatattg ccgtcttttg gcaatgtgag ggcccggaaa cctggccctg tcttcttgac    120

gagcattcct aggggtcttt cccctctcgc caaaggaatg caaggtctgt tgaatgtcgt    180

gaaggaagca gttcctctgg aagcttcttg aagacaaaca acgtctgtag cgaccctttg    240

caggcagcgg aaccccccac ctggcgacag gtgcctctgc ggccaaaagc cacgtgtata    300

agatacacct gcaaaggcgg cacaacccca gtgccacgtt gtgagttgga tagttgtgga    360

aagagtcaaa tggctcccct caagcgtatt caacaagggg ctgaaggatg cccagaaggt    420

accccattgt atgggatctg atctggggcc tcggtgcaca tgcttttcat gtgtttagtc    480

gaggttaaaa aacgtctagg ccccccgaac cacggggacg tggttttcct ttgaaaaaca    540

cgatgataat a                                                         551


<210> SEQ ID NO 8
<211> LENGTH: 84
<212> TYPE: DNA
<213> ORGANISM: Unknown
<220> FEATURE:
<223> OTHER INFORMATION: Viral 2A peptide spacer sequence

<400> SEQUENCE: 8

cgcgcgaaac gcgcgccggt gaaacagacc ctgaactttg atctgctgaa actggcgggc     60

gatgtggaaa gcaacccggg cccg                                            84


<210> SEQ ID NO 9
```

<211> LENGTH: 45
<212> TYPE: DNA
<213> ORGANISM: Unknown
<220> FEATURE:
<223> OTHER INFORMATION: Flexible linker sequence.

<400> SEQUENCE: 9
ggaggtggcg ggtccggggg cgggggtagc ggtggcgggg gctcc 45

<210> SEQ ID NO 10
<211> LENGTH: 592
<212> TYPE: DNA
<213> ORGANISM: Woodchuck hepatitis virus

<400> SEQUENCE: 10
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tg 592

<210> SEQ ID NO 11
<211> LENGTH: 247
<212> TYPE: DNA
<213> ORGANISM: Woodchuck hepatitis virus

<400> SEQUENCE: 11
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttag ttcttgccac ggcggaactc 180
atcgccgcct gccttgcccg ctgctggaca ggggctcggc tgttgggcac tgacaattcc 240
gtggtgt 247

<210> SEQ ID NO 12
<211> LENGTH: 224
<212> TYPE: DNA
<213> ORGANISM: Simian virus 40

<400> SEQUENCE: 12
agcagacatg ataagataca ttgatgagtt tggacaaacc acaactagaa tgcagtgaaa 60
aaaatgcttt atttgtgaaa tttgtgatgc tattgcttta tttgtaacca ttataagctg 120
caataaacaa gttaacaaca acaattgcat tcattttatg tttcaggttc agggggaggt 180
gtgggaggtt ttttaaagca agtaaaacct ctacaaatgt ggta 224

<210> SEQ ID NO 13
<211> LENGTH: 6633
<212> TYPE: DNA
<213> ORGANISM: Unknown
<220> FEATURE:
<223> OTHER INFORMATION: An embodiemnt of the AAAV1 vector of the invention, which includes a CMV promoter, a CMV enchancer, an EMCV IRES, and a SV40 poly A tail.

<400> SEQUENCE: 13

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccggtc gcgtactagt aatcaattac ggggtcatta gttcatagcc    180
catatatgga gttccgcgtt acataactta cggtaaatgg cccgcctggc tgaccgccca    240
acgacccccg cccattgacg tcaataatga cgtatgttcc catagtaacg ccaataggga    300
ctttccattg acgtcaatgg gtggagtatt tacggtaaac tgcccacttg gcagtacatc    360
aagtgtatca tatgccaagt acgcccccta ttgacgtcaa tgacggtaaa tggcccgcct    420
ggcattatgc ccagtacatg accttatggg actttcctac ttggcagtac atctacgtat    480
tagtcatcgc tattaccatg ctgatgcggt tttggcagta catcaatggg cgtggatagc    540
ggtttgactc acggggattt ccaagtctcc accccattga cgtcaatggg agtttgtttt    600
ggcaccaaaa tcaacgggac tttccaaaat gtcgtaacaa ctccgcccca ttgacgcaaa    660
tgggcggtag gcgtgtacgg tgggaggtct atataagcag agctggttta gtgaaccgtc    720
agatcagatc tttgtcgatc ctaccatcca ctcgacacac ccgccagcgg ccgctgccaa    780
gcttccgagc tctcgaattc aaaggaggta cccaccatgg ccaccatgag ccccgcgggg    840
cccaaggtcc cctggttccc aagaaaagtg tcagagctgg acaagtgtca tcacctggtc    900
accaagttcg accctgacct ggacttggac cacccgggct tctcggacca ggtgtaccgc    960
cagcgcagga agctgattgc tgagatcgcc ttccagtaca ggcacggcga cccgattccc   1020
cgtgtggagt acaccgccga ggagattgcc acctggaagg aggtctacac cacgctgaag   1080
ggcctctacg ccacgcacgc ctgcggggag cacctggagg cctttgcttt gctggagcgc   1140
ttcagcggct accgggaaga caatatcccc cagctggagg acgtctcccg cttcctgaag   1200
gagcgcacgg gcttccagct gcggcctgtg gccggcctgc tgtccgcccg ggacttcctg   1260
gccagcctgg ccttccgcgt gttccagtgc acccagtata tccgccacgc gtcctcgccc   1320
atgcactccc ctgagccgga ctgctgccac gagctgctgg ggcacgtgcc catgctggcc   1380
gaccgcacct tcgcgcagtt ctcgcaggac attggcctgg cgtccctggg ggcctcggat   1440
gaggaaattg agaagctgtc cacgctgtac tggttcacgg tggagttcgg gctgtgtaag   1500
cagaacgggg aggtgaaggc ctatggtgcc gggctgctgt cctcctacgg ggagctcctg   1560
cactgcctgt ctgaggagcc tgagattcgg gccttcgacc ctgaggctgc ggccgtgcag   1620
ccctaccaag accagacgta ccagtcagtc tacttcgtgt ctgagagctt cagtgacgcc   1680
aaggacaagc tcaggagcta tgcctcacgc atccagcgcc ccttctccgt gaagttcgac   1740
ccgtacacgc tggccatcga cgtgctggac agcccccagg ccgtgcggcg ctccctggag   1800
ggtgtccagg atgagctgga cacccttgcc catgcgctga gtgccattgg ctaaacgtta   1860
ctggccgaag ccgcttggaa taaggccggt gtgcgtttgt ctatatgtta ttttccacca   1920
tattgccgtc ttttggcaat gtgagggccc ggaaacctgg ccctgtcttc ttgacgagca   1980
ttcctagggg tctttcccct ctcgccaaag gaatgcaagg tctgttgaat gtcgtgaagg   2040
aagcagttcc tctggaagct tcttgaagac aaacaacgtc tgtagcgacc ctttgcaggc   2100
agcggaaccc cccacctggc gacaggtgcc tctgcggcca aaagccacgt gtataagata   2160
cacctgcaaa ggcggcacaa ccccagtgcc acgttgtgag ttggatagtt gtggaaagag   2220
```

-continued

```
tcaaatggct cccctcaagc gtattcaaca aggggctgaa ggatgcccag aaggtacccc   2280

attgtatggg atctgatctg gggcctcggt gcacatgctt ttcatgtgtt tagtcgaggt   2340

taaaaaacgt ctaggccccc cgaaccacgg ggacgtggtt ttcctttgaa aaacacgatg   2400

ataatagcca ccatggagaa gggccctgtg cgggcaccgg cggagaagcc gcggggcgcc   2460

aggtgcagca atgggttccc cgagcgggat ccgccgcggc ccgggcccag caggccggcg   2520

gagaagcccc cgcggcccga ggccaagagc gcgcagcccg cggacggctg gaagggcgag   2580

cggccccgca gcgaggagga taacgagctg aacctcccta acctggcagc cgcctactcg   2640

tccatcctga gctcgctggg cgagaacccc cagcggcaag ggctgctcaa gacgccctgg   2700

agggcggcct cggccatgca gttcttcacc aagggctacc aggagaccat ctcagatgtc   2760

ctaaacgatg ctatatttga tgaagatcat gatgagatgg tgattgtgaa ggacatagac   2820

atgttttcca tgtgtgagca tcacttggtt ccatttgttg gaaaggtcca tattggttat   2880

cttcctaaca agcaagtcct tggcctcagc aaacttgcga ggattgtaga aatctatagt   2940

agaagactac aagttcagga gcgccttaca aaacaaattg ctgtagcaat cacggaagcc   3000

ttgcggcctg ctggagtcgg ggtagtggtt gaagcaacac acatgtgtat ggtaatgcga   3060

ggtgtacaga aaatgaacag caaaactgtg accagcacaa tgttgggtgt gttccgggag   3120

gatccaaaga ctcgggaaga gttcctgact ctcattagga gctgagccac ctaatcaacc   3180

tctggattac aaaatttgtg aaagattgac tggtattctt aactatgttg ctccttttac   3240

gctatgtgga tacgctgctt taatgccttt gtatcatgct attgcttccc gtatggcttt   3300

cattttctcc tccttgtata aatcctggtt gctgtctctt tatgaggagt tgtggcccgt   3360

tgtcaggcaa cgtggcgtgg tgtgcactgt gtttgctgac gcaaccccca ctggttgggg   3420

cattgccacc acctgtcagc tcctttccgg gactttcgct ttccccctcc ctattgccac   3480

ggcggaactc atcgccgcct gccttgcccg ctgctggaca ggggctcggc tgttgggcac   3540

tgacaattcc gtggtgttgt cggggaaatc atcgtccttt ccctggctga ctgatacaat   3600

cgatttctgg atccgcaggc ctctgctagc ttgactgact gagatacagc gtaccttcag   3660

ctcacagaca tgataagata cattgatgag tttggacaaa ccacaactag aatgcagtga   3720

aaaaaatgct ttatttgtga aatttgtgat gctattgctt tatttgtaac cattataagc   3780

tgcaataaac aagttaacaa caacaattgc attcatttta tgtttcaggt tcagggggag   3840

gtgtgggagg tttttttaagc ttaacgcggt aaccacgtgc ggacccaacg gccgcaggaa   3900

cccctagtga tggagttggc cactccctct ctgcgcgctc gctcgctcac tgaggccggg   3960

cgaccaaagg tcgcccgacg cccgggcttt gcccgggcgg cctcagtgag cgagcgagcg   4020

cgcagctgcc tgcaggggcg cctgatgcgg tattttctcc ttacgcatct gtgcggtatt   4080

tcacaccgca tacgtcaaag caaccatagt acgcgccctg tagcggcgca ttaagcgcgg   4140

cgggtgtggt ggttacgcgc agcgtgaccg ctacacttgc cagcgcccta gcgcccgctc   4200

ctttcgcttt cttcccttcc tttctcgcca cgttcgccgg ctttccccgt caagctctaa   4260

atcgggggct ccctttaggg ttccgattta gtgctttacg gcacctcgac cccaaaaaac   4320

ttgatttggg tgatggttca cgtagtgggc catcgccctg atagacggtt tttcgccctt   4380

tgacgttgga gtccacgttc tttaatagtg gactcttgtt ccaaactgga acaacactca   4440

accctatctc gggctattct tttgatttat aagggatttt gccgatttcg gcctattggt   4500

taaaaaatga gctgatttaa caaaaattta acgcgaattt taacaaaata ttaacgttta   4560

caattttatg gtgcactctc agtacaatct gctctgatgc cgcatagtta agccagcccc   4620
```

```
gacacccgcc aacacccgct gacgcgccct gacgggcttg tctgctcccg gcatccgctt   4680

acagacaagc tgtgaccgtc tccgggagct gcatgtgtca gaggttttca ccgtcatcac   4740

cgaaacgcgc gagacgaaag ggcctcgtga tacgcctatt tttataggtt aatgtcatga   4800

taataatggt ttcttagacg tcaggtggca cttttcgggg aaatgtgcgc ggaaccccta   4860

tttgtttatt tttctaaata cattcaaata tgtatccgct catgagacaa taaccctgat   4920

aaatgcttca ataatattga aaaaggaaga gtatgagtat tcaacatttc cgtgtcgccc   4980

ttattccctt ttttgcggca ttttgccttc ctgtttttgc tcacccagaa acgctggtga   5040

aagtaaaaga tgctgaagat cagttgggtg cacgagtggg ttacatcgaa ctggatctca   5100

acagcggtaa gatccttgag agttttcgcc ccgaagaacg ttttccaatg atgagcactt   5160

ttaaagttct gctatgtggc gcggtattat cccgtattga cgccgggcaa gagcaactcg   5220

gtcgccgcat acactattct cagaatgact tggttgagta ctcaccagtc acagaaaagc   5280

atcttacgga tggcatgaca gtaagagaat tatgcagtgc tgccataacc atgagtgata   5340

acactgcggc caacttactt ctgacaacga tcggaggacc gaaggagcta accgcttttt   5400

tgcacaacat gggggatcat gtaactcgcc ttgatcgttg ggaaccggag ctgaatgaag   5460

ccataccaaa cgacgagcgt gacaccacga tgcctgtagc aatggcaaca acgttgcgca   5520

aactattaac tggcgaacta cttactctag cttcccggca acaattaata gactggatgg   5580

aggcggataa agttgcagga ccacttctgc gctcggccct tccggctggc tggtttattg   5640

ctgataaatc tggagccggt gagcgtgggt ctcgcggtat cattgcagca ctggggccag   5700

atggtaagcc ctcccgtatc gtagttatct acacgacggg gagtcaggca actatggatg   5760

aacgaaatag acagatcgct gagataggtg cctcactgat taagcattgg taactgtcag   5820

accaagttta ctcatatata ctttagattg atttaaaact tcatttttaa tttaaaagga   5880

tctaggtgaa gatccttttt gataatctca tgaccaaaat cccttaacgt gagttttcgt   5940

tccactgagc gtcagacccc gtagaaaaga tcaaaggatc ttcttgagat cctttttttc   6000

tgcgcgtaat ctgctgcttg caaacaaaaa aaccaccgct accagcggtg gtttgtttgc   6060

cggatcaaga gctaccaact ctttttccga aggtaactgg cttcagcaga gcgcagatac   6120

caaatactgt ccttctagtg tagccgtagt taggccacca cttcaagaac tctgtagcac   6180

cgcctacata cctcgctctg ctaatcctgt taccagtggc tgctgccagt ggcgataagt   6240

cgtgtcttac cgggttggac tcaagacgat agttaccgga taaggcgcag cggtcgggct   6300

gaacgggggg ttcgtgcaca cagcccagct tggagcgaac gacctacacc gaactgagat   6360

acctacagcg tgagctatga gaaagcgcca cgcttcccga agggagaaag gcggacaggt   6420

atccggtaag cggcagggtc ggaacaggag agcgcacgag ggagcttcca gggggaaacg   6480

cctggtatct ttatagtcct gtcgggtttc gccacctctg acttgagcgt cgatttttgt   6540

gatgctcgtc aggggggcgg agcctatgga aaaacgccag caacgcggcc tttttacggt   6600

tcctggcctt ttgctggcct tttgctcaca tgt                                 6633
```

<210> SEQ ID NO 14
<211> LENGTH: 6542
<212> TYPE: DNA
<213> ORGANISM: Unknown
<220> FEATURE:
<223> OTHER INFORMATION: An example of a AAAV1 vector of the invention. This vector similar to SEQ ID NO: 13, but this particular embodiment includes an FMDV IRES instead of the EMCV IRES.

<400> SEQUENCE: 14

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccggtc gcgtactagt aatcaattac ggggtcatta gttcatagcc    180
catatatgga gttccgcgtt acataactta cggtaaatgg cccgcctggc tgaccgccca    240
acgacccccg cccattgacg tcaataatga cgtatgttcc catagtaacg ccaataggga    300
ctttccattg acgtcaatgg gtggagtatt tacggtaaac tgcccacttg gcagtacatc    360
aagtgtatca tatgccaagt acgcccccta ttgacgtcaa tgacggtaaa tggcccgcct    420
ggcattatgc ccagtacatg accttatggg actttcctac ttggcagtac atctacgtat    480
tagtcatcgc tattaccatg ctgatgcggt tttggcagta catcaatggg cgtggatagc    540
ggtttgactc acggggattt ccaagtctcc accccattga cgtcaatggg agtttgtttt    600
ggcaccaaaa tcaacgggac tttccaaaat gtcgtaacaa ctccgcccca ttgacgcaaa    660
tgggcggtag gcgtgtacgg tgggaggtct atataagcag agctggttta gtgaaccgtc    720
agatcagatc tttgtcgatc ctaccatcca ctcgacacac ccgccagcgg ccgctgccaa    780
gcttccgagc tctcgaattc aaaggaggta cccaccatgg ccaccatgag ccccgcgggg    840
cccaaggtcc cctggttccc aagaaaagtg tcagagctgg acaagtgtca tcacctggtc    900
accaagttcg accctgacct ggacttggac cacccgggct tctcggacca ggtgtaccgc    960
cagcgcagga agctgattgc tgagatcgcc ttccagtaca ggcacggcga cccgattccc   1020
cgtgtggagt acaccgccga ggagattgcc acctggaagg aggtctacac cacgctgaag   1080
ggcctctacg ccacgcacgc ctgcggggag cacctggagg cctttgcttt gctggagcgc   1140
ttcagcggct accgggaaga caatatcccc cagctggagg acgtctcccg cttcctgaag   1200
gagcgcacgg gcttccagct gcggcctgtg gccggcctgc tgtccgcccg ggacttcctg   1260
gccagcctgg ccttccgcgt gttccagtgc acccagtata tccgccacgc gtcctcgccc   1320
atgcactccc ctgagccgga ctgctgccac gagctgctgg ggcacgtgcc catgctggcc   1380
gaccgcacct tcgcgcagtt ctcgcaggac attggcctgg cgtccctggg ggcctcggat   1440
gaggaaattg agaagctgtc cacgctgtac tggttcacgg tggagttcgg gctgtgtaag   1500
cagaacgggg aggtgaaggc ctatggtgcc gggctgctgt cctcctacgg ggagctcctg   1560
cactgcctgt ctgaggagcc tgagattcgg gccttcgacc ctgaggctgc ggccgtgcag   1620
ccctaccaag accagacgta ccagtcagtc tacttcgtgt ctgagagctt cagtgacgcc   1680
aaggacaagc tcaggagcta tgcctcacgc atccagcgcc ccttctccgt gaagttcgac   1740
ccgtacacgc tggccatcga cgtgctggac agcccccagg ccgtgcggcg ctccctggag   1800
ggtgtccagg atgagctgga cacccttgcc catgcgctga gtgccattgg ctaaagcagg   1860
tttccccaac tgacacaaaa cgtgcaactt gaaactccgc ctggtctttc caggtctaga   1920
ggggtaacac tttgtactgc gtttggctcc acgctcgatc cactggcgag tgttagtaac   1980
agcactgttg cttcgtagcg gagcatgacg gccgtgggaa ctcctccttg gtaacaagga   2040
cccacggggc caaaagccac gcccacacgg gcccgtcatg tgtgcaaccc cagcacggcg   2100
actttactgc gaaacccact ttaaagtgac attgaaactg gtacccacac actggtgaca   2160
ggctaaggat gcccttcagg taccccgagg taacacgcga cactcgggat ctgagaaggg   2220
gactggggct tctataaaag cgctcggttt aaaaagcttc tatgcctgaa taggtgaccg   2280
gaggtcggca cctttccttt gcaattactg accacgccac catggagaag ggccctgtgc   2340
```

```
gggcaccggc ggagaagccg cggggcgcca ggtgcagcaa tgggttcccc gagcgggatc   2400
cgccgcggcc cgggcccagc aggccggcgg agaagccccc gcggcccgag gccaagagcg   2460
cgcagcccgc ggacggctgg aagggcgagc ggccccgcag cgaggaggat aacgagctga   2520
acctccctaa cctggcagcc gcctactcgt ccatcctgag ctcgctgggc gagaaccccc   2580
agcggcaagg gctgctcaag acgccctgga gggcggcctc ggccatgcag ttcttcacca   2640
agggctacca ggagaccatc tcagatgtcc taaacgatgc tatatttgat gaagatcatg   2700
atgagatggt gattgtgaag gacatagaca tgttttccat gtgtgagcat cacttggttc   2760
catttgttgg aaaggtccat attggttatc ttcctaacaa gcaagtcctt ggcctcagca   2820
aacttgcgag gattgtagaa atctatagta gaagactaca agttcaggag cgccttacaa   2880
aacaaattgc tgtagcaatc acggaagcct tgcggcctgc tggagtcggg gtagtggttg   2940
aagcaacaca catgtgtatg gtaatgcgag gtgtacagaa aatgaacagc aaaactgtga   3000
ccagcacaat gttgggtgtg ttccgggagg atccaaagac tcgggaagag ttcctgactc   3060
tcattaggag ctgagccacc taatcaacct ctggattaca aaatttgtga aagattgact   3120
ggtattctta actatgttgc tccttttacg ctatgtggat acgctgcttt aatgcctttg   3180
tatcatgcta ttgcttcccg tatggctttc attttctcct ccttgtataa atcctggttg   3240
ctgtctcttt atgaggagtt gtggcccgtt gtcaggcaac gtggcgtggt gtgcactgtg   3300
tttgctgacg caacccccac tggttggggc attgccacca cctgtcagct cctttccggg   3360
actttcgctt tccccctccc tattgccacg gcggaactca tcgccgcctg ccttgcccgc   3420
tgctggacag gggctcggct gttgggcact gacaattccg tggtgttgtc ggggaaatca   3480
tcgtcctttc cctggctgac tgatacaatc gatttctgga tccgcaggcc tctgctagct   3540
tgactgactg agatacagcg taccttcagc tcacagacat gataagatac attgatgagt   3600
ttggacaaac cacaactaga atgcagtgaa aaaaatgctt tatttgtgaa atttgtgatg   3660
ctattgcttt atttgtaacc attataagct gcaataaaca agttaacaac aacaattgca   3720
ttcattttat gtttcaggtt cagggggagg tgtgggaggt tttttaagct taacgcggta   3780
accacgtgcg gacccaacgg ccgcaggaac ccctagtgat ggagttggcc actccctctc   3840
tgcgcgctcg ctcgctcact gaggccgggc gaccaaaggt cgcccgacgc ccgggctttg   3900
cccgggcggc ctcagtgagc gagcgagcgc gcagctgcct gcaggggcgc ctgatgcggt   3960
attttctcct tacgcatctg tgcggtattt cacaccgcat acgtcaaagc aaccatagta   4020
cgcgccctgt agcggcgcat taagcgcggc gggtgtggtg gttacgcgca gcgtgaccgc   4080
tacacttgcc agcgccctag cgcccgctcc tttcgctttc ttcccttcct ttctcgccac   4140
gttcgccggc tttccccgtc aagctctaaa tcgggggctc cctttagggt tccgatttag   4200
tgctttacgg cacctcgacc ccaaaaaact tgatttgggt gatggttcac gtagtgggcc   4260
atcgccctga tagacggttt ttcgcccttt gacgttggag tccacgttct ttaatagtgg   4320
actcttgttc caaactggaa caacactcaa ccctatctcg ggctattctt ttgatttata   4380
agggattttg ccgatttcgg cctattggtt aaaaaatgag ctgatttaac aaaaatttaa   4440
cgcgaatttt aacaaaatat taacgtttac aattttatgg tgcactctca gtacaatctg   4500
ctctgatgcc gcatagttaa gccagccccg acacccgcca acacccgctg acgcgccctg   4560
acgggcttgt ctgctcccgg catccgctta cagacaagct gtgaccgtct ccgggagctg   4620
catgtgtcag aggttttcac cgtcatcacc gaaacgcgcg agacgaaagg gcctcgtgat   4680
```

```
acgcctattt ttataggtta atgtcatgat aataatggtt tcttagacgt caggtggcac   4740

ttttcgggga aatgtgcgcg gaacccctat ttgtttattt ttctaaatac attcaaatat   4800

gtatccgctc atgagacaat aaccctgata aatgcttcaa taatattgaa aaaggaagag   4860

tatgagtatt caacatttcc gtgtcgccct tattcccttt tttgcggcat tttgccttcc   4920

tgtttttgct cacccagaaa cgctggtgaa agtaaaagat gctgaagatc agttgggtgc   4980

acgagtgggt tacatcgaac tggatctcaa cagcggtaag atccttgaga gttttcgccc   5040

cgaagaacgt tttccaatga tgagcacttt taaagttctg ctatgtggcg cggtattatc   5100

ccgtattgac gccgggcaag agcaactcgg tcgccgcata cactattctc agaatgactt   5160

ggttgagtac tcaccagtca cagaaaagca tcttacggat ggcatgacag taagagaatt   5220

atgcagtgct gccataacca tgagtgataa cactgcggcc aacttacttc tgacaacgat   5280

cggaggaccg aaggagctaa ccgctttttt gcacaacatg ggggatcatg taactcgcct   5340

tgatcgttgg gaaccggagc tgaatgaagc cataccaaac gacgagcgtg acaccacgat   5400

gcctgtagca atggcaacaa cgttgcgcaa actattaact ggcgaactac ttactctagc   5460

ttcccggcaa caattaatag actggatgga ggcggataaa gttgcaggac cacttctgcg   5520

ctcggccctt ccggctggct ggtttattgc tgataaatct ggagccggtg agcgtgggtc   5580

tcgcggtatc attgcagcac tggggccaga tggtaagccc tcccgtatcg tagttatcta   5640

cacgacgggg agtcaggcaa ctatggatga acgaaataga cagatcgctg agataggtgc   5700

ctcactgatt aagcattggt aactgtcaga ccaagtttac tcatatatac tttagattga   5760

tttaaaactt catttttaat ttaaaaggat ctaggtgaag atcctttttg ataatctcat   5820

gaccaaaatc ccttaacgtg agttttcgtt ccactgagcg tcagaccccg tagaaaagat   5880

caaaggatct tcttgagatc cttttttct gcgcgtaatc tgctgcttgc aaacaaaaaa    5940

accaccgcta ccagcggtgg tttgtttgcc ggatcaagag ctaccaactc tttttccgaa   6000

ggtaactggc ttcagcagag cgcagatacc aaatactgtc cttctagtgt agccgtagtt   6060

aggccaccac ttcaagaact ctgtagcacc gcctacatac ctcgctctgc taatcctgtt   6120

accagtggct gctgccagtg gcgataagtc gtgtcttacc gggttggact caagacgata   6180

gttaccggat aaggcgcagc ggtcgggctg aacggggggt tcgtgcacac agcccagctt   6240

ggagcgaacg acctacaccg aactgagata cctacagcgt gagctatgag aaagcgccac   6300

gcttcccgaa gggagaaagg cggacaggta tccggtaagc ggcagggtcg gaacaggaga   6360

gcgcacgagg gagcttccag ggggaaacgc ctggtatctt tatagtcctg tcgggtttcg   6420

ccacctctga cttgagcgtc gatttttgtg atgctcgtca ggggggcgga gcctatggaa   6480

aaacgccagc aacgcggcct ttttacggtt cctggccttt tgctggcctt ttgctcacat   6540

gt                                                                  6542
```

```
<210> SEQ ID NO 15
<211> LENGTH: 6165
<212> TYPE: DNA
<213> ORGANISM: Unknown
<220> FEATURE:
<223> OTHER INFORMATION: An example of an AAAV1 vector of the invention.
      This is similar to SEQ ID NO: 13, but this particular embodiment
      includes a Furin cleavage site and a viral 2A peptide spacer,
      instead of the EMCV IRES

<400> SEQUENCE: 15

cctgcaggca gctgcgcgct cgctcgctca ctgaggccgc ccgggcgtcg ggcgaccttt     60
```

-continued

```
ggtcgcccgg cctcagtgag cgagcgagcg cgcagagagg gagtggccaa ctccatcact    120
aggggttcct gcggccggtc gcgtactagt aatcaattac ggggtcatta gttcatagcc    180
catatatgga gttccgcgtt acataactta cggtaaatgg cccgcctggc tgaccgccca    240
acgacccccg cccattgacg tcaataatga cgtatgttcc catagtaacg ccaataggga    300
ctttccattg acgtcaatgg gtggagtatt tacggtaaac tgcccacttg gcagtacatc    360
aagtgtatca tatgccaagt acgcccccta ttgacgtcaa tgacggtaaa tggcccgcct    420
ggcattatgc ccagtacatg accttatggg actttcctac ttggcagtac atctacgtat    480
tagtcatcgc tattaccatg ctgatgcggt tttggcagta catcaatggg cgtggatagc    540
ggtttgactc acggggattt ccaagtctcc accccattga cgtcaatggg agtttgtttt    600
ggcaccaaaa tcaacgggac tttccaaaat gtcgtaacaa ctccgcccca ttgacgcaaa    660
tgggcggtag gcgtgtacgg tgggaggtct atataagcag agctggttta gtgaaccgtc    720
agatcagatc tttgtcgatc ctaccatcca ctcgacacac ccgccagcgg ccgctgccaa    780
gcttccgagc tctcgaattc aaaggaggta cccaccatgg ccaccatgag ccccgcgggg    840
cccaaggtcc cctggttccc aagaaaagtg tcagagctgg acaagtgtca tcacctggtc    900
accaagttcg accctgacct ggacttggac cacccgggct tctcggacca ggtgtaccgc    960
cagcgcagga agctgattgc tgagatcgcc ttccagtaca ggcacggcga cccgattccc   1020
cgtgtggagt acaccgccga ggagattgcc acctggaagg aggtctacac cacgctgaag   1080
ggcctctacg ccacgcacgc ctgcggggag cacctggagg cctttgcttt gctggagcgc   1140
ttcagcggct accgggaaga caatatcccc cagctggagg acgtctcccg cttcctgaag   1200
gagcgcacgg gcttccagct gcggcctgtg gccggcctgc tgtccgcccg ggacttcctg   1260
gccagcctgg ccttccgcgt gttccagtgc acccagtata tccgccacgc gtcctcgccc   1320
atgcactccc ctgagccgga ctgctgccac gagctgctgg ggcacgtgcc catgctggcc   1380
gaccgcacct tcgcgcagtt ctcgcaggac attggcctgg cgtccctggg ggcctcggat   1440
gaggaaattg agaagctgtc cacgctgtac tggttcacgg tggagttcgg gctgtgtaag   1500
cagaacgggg aggtgaaggc ctatggtgcc gggctgctgt cctcctacgg ggagctcctg   1560
cactgcctgt ctgaggagcc tgagattcgg gccttcgacc ctgaggctgc ggccgtgcag   1620
ccctaccaag accagacgta ccagtcagtc tacttcgtgt ctgagagctt cagtgacgcc   1680
aaggacaagc tcaggagcta tgcctcacgc atccagcgcc ccttctccgt gaagttcgac   1740
ccgtacacgc tggccatcga cgtgctggac agcccccagg ccgtgcggcg ctccctggag   1800
ggtgtccagg atgagctgga cacccttgcc catgcgctga gtgccattgg ctaacgcgcg   1860
aaacgcgcgc cggtgaaaca gaccctgaac tttgatctgc tgaaactggc gggcgatgtg   1920
gaaagcaacc cgggcccggc caccatggag aagggccctg tgcgggcacc ggcggagaag   1980
ccgcggggcg ccaggtgcag caatgggttc cccgagcggg atccgccgcg gcccgggccc   2040
agcaggccgg cggagaagcc cccgcggccc gaggccaaga gcgcgcagcc cgcggacggc   2100
tggaagggcg agcggccccg cagcgaggag gataacgagc tgaacctccc taacctggca   2160
gccgcctact cgtccatcct gagctcgctg ggcgagaacc cccagcggca agggctgctc   2220
aagacgccct ggagggcggc ctcggccatg cagttcttca ccaagggcta ccaggagacc   2280
atctcagatg tcctaaacga tgctatattt gatgaagatc atgatgagat ggtgattgtg   2340
aaggacatag acatgttttc catgtgtgag catcacttgg ttccatttgt tggaaaggtc   2400
catattggtt atcttcctaa caagcaagtc cttggcctca gcaaacttgc gaggattgta   2460
```

```
gaaatctata gtagaagact acaagttcag gagcgcctta caaaacaaat tgctgtagca   2520
atcacggaag ccttgcggcc tgctggagtc ggggtagtgg ttgaagcaac acacatgtgt   2580
atggtaatgc gaggtgtaca gaaaatgaac agcaaaactg tgaccagcac aatgttgggt   2640
gtgttccggg aggatccaaa gactcgggaa gagttcctga ctctcattag gagctgagcc   2700
acctaatcaa cctctggatt acaaaatttg tgaaagattg actggtattc ttaactatgt   2760
tgctcctttt acgctatgtg gatacgctgc tttaatgcct ttgtatcatg ctattgcttc   2820
ccgtatggct ttcattttct cctccttgta taaatcctgg ttgctgtctc tttatgagga   2880
gttgtggccc gttgtcaggc aacgtggcgt ggtgtgcact gtgtttgctg acgcaacccc   2940
cactggttgg ggcattgcca ccacctgtca gctcctttcc gggactttcg ctttccccct   3000
ccctattgcc acggcggaac tcatcgccgc ctgccttgcc cgctgctgga caggggctcg   3060
gctgttgggc actgacaatt ccgtggtgtt gtcggggaaa tcatcgtcct ttccctggct   3120
gactgataca atcgatttct ggatccgcag gcctctgcta gcttgactga ctgagataca   3180
gcgtaccttc agctcacaga catgataaga tacattgatg agtttggaca aaccacaact   3240
agaatgcagt gaaaaaaatg ctttatttgt gaaatttgtg atgctattgc tttatttgta   3300
accattataa gctgcaataa acaagttaac aacaacaatt gcattcattt tatgtttcag   3360
gttcaggggg aggtgtggga ggttttttaa gcttaacgcg gtaaccacgt gcggacccaa   3420
cggccgcagg aacccctagt gatggagttg gccactccct ctctgcgcgc tcgctcgctc   3480
actgaggccg ggcgaccaaa ggtcgcccga cgcccgggct ttgcccgggc ggcctcagtg   3540
agcgagcgag cgcgcagctg cctgcagggg cgcctgatgc ggtattttct ccttacgcat   3600
ctgtgcggta tttcacaccg catacgtcaa agcaaccata gtacgcgccc tgtagcggcg   3660
cattaagcgc ggcgggtgtg gtggttacgc gcagcgtgac cgctacactt gccagcgccc   3720
tagcgcccgc tcctttcgct ttcttccctt cctttctcgc cacgttcgcc ggctttcccc   3780
gtcaagctct aaatcggggg ctccctttag ggttccgatt tagtgcttta cggcacctcg   3840
accccaaaaa acttgatttg ggtgatggtt cacgtagtgg gccatcgccc tgatagacgg   3900
tttttcgccc tttgacgttg gagtccacgt tctttaatag tggactcttg ttccaaactg   3960
gaacaacact caaccctatc tcgggctatt cttttgattt ataagggatt ttgccgattt   4020
cggcctattg gttaaaaaat gagctgattt aacaaaaatt taacgcgaat tttaacaaaa   4080
tattaacgtt tacaatttta tggtgcactc tcagtacaat ctgctctgat gccgcatagt   4140
taagccagcc ccgacacccg ccaacacccg ctgacgcgcc ctgacgggct tgtctgctcc   4200
cggcatccgc ttacagacaa gctgtgaccg tctccgggag ctgcatgtgt cagaggtttt   4260
caccgtcatc accgaaacgc gcgagacgaa agggcctcgt gatacgccta tttttatagg   4320
ttaatgtcat gataataatg gtttcttaga cgtcaggtgg cacttttcgg ggaaatgtgc   4380
gcggaacccc tatttgttta tttttctaaa tacattcaaa tatgtatccg ctcatgagac   4440
aataaccctg ataaatgctt caataatatt gaaaaaggaa gagtatgagt attcaacatt   4500
tccgtgtcgc ccttattccc ttttttgcgg cattttgcct tcctgttttt gctcacccag   4560
aaacgctggt gaaagtaaaa gatgctgaag atcagttggg tgcacgagtg ggttacatcg   4620
aactggatct caacagcggt aagatccttg agagttttcg ccccgaagaa cgttttccaa   4680
tgatgagcac ttttaaagtt ctgctatgtg gcgcggtatt atcccgtatt gacgccgggc   4740
aagagcaact cggtcgccgc atacactatt ctcagaatga cttggttgag tactcaccag   4800
```

```
tcacagaaaa gcatcttacg gatggcatga cagtaagaga attatgcagt gctgccataa   4860

ccatgagtga taacactgcg gccaacttac ttctgacaac gatcggagga ccgaaggagc   4920

taaccgcttt tttgcacaac atgggggatc atgtaactcg ccttgatcgt tgggaaccgg   4980

agctgaatga agccatacca aacgacgagc gtgacaccac gatgcctgta gcaatggcaa   5040

caacgttgcg caaactatta actggcgaac tacttactct agcttcccgg caacaattaa   5100

tagactggat ggaggcggat aaagttgcag gaccacttct gcgctcggcc cttccggctg   5160

gctggtttat tgctgataaa tctggagccg gtgagcgtgg gtctcgcggt atcattgcag   5220

cactggggcc agatggtaag ccctcccgta tcgtagttat ctacacgacg gggagtcagg   5280

caactatgga tgaacgaaat agacagatcg ctgagatagg tgcctcactg attaagcatt   5340

ggtaactgtc agaccaagtt tactcatata tactttagat tgatttaaaa cttcattttt   5400

aatttaaaag gatctaggtg aagatccttt ttgataatct catgaccaaa atcccttaac   5460

gtgagttttc gttccactga gcgtcagacc ccgtagaaaa gatcaaagga tcttcttgag   5520

atcctttttt tctgcgcgta atctgctgct tgcaaacaaa aaaaccaccg ctaccagcgg   5580

tggtttgttt gccggatcaa gagctaccaa ctctttttcc gaaggtaact ggcttcagca   5640

gagcgcagat accaaatact gtccttctag tgtagccgta gttaggccac cacttcaaga   5700

actctgtagc accgcctaca tacctcgctc tgctaatcct gttaccagtg gctgctgcca   5760

gtggcgataa gtcgtgtctt accgggttgg actcaagacg atagttaccg gataaggcgc   5820

agcggtcggg ctgaacgggg ggttcgtgca cacagcccag cttggagcga acgacctaca   5880

ccgaactgag atacctacag cgtgagctat gagaaagcgc cacgcttccc gaagggagaa   5940

aggcggacag gtatccggta agcggcaggg tcggaacagg agagcgcacg agggagcttc   6000

cagggggaaa cgcctggtat ctttatagtc ctgtcgggtt tcgccacctc tgacttgagc   6060

gtcgattttt gtgatgctcg tcaggggggc ggagcctatg gaaaaacgcc agcaacgcgg   6120

cctttttacg gttcctggcc ttttgctggc cttttgctca catgt                   6165
```

<210> SEQ ID NO 16
<211> LENGTH: 6126
<212> TYPE: DNA
<213> ORGANISM: Unknown
<220> FEATURE:
<223> OTHER INFORMATION: An example of an AAAV1 vector of the invention. This is similar to SEQ ID NO: 13, but this particular embodiment includes a flexible linker, instead of the EMCV IRES.

<400> SEQUENCE: 16

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccggtc gcgtactagt aatcaattac ggggtcatta gttcatagcc    180

catatatgga gttccgcgtt acataactta cggtaaatgg cccgcctggc tgaccgccca    240

acgacccccg cccattgacg tcaataatga cgtatgttcc catagtaacg ccaataggga    300

ctttccattg acgtcaatgg gtggagtatt tacggtaaac tgcccacttg gcagtacatc    360

aagtgtatca tatgccaagt acgcccccta ttgacgtcaa tgacggtaaa tggcccgcct    420

ggcattatgc ccagtacatg accttatggg actttcctac ttggcagtac atctacgtat    480

tagtcatcgc tattaccatg ctgatgcggt tttggcagta catcaatggg cgtggatagc    540

ggtttgactc acggggattt ccaagtctcc accccattga cgtcaatggg agtttgtttt    600

ggcaccaaaa tcaacgggac tttccaaaat gtcgtaacaa ctccgcccca ttgacgcaaa    660
```

```
tgggcggtag gcgtgtacgg tgggaggtct atataagcag agctggttta gtgaaccgtc    720
agatcagatc tttgtcgatc ctaccatcca ctcgacacac ccgccagcgg ccgctgccaa    780
gcttccgagc tctcgaattc aaaggaggta cccaccatgg ccaccatgag ccccgcgggg    840
cccaaggtcc cctggttccc aagaaaagtg tcagagctgg acaagtgtca tcacctggtc    900
accaagttcg accctgacct ggacttggac cacccgggct tctcggacca ggtgtaccgc    960
cagcgcagga agctgattgc tgagatcgcc ttccagtaca ggcacggcga cccgattccc   1020
cgtgtggagt acaccgccga ggagattgcc acctggaagg aggtctacac cacgctgaag   1080
ggcctctacg ccacgcacgc ctgcggggag cacctggagg cctttgcttt gctggagcgc   1140
ttcagcggct accgggaaga caatatcccc cagctggagg acgtctcccg cttcctgaag   1200
gagcgcacgg gcttccagct gcggcctgtg gccggcctgc tgtccgcccg ggacttcctg   1260
gccagcctgg ccttccgcgt gttccagtgc acccagtata tccgccacgc gtcctcgccc   1320
atgcactccc ctgagccgga ctgctgccac gagctgctgg ggcacgtgcc catgctggcc   1380
gaccgcacct tcgcgcagtt ctcgcaggac attggcctgg cgtccctggg ggcctcggat   1440
gaggaaattg agaagctgtc cacgctgtac tggttcacgg tggagttcgg gctgtgtaag   1500
cagaacgggg aggtgaaggc ctatggtgcc gggctgctgt cctcctacgg ggagctcctg   1560
cactgcctgt ctgaggagcc tgagattcgg gccttcgacc ctgaggctgc ggccgtgcag   1620
ccctaccaag accagacgta ccagtcagtc tacttcgtgt ctgagagctt cagtgacgcc   1680
aaggacaagc tcaggagcta tgcctcacgc atccagcgcc ccttctccgt gaagttcgac   1740
ccgtacacgc tggccatcga cgtgctggac agcccccagg ccgtgcggcg ctccctggag   1800
ggtgtccagg atgagctgga caccccttgcc catgcgctga gtgccattgg ctaaggaggt   1860
ggcgggtccg gggcgggggg tagcggtggc gggggctccg ccaccatgga gaagggccct   1920
gtgcgggcac cggcggagaa gccgcggggc gccaggtgca gcaatgggtt ccccgagcgg   1980
gatccgccgc ggcccgggcc cagcaggccg gcggagaagc ccccgcggcc cgaggccaag   2040
agcgcgcagc ccgcggacgg ctggaagggc gagcggcccc gcagcgagga ggataacgag   2100
ctgaacctcc ctaacctggc agccgcctac tcgtccatcc tgagctcgct gggcgagaac   2160
ccccagcggc aagggctgct caagacgccc tggagggcgg cctcggccat gcagttcttc   2220
accaagggct accaggagac catctcagat gtcctaaacg atgctatatt tgatgaagat   2280
catgatgaga tggtgattgt gaaggacata gacatgtttt ccatgtgtga gcatcacttg   2340
gttccatttg ttggaaaggt ccatattggt tatcttccta acaagcaagt ccttggcctc   2400
agcaaacttg cgaggattgt agaaatctat agtagaagac tacaagttca ggagcgcctt   2460
acaaaacaaa ttgctgtagc aatcacggaa gccttgcggc ctgctggagt cggggtagtg   2520
gttgaagcaa cacacatgtg tatggtaatg cgaggtgtac agaaaatgaa cagcaaaact   2580
gtgaccagca caatgttggg tgtgttccgg gaggatccaa agactcggga agagttcctg   2640
actctcatta ggagctgagc cacctaatca acctctggat tacaaaattt gtgaaagatt   2700
gactggtatt cttaactatg ttgctccttt tacgctatgt ggatacgctg ctttaatgcc   2760
tttgtatcat gctattgctt cccgtatggc tttcattttc tcctccttgt ataaatcctg   2820
gttgctgtct ctttatgagg agttgtggcc cgttgtcagg caacgtggcg tggtgtgcac   2880
tgtgtttgct gacgcaaccc ccactggttg gggcattgcc accacctgtc agctcctttc   2940
cgggactttc gctttccccc tccctattgc cacggcggaa ctcatcgccg cctgccttgc   3000
```

```
ccgctgctgg acaggggctc ggctgttggg cactgacaat tccgtggtgt tgtcggggaa   3060
atcatcgtcc tttccctggc tgactgatac aatcgatttc tggatccgca ggcctctgct   3120
agcttgactg actgagatac agcgtacctt cagctcacag acatgataag atacattgat   3180
gagtttggac aaaccacaac tagaatgcag tgaaaaaaat gctttatttg tgaaatttgt   3240
gatgctattg ctttatttgt aaccattata agctgcaata aacaagttaa caacaacaat   3300
tgcattcatt ttatgtttca ggttcagggg gaggtgtggg aggtttttta agcttaacgc   3360
ggtaaccacg tgcggaccca acggccgcag gaacccctag tgatggagtt ggccactccc   3420
tctctgcgcg ctcgctcgct cactgaggcc gggcgaccaa aggtcgcccg acgcccgggc   3480
tttgcccggg cggcctcagt gagcgagcga gcgcgcagct gcctgcaggg gcgcctgatg   3540
cggtattttc tccttacgca tctgtgcggt atttcacacc gcatacgtca aagcaaccat   3600
agtacgcgcc ctgtagcggc gcattaagcg cggcgggtgt ggtggttacg cgcagcgtga   3660
ccgctacact tgccagcgcc ctagcgcccg ctcctttcgc tttcttccct tcctttctcg   3720
ccacgttcgc cggctttccc cgtcaagctc taaatcgggg gctcccttta gggttccgat   3780
ttagtgcttt acggcacctc gaccccaaaa aacttgattt gggtgatggt tcacgtagtg   3840
ggccatcgcc ctgatagacg gtttttcgcc ctttgacgtt ggagtccacg ttctttaata   3900
gtggactctt gttccaaact ggaacaacac tcaaccctat ctcgggctat tcttttgatt   3960
tataagggat tttgccgatt tcggcctatt ggttaaaaaa tgagctgatt taacaaaaat   4020
ttaacgcgaa ttttaacaaa atattaacgt ttacaatttt atggtgcact ctcagtacaa   4080
tctgctctga tgccgcatag ttaagccagc cccgacaccc gccaacaccc gctgacgcgc   4140
cctgacgggc ttgtctgctc ccggcatccg cttacagaca agctgtgacc gtctccggga   4200
gctgcatgtg tcagaggttt tcaccgtcat caccgaaacg cgcgagacga aagggcctcg   4260
tgatacgcct atttttatag gttaatgtca tgataataat ggtttcttag acgtcaggtg   4320
gcacttttcg gggaaatgtg cgcggaaccc ctatttgttt atttttctaa atacattcaa   4380
atatgtatcc gctcatgaga caataaccct gataaatgct tcaataatat tgaaaaagga   4440
agagtatgag tattcaacat ttccgtgtcg cccttattcc cttttttgcg gcattttgcc   4500
ttcctgtttt tgctcaccca gaaacgctgg tgaaagtaaa agatgctgaa gatcagttgg   4560
gtgcacgagt gggttacatc gaactggatc tcaacagcgg taagatcctt gagagttttc   4620
gccccgaaga acgttttcca atgatgagca cttttaaagt tctgctatgt ggcgcggtat   4680
tatcccgtat tgacgccggg caagagcaac tcggtcgccg catacactat tctcagaatg   4740
acttggttga gtactcacca gtcacagaaa agcatcttac ggatggcatg acagtaagag   4800
aattatgcag tgctgccata accatgagtg ataacactgc ggccaactta cttctgacaa   4860
cgatcggagg accgaaggag ctaaccgctt ttttgcacaa catgggggat catgtaactc   4920
gccttgatcg ttgggaaccg gagctgaatg aagccatacc aaacgacgag cgtgacacca   4980
cgatgcctgt agcaatggca acaacgttgc gcaaactatt aactggcgaa ctacttactc   5040
tagcttcccg gcaacaatta atagactgga tggaggcgga taaagttgca ggaccacttc   5100
tgcgctcggc ccttccggct ggctggttta ttgctgataa atctggagcc ggtgagcgtg   5160
ggtctcgcgg tatcattgca gcactggggc cagatggtaa gccctcccgt atcgtagtta   5220
tctacacgac ggggagtcag gcaactatgg atgaacgaaa tagacagatc gctgagatag   5280
gtgcctcact gattaagcat tggtaactgt cagaccaagt ttactcatat atactttaga   5340
ttgatttaaa acttcatttt taatttaaaa ggatctaggt gaagatcctt tttgataatc   5400
```

```
tcatgaccaa aatcccttaa cgtgagtttt cgttccactg agcgtcagac cccgtagaaa   5460

agatcaaagg atcttcttga gatccttttt ttctgcgcgt aatctgctgc ttgcaaacaa   5520

aaaaaccacc gctaccagcg gtggtttgtt tgccggatca agagctacca actctttttc   5580

cgaaggtaac tggcttcagc agagcgcaga taccaaatac tgtccttcta gtgtagccgt   5640

agttaggcca ccacttcaag aactctgtag caccgcctac atacctcgct ctgctaatcc   5700

tgttaccagt ggctgctgcc agtggcgata agtcgtgtct taccgggttg gactcaagac   5760

gatagttacc ggataaggcg cagcggtcgg gctgaacggg gggttcgtgc acacagccca   5820

gcttggagcg aacgacctac accgaactga gatacctaca gcgtgagcta tgagaaagcg   5880

ccacgcttcc cgaagggaga aaggcggaca ggtatccggt aagcggcagg gtcggaacag   5940

gagagcgcac gagggagctt ccagggggaa acgcctggta tctttatagt cctgtcgggt   6000

ttcgccacct ctgacttgag cgtcgatttt tgtgatgctc gtcagggggg cggagcctat   6060

ggaaaaacgc cagcaacgcg gcctttttac ggttcctggc cttttgctgg ccttttgctc   6120

acatgt                                                              6126
```

<210> SEQ ID NO 17
<211> LENGTH: 4561
<212> TYPE: DNA
<213> ORGANISM: Unknown
<220> FEATURE:
<223> OTHER INFORMATION: A vector carrying AAV2 right and left ITRs. This vector is suitable for the production of AAV vectors.

<400> SEQUENCE: 17

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccggtc gcgtctagtt attaatagta atcaattacg gggtcattag    180

ttcatagccc atatatggag ttccgcgtta cataacttac ggtaaatggc ccgcctggct    240

gaccgcccaa cgacccccgc ccattgacgt caataatgac gtatgttccc atagtaacgc    300

aatagggact ttccattgac gtcaatgggt ggagtattta cggtaaactg cccacttggc    360

agtacatcaa gtgtatcata tgccaagtac gccccctatt gacgtcaatg acggtaaatg    420

gcccgcctgg cattatgccc agtacatgac cttatgggac tttcctactt ggcagtacat    480

ctacgtatta gtcatcgcta ttaccatggt gatgcggttt tggcagtaca tcaatgggcg    540

tggatagcgg tttgactcac ggggatttcc aagtctccac cccattgacg tcaatgggag    600

tttgttttgc accaaaatca acgggacttt ccaaaatgtc gtaacaactc cgccccattg    660

acgcaaatgg gcggtaggcg tgtacggtgg gaggtctata taagcagagc tgtttagtga    720

accgtcagat cgcctggaga cgccatccac gctgttttga cctccataga agacaccggg    780

accgatccag cctccgcgga ttcgaatccc ggccgggaac ggtgcattgg aacgcggatt    840

ccccgtgcca agagtgacgt aagtaccgcc tatagagtct ataggcccac aaaaaatgct    900

ttcttctttt aatatacttt tttgtttatc ttatttctaa tactttccct aatctctttc    960

tttcagggca ataatgatac aatgtatcat gcctctttgc accattctaa agaataacag   1020

tgataatttc tgggttaagg caatagcaat atttctgcat ataaatattt ctgcatataa   1080

attgtaactg atgtaagagg tttcatattg ctaatagcag ctacaatcca gctaccattc   1140

tgcttttatt ttatggttgg gataaggctg gattattctg agtccaagct aggccctttt   1200

gctaatcatg ttcatacctc ttatcttcct cccacagctc ctgggcaacg tgctggtctg   1260
```

```
tgtgctggcc catcactttg gcaaagaatt gggattcgaa catcgattga attcagatcc   1320
gctagtaata cgactcacta tagggagagg atccggtacc gaggagatct gccgccgcga   1380
tcgccggcgc gccagatctc acgcttaact agctagcgga ccgacgcgta cgcggccgct   1440
cgaggattat aaggatgacg acgataaatt cgtcgagcac caccaccacc accactaata   1500
aggtttatcc gatccaccgg atctagataa gatatccgat ccaccggatc tagataactg   1560
atcataatca gccataccac atttgtagag gttttacttg ctttaaaaaa cctcccacac   1620
ctccccctga acctgaaaca taaaatgaat gcaattgttg ttgttaactt gtttattgca   1680
gcttataatg gttacaaata aagcaatagc atcacaaatt tcacaaataa agcatttttt   1740
tcactgcatt ctagttgtgg tttgtccaaa ctcatcaatg tatcttaacg cggtaaccac   1800
gtgcggaccc aacggccgca ggaaccccta gtgatggagt tggccactcc ctctagagct   1860
gcgcgctcgc tcgctcactg aggccgggcg accaaaggtc gcccgacgcc cgggctttgc   1920
ccgggcggcc tcagtgagcg agcgagcgcg cagctgcctg caggggcgcc tgatgcggta   1980
ttttctcctt acgcatctgt gcggtatttc acaccgcata cgtcaaagca accatagtac   2040
gcgccctgta gcggcgcatt aagcgcggcg ggtgtggtgg ttacgcgcag cgtgaccgct   2100
acacttgcca gcgccctagc gcccgctcct ttcgctttct tcccttcctt tctcgccacg   2160
ttcgccggct ttccccgtca agctctaaat cgggggctcc ctttagggtt ccgatttagt   2220
gctttacggc acctcgaccc caaaaaactt gatttgggtg atggttcacg tagtgggcca   2280
tcgccctgat agacggtttt tcgccctttg acgttggagt ccacgttctt taatagtgga   2340
ctcttgttcc aaactggaac aacactcaac cctatctcgg gctattcttt tgatttataa   2400
gggattttgc cgatttcggc ctattggtta aaaaatgagc tgatttaaca aaaatttaac   2460
gcgaatttta acaaaatatt aacgtttaca attttatggt gcactctcag tacaatctgc   2520
tctgatgccg catagttaag ccagccccga cacccgccaa cacccgctga cgcgccctga   2580
cgggcttgtc tgctcccggc atccgcttac agacaagctg tgaccgtctc cgggagctgc   2640
atgtgtcaga ggttttcacc gtcatcaccg aaacgcgcga gacgaaaggg cctcgtgata   2700
cgcctatttt tataggttaa tgtcatgata ataatggttt cttagacgtc aggtggcact   2760
tttcggggaa atgtgcgcgg aacccctatt tgtttatttt tctaaataca ttcaaatatg   2820
tatccgctca tgagacaata accctgataa atgcttcaat aatattgaaa aaggaagagt   2880
atgagtattc aacatttccg tgtcgccctt attccctttt ttgcggcatt ttgccttcct   2940
gtttttgctc acccagaaac gctggtgaaa gtaaaagatg ctgaagatca gttgggtgca   3000
cgagtgggtt acatcgaact ggatctcaac agcggtaaga tccttgagag ttttcgcccc   3060
gaagaacgtt ttccaatgat gagcactttt aaagttctgc tatgtggcgc ggtattatcc   3120
cgtattgacg ccgggcaaga gcaactcggt cgccgcatac actattctca gaatgacttg   3180
gttgagtact caccagtcac agaaaagcat cttacggatg gcatgacagt aagagaatta   3240
tgcagtgctg ccataaccat gagtgataac actgcggcca acttacttct gacaacgatc   3300
ggaggaccga aggagctaac cgcttttttg cacaacatgg gggatcatgt aactcgcctt   3360
gatcgttggg aaccggagct gaatgaagcc ataccaaacg acgagcgtga caccacgatg   3420
cctgtagcaa tggcaacaac gttgcgcaaa ctattaactg gcgaactact tactctagct   3480
tcccggcaac aattaataga ctggatggag gcggataaag ttgcaggacc acttctgcgc   3540
tcggcccttc cggctggctg gtttattgct gataaatctg gagccggtga gcgtgggtct   3600
```

```
cgcggtatca ttgcagcact ggggccagat ggtaagccct cccgtatcgt agttatctac   3660

acgacgggga gtcaggcaac tatggatgaa cgaaatagac agatcgctga gataggtgcc   3720

tcactgatta agcattggta actgtcagac caagtttact catatatact ttagattgat   3780

ttaaaacttc atttttaatt taaaaggatc taggtgaaga tcctttttga taatctcatg   3840

accaaaatcc cttaacgtga gttttcgttc cactgagcgt cagaccccgt agaaaagatc   3900

aaaggatctt cttgagatcc tttttttctg cgcgtaatct gctgcttgca aacaaaaaaa   3960

ccaccgctac cagcggtggt ttgtttgccg gatcaagagc taccaactct ttttccgaag   4020

gtaactggct tcagcagagc gcagatacca aatactgtcc ttctagtgta gccgtagtta   4080

ggccaccact tcaagaactc tgtagcaccg cctacatacc tcgctctgct aatcctgtta   4140

ccagtggctg ctgccagtgg cgataagtcg tgtcttaccg ggttggactc aagacgatag   4200

ttaccggata aggcgcagcg gtcgggctga acggggggtt cgtgcacaca gcccagcttg   4260

gagcgaacga cctacaccga actgagatac ctacagcgtg agctatgaga aagcgccacg   4320

cttcccgaag ggagaaaggc ggacaggtat ccggtaagcg gcagggtcgg aacaggagag   4380

cgcacgaggg agcttccagg gggaaacgcc tggtatcttt atagtcctgt cgggtttcgc   4440

cacctctgac ttgagcgtcg atttttgtga tgctcgtcag gggggcggag cctatggaaa   4500

aacgccagca acgcggcctt tttacggttc ctggcctttt gctggccttt tgctcacatg   4560

t                                                                   4561
```

```
<210> SEQ ID NO 18
<211> LENGTH: 6773
<212> TYPE: DNA
<213> ORGANISM: Unknown
<220> FEATURE:
<223> OTHER INFORMATION: The genetic construct as shown in Fig. 10,
      which includes a CMV promoter and murine GCH1.

<400> SEQUENCE: 18

ggcgatcgcg gctcccgaca tcttggacca ttagctccac aggtatcttc ttccctctag     60

tggtcataac agcagcttca gctacctctc aattcaaaaa acccctcaag acccgtttag    120

aggccccaag gggttatgct atcaatcgtt gcgttacaca cacaaaaaac caacacacat    180

ccatcttcga tggatagcga ttttattatc taactgctga tcgagtgtag ccagatctag    240

taatcaatta cggggtcatt agttcatagc ccatatatgg agttccgcgt tacataactt    300

acggtaaatg gcccgcctgg ctgaccgccc aacgaccccc gcccattgac gtcaataatg    360

acgtatgttc ccatagtaac gccaataggg actttccatt gacgtcaatg ggtggagtat    420

ttacggtaaa ctgcccactt ggcagtacat caagtgtatc atatgccaag tacgccccct    480

attgacgtca atgacggtaa atggcccgcc tggcattatg cccagtacat gaccttatgg    540

gactttccta cttggcagta catctacgta ttagtcatcg ctattaccat gctgatgcgg    600

ttttggcagt acatcaatgg gcgtggatag cggtttgact cacggggatt tccaagtctc    660

caccccattg acgtcaatgg gagtttgttt tggcaccaaa atcaacggga ctttccaaaa    720

tgtcgtaaca actccgcccc attgacgcaa atgggcggta ggcgtgtacg gtgggaggtc    780

tatataagca gagctggttt agtgaaccgt cagatcagat ctagagatcc cgggaccgcc    840

accatgagcc ccgcggggcc caaggtcccc tggttcccaa gaaaagtgtc agagctggac    900

aagtgtcatc acctggtcac caagttcgac cctgacctgg acttggacca cccgggcttc    960

tcggaccagg tgtaccgcca gcgcaggaag ctgattgctg agatcgcctt ccagtacagg   1020
```

-continued

```
cacggcgacc cgattccccg tgtggagtac accgccgagg agattgccac ctggaaggag   1080
gtctacacca cgctgaaggg cctctacgcc acgcacgcct gcggggagca cctggaggcc   1140
tttgctttgc tggagcgctt cagcggctac cgggaagaca atatccccca gctggaggac   1200
gtctcccgct tcctgaagga gcgcacgggc ttccagctgc ggcctgtggc cggcctgctg   1260
tccgcccggg acttcctggc cagcctggcc ttccgcgtgt tccagtgcac ccagtatatc   1320
cgccacgcgt cctcgcccat gcactcccct gagccggact gctgccacga gctgctgggg   1380
cacgtgccca tgctggccga ccgcaccttc gcgcagttct cgcaggacat tggcctggcg   1440
tccctggggg cctcggatga ggaaattgag aagctgtcca cgctgtactg gttcacggtg   1500
gagttcgggc tgtgtaagca gaacggggag gtgaaggcct atggtgccgg gctgctgtcc   1560
tcctacgggg agctcctgca ctgcctgtct gaggagcctg agattcgggc cttcgaccct   1620
gaggctgcgg ccgtgcagcc ctaccaagac cagacgtacc agtcagtcta cttcgtgtct   1680
gagagcttca gtgacgccaa ggacaagctc aggagctatg cctcacgcat ccagcgcccc   1740
ttctccgtga agttcgaccc gtacacgctg gccatcgacg tgctggacag cccccaggcc   1800
gtgcggcgct ccctggaggg tgtccaggat gagctggaca cccttgccca tgcgctgagt   1860
gccattggct aaagcaggtt tccccaactg acacaaaacg tgcaacttga aactccgcct   1920
ggtctttcca ggtctagagg ggtaacactt tgtactgcgt ttggctccac gctcgatcca   1980
ctggcgagtg ttagtaacag cactgttgct tcgtagcgga gcatgacggc cgtgggaact   2040
cctccttggt aacaaggacc cacggggcca aaagccacgc ccacacgggc ccgtcatgtg   2100
tgcaacccca gcacggcgac tttactgcga aacccacttt aaagtgacat tgaaactggt   2160
acccacacac tggtgacagg ctaaggatgc ccttcaggta ccccgaggta acacgcgaca   2220
ctcgggatct gagaagggga ctggggcttc tataaaagcg ctcggtttaa aaagcttcta   2280
tgcctgaata ggtgaccgga ggtcggcacc tttcctttgc aattactgac cacgccacca   2340
tggagaagcc gcggggagtc aggtgcacca atgggttctc cgagcgggag ctgccgcggc   2400
ccggggccag cccgcctgcc gagaagtccc ggccgcccga ggccaagggc gcacagccgg   2460
ccgacgcctg gaaggcaggg cggcaccgca gcgaggagga aaaccaggtg aacctcccca   2520
aactggcggc tgcttactcg tccattctgc tctcgctggg cgaggacccc cagcggcagg   2580
ggctgctcaa gacgccctgg agggcggcca ccgccatgca gtacttcacc aagggatacc   2640
aggagaccat ctcagatgtc ctgaatgatg ctatatttga tgaagatcat gacgagatgg   2700
tgattgtgaa ggacatagat atgttctcca tgtgtgagca tcaccttgtt ccatttgtag   2760
gaagggtcca tattggctat cttcctaaca agcaagtcct tggtctcagt aaacttgcca   2820
ggattgtaga aatctacagt agacgactac aagttcaaga gcgcctcacc aaacagattg   2880
cggtggccat cacagaagcc ttgcagcctg ctggcgttgg agtagtgatt gaagcgacac   2940
acatgtgcat ggtaatgcga ggcgtgcaga aaatgaacag caagactgtc actagcacca   3000
tgctgggcgt gttccgggaa gaccccaaga ctcgggagga gttcctcaca ctaatcagga   3060
gctgaggcca cctaatcaac ctctggatta caaaatttgt gaaagattga ctggtattct   3120
taactatgtt gctcctttta cgctatgtgg atacgctgct ttaatgcctt tgtatcatgc   3180
tattgcttcc cgtatggctt tcattttctc ctccttgtat aaatcctggt tgctgtctct   3240
ttatgaggag ttgtggcccg ttgtcaggca acgtggcgtg gtgtgcactg tgtttgctga   3300
cgcaaccccc actggttggg gcattgccac cacctgtcag ctcctttccg ggactttcgc   3360
tttccccctc cctattgcca cggcggaact catcgccgcc tgccttgccc gctgctggac   3420
```

```
aggggctcgg ctgttgggca ctgacaattc cgtggtgttg tcggggaaat catcgtcctt   3480
tcccatatgc agctcacaga catgataaga tacattgatg agtttggaca aaccacaact   3540
agaatgcagt gaaaaaaatg ctttatttgt gaaatttgtg atgctattgc tttatttgta   3600
accattataa gctgcaataa acaagttaac aacaacaatt gcattcattt tatgtttcag   3660
gttcaggggg aggtgtggga ggttttttaa agcaagtaaa acctctacaa atgtggtatt   3720
ggcccatctc tatcggtatc gtagcataac cccttggggc ctctaaacgg gtcttgaggg   3780
gttttttgtg cccctcgggc cggattgcta tctaccggca ttggcgcaga aaaaaatgcc   3840
tgatgcgacg ctgcgcgtct tatactccca catatgccag attcagcaac ggatacggct   3900
tccccaactt gcccacttcc atacgtgtcc tccttaccag aaatttatcc ttaaggtcgt   3960
cagctatcct gcaggcgatc tctcgatttc gatcaagaca ttcctttaat ggtcttttct   4020
ggacaccact aggggtcaga agtagttcat caaactttct tccctcccta atctcattgg   4080
ttaccttggg ctatcgaaac ttaattaacc agtcaagtca gctacttggc gagatcgact   4140
tgtctgggtt tcgactacgc tcagaattgc gtcagtcaag ttcgatctgg tccttgctat   4200
tgcacccgtt ctccgattac gagtttcatt taaatcatgt gagcaaaagg ccagcaaaag   4260
gccaggaacc gtaaaaaggc cgcgttgctg gcgtttttcc ataggctccg cccccctgac   4320
gagcatcaca aaaatcgacg ctcaagtcag aggtggcgaa acccgacagg actataaaga   4380
taccaggcgt ttccccctgg aagctccctc gtgcgctctc ctgttccgac cctgccgctt   4440
accggatacc tgtccgcctt tctcccttcg ggaagcgtgg cgctttctca tagctcacgc   4500
tgtaggtatc tcagttcggt gtaggtcgtt cgctccaagc tgggctgtgt gcacgaaccc   4560
cccgttcagc ccgaccgctg cgccttatcc ggtaactatc gtcttgagtc caacccggta   4620
agacacgact tatcgccact ggcagcagcc actggtaaca ggattagcag agcgaggtat   4680
gtaggcggtg ctacagagtt cttgaagtgg tggcctaact acggctacac tagaagaaca   4740
gtatttggta tctgcgctct gctgaagcca gttaccttcg gaaaaagagt tggtagctct   4800
tgatccggca aacaaaccac cgctggtagc ggtggttttt ttgtttgcaa gcagcagatt   4860
acgcgcagaa aaaaaggatc tcaagaagat cctttgatct tttctacggg gtctgacgct   4920
cagtggaacg aaaactcacg ttaagggatt ttggtcatga gattatcaaa aaggatcttc   4980
acctagatcc ttttaaatta aaaatgaagt tttaaatcaa tctaaagtat atatgagtaa   5040
acttggtctg acagttacca atgcttaatc agtgaggcac ctatctcagc gatctgtcta   5100
tttcgttcat ccatagttgc atttaaattt ccgaactctc caaggccctc gtcggaaaat   5160
cttcaaacct ttcgtccgat ccatcttgca ggctacctct cgaacgaact atcgcaagtc   5220
tcttggccgg ccttgcgcct tggctattgc ttggcagcgc ctatcgccag gtattactcc   5280
aatcccgaat atccgagatc gggatcaccc gagagaagtt caacctacat cctcaatccc   5340
gatctatccg agatccgagg aatatcgaaa tcggggcgcg cctggtgtac cgagaacgat   5400
cctctcagtg cgagtctcga cgatccatat cgttgcttgg cagtcagcca gtcggaatcc   5460
agcttgggac ccaggaagtc caatcgtcag atattgtact caagcctggt cacggcagcg   5520
taccgatctg tttaaaccta gatattgata gtctgatcgg tcaacgtata atcgagtcct   5580
agcttttgca aacatctatc aagagacagg atcagcagga ggctttcgca tgagtattca   5640
acatttccgt gtcgccctta ttcccttttt tgcggcattt tgccttcctg tttttgctca   5700
cccagaaacg ctggtgaaag taaaagatgc tgaagatcag ttgggtgcgc gagtgggtta   5760
```

```
catcgaactg gatctcaaca gcggtaagat ccttgagagt tttcgccccg aagaacgctt   5820

tccaatgatg agcactttta aagttctgct atgtggcgcg gtattatccc gtattgacgc   5880

cgggcaagag caactcggtc gccgcataca ctattctcag aatgacttgg ttgagtattc   5940

accagtcaca gaaaagcatc ttacggatgg catgacagta agagaattat gcagtgctgc   6000

cataaccatg agtgataaca ctgcggccaa cttacttctg acaacgattg gaggaccgaa   6060

ggagctaacc gcttttttgc acaacatggg ggatcatgta actcgccttg atcgttggga   6120

accggagctg aatgaagcca taccaaacga cgagcgtgac accacgatgc ctgtagcaat   6180

ggcaacaacc ttgcgtaaac tattaactgg cgaactactt actctagctt cccggcaaca   6240

gttgatagac tggatggagg cggataaagt tgcaggacca cttctgcgct cggcccttcc   6300

ggctggctgg tttattgctg ataaatctgg agccggtgag cgtgggtctc gcggtatcat   6360

tgcagcactg gggccagatg gtaagccctc ccgtatcgta gttatctaca cgacggggag   6420

tcaggcaact atggatgaac gaaatagaca gatcgctgag ataggtgcct cactgattaa   6480

gcattggtaa ccgattctag gtgcattggc gcagaaaaaa atgcctgatg cgacgctgcg   6540

cgtcttatac tcccacatat gccagattca gcaacggata cggcttcccc aacttgccca   6600

cttccatacg tgtcctcctt accagaaatt tatccttaag atcccgaatc gtttaaactc   6660

gactctggct ctatcgaatc tccgtcgttt cgagcttacg cgaacagccg tggcgctcat   6720

ttgctcgtcg ggcatcgaat ctcgtcagct atcgtcagct taccttttg gca           6773
```

<210> SEQ ID NO 19
<211> LENGTH: 6390
<212> TYPE: DNA
<213> ORGANISM: Unknown
<220> FEATURE:
<223> OTHER INFORMATION: The genetic construct as shown in Fig. 11. This embodiment includes a CMV promoter and murine GCH1.

<400> SEQUENCE: 19

```
ggcgatcgcg gctcccgaca tcttggacca ttagctccac aggtatcttc ttccctctag     60

tggtcataac agcagcttca gctacctctc aattcaaaaa acccctcaag acccgtttag    120

aggccccaag gggttatgct atcaatcgtt gcgttacaca cacaaaaaac caacacacat    180

ccatcttcga tggatagcga ttttattatc taactgctga tcgagtgtag ccagatctag    240

taatcaatta cggggtcatt agttcatagc ccatatatgg agttccgcgt tacataactt    300

acggtaaatg gcccgcctgg ctgaccgccc aacgaccccc gcccattgac gtcaataatg    360

acgtatgttc ccatagtaac gccaataggg actttccatt gacgtcaatg ggtggagtat    420

ttacggtaaa ctgcccactt ggcagtacat caagtgtatc atatgccaag tacgccccct    480

attgacgtca atgacggtaa atggcccgcc tggcattatg cccagtacat gaccttatgg    540

gactttccta cttggcagta catctacgta ttagtcatcg ctattaccat gctgatgcgg    600

ttttggcagt acatcaatgg gcgtggatag cggtttgact cacggggatt tccaagtctc    660

caccccattg acgtcaatgg gagtttgttt tggcaccaaa atcaacggga ctttccaaaa    720

tgtcgtaaca actccgcccc attgacgcaa atgggcggta ggcgtgtacg gtgggaggtc    780

tatataagca gagctggttt agtgaaccgt cagatcagat ctagagatcc cgggaccgcc    840

accatgagcc ccgcggggcc caaggtcccc tggttcccaa gaaaagtgtc agagctggac    900

aagtgtcatc acctggtcac caagttcgac cctgacctgg acttggacca cccgggcttc    960

tcggaccagg tgtaccgcca gcgcaggaag ctgattgctg agatcgcctt ccagtacagg   1020
```

-continued

```
cacggcgacc cgattccccg tgtggagtac accgccgagg agattgccac ctggaaggag   1080
gtctacacca cgctgaaggg cctctacgcc acgcacgcct gcggggagca cctggaggcc   1140
tttgctttgc tggagcgctt cagcggctac cgggaagaca atatccccca gctggaggac   1200
gtctcccgct tcctgaagga gcgcacgggc ttccagctgc ggcctgtggc cggcctgctg   1260
tccgcccggg acttcctggc cagcctggcc ttccgcgtgt tccagtgcac ccagtatatc   1320
cgccacgcgt cctcgcccat gcactcccct gagccggact gctgccacga gctgctgggg   1380
cacgtgccca tgctggccga ccgcaccttc gcgcagttct cgcaggacat tggcctggcg   1440
tccctggggg cctcggatga ggaaattgag aagctgtcca cgctgtactg gttcacggtg   1500
gagttcgggc tgtgtaagca gaacggggag gtgaaggcct atggtgccgg gctgctgtcc   1560
tcctacgggg agctcctgca ctgcctgtct gaggagcctg agattcgggc cttcgaccct   1620
gaggctgcgg ccgtgcagcc ctaccaagac cagacgtacc agtcagtcta cttcgtgtct   1680
gagagcttca gtgacgccaa ggacaagctc aggagctatg cctcacgcat ccagcgcccc   1740
ttctccgtga agttcgaccc gtacacgctg gccatcgacg tgctggacag cccccaggcc   1800
gtgcggcgct ccctggaggg tgtccaggat gagctggaca cccttgccca tgcgctgagt   1860
gccattggct aacgcgcgaa acgcgcgccg gtgaaacaga ccctgaactt tgatctgctg   1920
aaactggcgg gcgatgtgga aagcaacccg ggcccgatgg agaagccgcg gggagtcagg   1980
tgcaccaatg ggttctccga gcgggagctg ccgcggcccg gggccagccc gcctgccgag   2040
aagtcccggc cgcccgaggc caagggcgca cagccggccg acgcctggaa ggcagggcgg   2100
caccgcagcg aggaggaaaa ccaggtgaac ctccccaaac tggcggctgc ttactcgtcc   2160
attctgctct cgctgggcga ggacccccag cggcaggggc tgctcaagac gccctggagg   2220
gcggccaccg ccatgcagta cttcaccaag ggataccagg agaccatctc agatgtcctg   2280
aatgatgcta tatttgatga agatcatgac gagatggtga ttgtgaagga catagatatg   2340
ttctccatgt gtgagcatca ccttgttcca tttgtaggaa gggtccatat tggctatctt   2400
cctaacaagc aagtccttgg tctcagtaaa cttgccagga ttgtagaaat ctacagtaga   2460
cgactacaag ttcaagagcg cctcaccaaa cagattgcgg tggccatcac agaagccttg   2520
cagcctgctg gcgttggagt agtgattgaa gcgacacaca tgtgcatggt aatgcgaggc   2580
gtgcagaaaa tgaacagcaa gactgtcact agcaccatgc tgggcgtgtt ccgggaagac   2640
cccaagactc gggaggagtt cctcacacta atcaggagct gaggccacct aatcaacctc   2700
tggattacaa aatttgtgaa agattgactg gtattcttaa ctatgttgct ccttttacgc   2760
tatgtggata cgctgcttta atgcctttgt atcatgctat tgcttcccgt atggctttca   2820
ttttctcctc cttgtataaa tcctggttgc tgtctcttta tgaggagttg tggcccgttg   2880
tcaggcaacg tggcgtggtg tgcactgtgt ttgctgacgc aacccccact ggttggggca   2940
ttgccaccac ctgtcagctc ctttccggga ctttcgcttt ccccctccct attgccacgg   3000
cggaactcat cgccgcctgc cttgcccgct gctggacagg ggctcggctg ttgggcactg   3060
acaattccgt ggtgttgtcg gggaaatcat cgtcctttcc catatgcagc tcacagacat   3120
gataagatac attgatgagt ttggacaaac cacaactaga atgcagtgaa aaaaatgctt   3180
tatttgtgaa atttgtgatg ctattgcttt atttgtaacc attataagct gcaataaaca   3240
agttaacaac aacaattgca ttcattttat gtttcaggtt cagggggagg tgtgggaggt   3300
tttttaaagc aagtaaaacc tctacaaatg tggtattggc ccatctctat cggtatcgta   3360
gcataacccc ttggggcctc taaacgggtc ttgaggggtt ttttgtgccc ctcgggccgg   3420
```

```
attgctatct accggcattg gcgcagaaaa aaatgcctga tgcgacgctg cgcgtcttat   3480
actcccacat atgccagatt cagcaacgga tacggcttcc ccaacttgcc cacttccata   3540
cgtgtcctcc ttaccagaaa tttatcctta aggtcgtcag ctatcctgca ggcgatctct   3600
cgatttcgat caagacattc ctttaatggt cttttctgga caccactagg ggtcagaagt   3660
agttcatcaa actttcttcc ctccctaatc tcattggtta ccttgggcta tcgaaactta   3720
attaaccagt caagtcagct acttggcgag atcgacttgt ctgggtttcg actacgctca   3780
gaattgcgtc agtcaagttc gatctggtcc ttgctattgc acccgttctc cgattacgag   3840
tttcatttaa atcatgtgag caaaaggcca gcaaaaggcc aggaaccgta aaaaggccgc   3900
gttgctggcg tttttccata ggctccgccc ccctgacgag catcacaaaa atcgacgctc   3960
aagtcagagg tggcgaaacc cgacaggact ataaagatac caggcgtttc cccctggaag   4020
ctccctcgtg cgctctcctg ttccgaccct gccgcttacc ggatacctgt ccgcctttct   4080
cccttcggga agcgtggcgc tttctcatag ctcacgctgt aggtatctca gttcggtgta   4140
ggtcgttcgc tccaagctgg gctgtgtgca cgaacccccc gttcagcccg accgctgcgc   4200
cttatccggt aactatcgtc ttgagtccaa cccggtaaga cacgacttat cgccactggc   4260
agcagccact ggtaacagga ttagcagagc gaggtatgta ggcggtgcta cagagttctt   4320
gaagtggtgg cctaactacg gctacactag aagaacagta tttggtatct gcgctctgct   4380
gaagccagtt accttcggaa aaagagttgg tagctcttga tccggcaaac aaaccaccgc   4440
tggtagcggt ggtttttttg tttgcaagca gcagattacg cgcagaaaaa aaggatctca   4500
agaagatcct ttgatctttt ctacggggtc tgacgctcag tggaacgaaa actcacgtta   4560
agggattttg gtcatgagat tatcaaaaag gatcttcacc tagatccttt taaattaaaa   4620
atgaagtttt aaatcaatct aaagtatata tgagtaaact tggtctgaca gttaccaatg   4680
cttaatcagt gaggcaccta tctcagcgat ctgtctattt cgttcatcca tagttgcatt   4740
taaatttccg aactctccaa ggccctcgtc ggaaaatctt caaacctttc gtccgatcca   4800
tcttgcaggc tacctctcga acgaactatc gcaagtctct tggccggcct tgcgccttgg   4860
ctattgcttg gcagcgccta tcgccaggta ttactccaat cccgaatatc cgagatcggg   4920
atcacccgag agaagttcaa cctacatcct caatcccgat ctatccgaga tccgaggaat   4980
atcgaaatcg gggcgcgcct ggtgtaccga gaacgatcct ctcagtgcga gtctcgacga   5040
tccatatcgt tgcttggcag tcagccagtc ggaatccagc ttgggaccca ggaagtccaa   5100
tcgtcagata ttgtactcaa gcctggtcac ggcagcgtac cgatctgttt aaacctagat   5160
attgatagtc tgatcggtca acgtataatc gagtcctagc ttttgcaaac atctatcaag   5220
agacaggatc agcaggaggc tttcgcatga gtattcaaca tttccgtgtc gcccttattc   5280
cctttttgc ggcattttgc cttcctgttt ttgctcaccc agaaacgctg gtgaaagtaa   5340
aagatgctga agatcagttg ggtgcgcgag tgggttacat cgaactggat ctcaacagcg   5400
gtaagatcct tgagagtttt cgccccgaag aacgctttcc aatgatgagc acttttaaag   5460
ttctgctatg tggcgcggta ttatcccgta ttgacgccgg gcaagagcaa ctcggtcgcc   5520
gcatacacta ttctcagaat gacttggttg agtattcacc agtcacagaa aagcatctta   5580
cggatggcat gacagtaaga gaattatgca gtgctgccat aaccatgagt gataacactg   5640
cggccaactt acttctgaca acgattggag gaccgaagga gctaaccgct tttttgcaca   5700
acatgggggga tcatgtaact cgccttgatc gttgggaacc ggagctgaat gaagccatac   5760
```

```
caaacgacga gcgtgacacc acgatgcctg tagcaatggc aacaaccttg cgtaaactat   5820

taactggcga actacttact ctagcttccc ggcaacagtt gatagactgg atggaggcgg   5880

ataaagttgc aggaccactt ctgcgctcgg cccttccggc tggctggttt attgctgata   5940

aatctggagc cggtgagcgt gggtctcgcg gtatcattgc agcactgggg ccagatggta   6000

agccctcccg tatcgtagtt atctacacga cggggagtca ggcaactatg gatgaacgaa   6060

atagacagat cgctgagata ggtgcctcac tgattaagca ttggtaaccg attctaggtg   6120

cattggcgca gaaaaaaatg cctgatgcga cgctgcgcgt cttatactcc cacatatgcc   6180

agattcagca acggatacgg cttccccaac ttgcccactt ccatacgtgt cctccttacc   6240

agaaatttat ccttaagatc ccgaatcgtt taaactcgac tctggctcta tcgaatctcc   6300

gtcgtttcga gcttacgcga acagccgtgg cgctcatttg ctcgtcgggc atcgaatctc   6360

gtcagctatc gtcagcttac ctttttggca                                     6390
```

Figure 12:
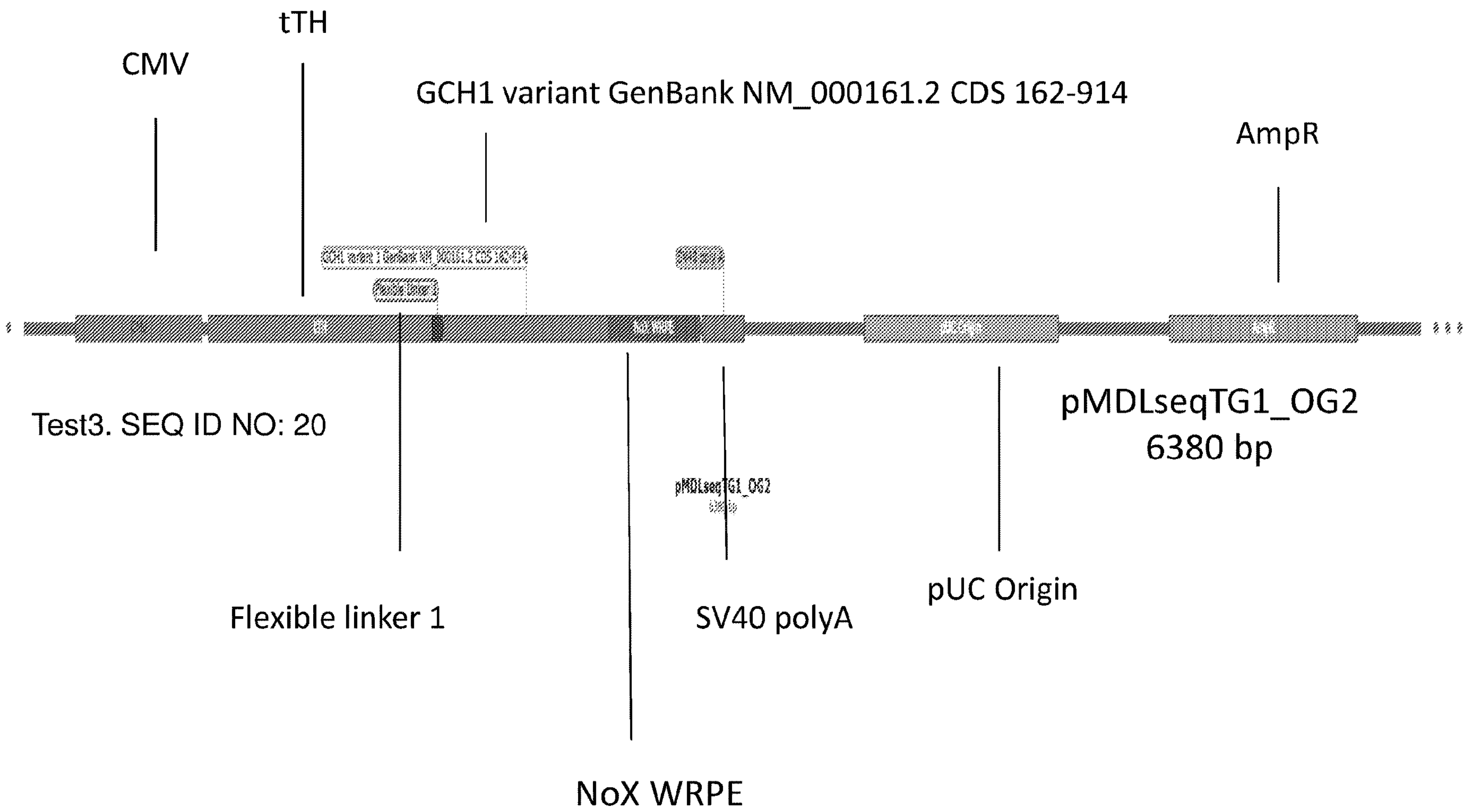
FIG. 12 is a plasmid map of an eighth embodiment of the construct of the invention, showing the features of SEQ ID NO: 20.

```
<210> SEQ ID NO 20
<211> LENGTH: 6380
<212> TYPE: DNA
<213> ORGANISM: Unknown
<220> FEATURE:
<223> OTHER INFORMATION: The genetic construct is shown in Fig. 12. This
      embodiment includes a CMV promoter and murine GCH1.

<400> SEQUENCE: 20
```

```
ggcgatcgcg gctcccgaca tcttggacca ttagctccac aggtatcttc ttccctctag     60

tggtcataac agcagcttca gctacctctc aattcaaaaa acccctcaag acccgtttag    120

aggccccaag gggttatgct atcaatcgtt gcgttacaca cacaaaaaac caacacacat    180

ccatcttcga tggatagcga ttttattatc taactgctga tcgagtgtag ccagatctag    240

taatcaatta cggggtcatt agttcatagc ccatatatgg agttccgcgt tacataactt    300

acggtaaatg gcccgcctgg ctgaccgccc aacgaccccc gcccattgac gtcaataatg    360

acgtatgttc ccatagtaac gccaataggg actttccatt gacgtcaatg ggtggagtat    420

ttacggtaaa ctgcccactt ggcagtacat caagtgtatc atatgccaag tacgccccct    480

attgacgtca atgacggtaa atggcccgcc tggcattatg cccagtacat gaccttatgg    540

gactttccta cttggcagta catctacgta ttagtcatcg ctattaccat gctgatgcgg    600

ttttggcagt acatcaatgg gcgtggatag cggtttgact cacggggatt tccaagtctc    660

caccccattg acgtcaatgg gagtttgttt tggcaccaaa atcaacggga ctttccaaaa    720

tgtcgtaaca actccgcccc attgacgcaa atgggcggta ggcgtgtacg gtgggaggtc    780

tatataagca gagctggttt agtgaaccgt cagatcagat ctagagatcc cgggaccgcc    840

accatgagcc ccgcggggcc caaggtcccc tggttcccaa gaaaagtgtc agagctggac    900

aagtgtcatc acctggtcac caagttcgac cctgacctgg acttggacca cccgggcttc    960

tcggaccagg tgtaccgcca gcgcaggaag ctgattgctg agatcgcctt ccagtacagg   1020

cacggcgacc cgattccccg tgtggagtac accgccgagg agattgccac ctggaaggag   1080

gtctacacca cgctgaaggg cctctacgcc acgcacgcct gcggggagca cctggaggcc   1140

tttgctttgc tggagcgctt cagcggctac cgggaagaca atatccccca gctggaggac   1200

gtctcccgct tcctgaagga gcgcacgggc ttccagctgc ggcctgtggc cggcctgctg   1260

tccgcccggg acttcctggc cagcctggcc ttccgcgtgt tccagtgcac ccagtatatc   1320

cgccacgcgt cctcgcccat gcactcccct gagccggact gctgccacga gctgctgggg   1380
```

```
cacgtgccca tgctggccga ccgcaccttc gcgcagttct cgcaggacat tggcctggcg   1440
tccctggggg cctcggatga ggaaattgag aagctgtcca cgctgtactg gttcacggtg   1500
gagttcgggc tgtgtaagca gaacggggag gtgaaggcct atggtgccgg gctgctgtcc   1560
tcctacgggg agctcctgca ctgcctgtct gaggagcctg agattcgggc cttcgaccct   1620
gaggctgcgg ccgtgcagcc ctaccaagac cagacgtacc agtcagtcta cttcgtgtct   1680
gagagcttca gtgacgccaa ggacaagctc aggagctatg cctcacgcat ccagcgcccc   1740
ttctccgtga agttcgaccc gtacacgctg gccatcgacg tgctggacag cccccaggcc   1800
gtgcggcgct ccctggaggg tgtccaggat gagctggaca cccttgccca tgcgctgagt   1860
gccattggcg gaggtggcgg gtccgggggc gggggtagcg gtggcggggg ctccgccacc   1920
atggagaagg gccctgtgcg ggcaccggcg gagaagccgc ggggcgccag gtgcagcaat   1980
gggttccccg agcgggatcc gccgcggccc gggcccagca ggccggcgga gaagcccccg   2040
cggcccgagg ccaagagcgc gcagcccgcg gacggctgga agggcgagcg gccccgcagc   2100
gaggaggata acgagctgaa cctccctaac ctggcagccg cctactcgtc catcctgagc   2160
tcgctgggcg agaaccccca gcggcaaggg ctgctcaaga cgccctggag ggcggcctcg   2220
gccatgcagt tcttcaccaa gggctaccag gagaccatct cagatgtcct aaacgatgct   2280
atatttgatg aagatcatga tgagatggtg attgtgaagg acatagacat gttttccatg   2340
tgtgagcatc acttggttcc atttgttgga aaggtccata ttggttatct tcctaacaag   2400
caagtccttg gcctcagcaa acttgcgagg attgtagaaa tctatagtag aagactacaa   2460
gttcaggagc gccttacaaa acaaattgct gtagcaatca cggaagcctt gcggcctgct   2520
ggagtcgggg tagtggttga agcaacacac atgtgtatgg taatgcgagg tgtacagaaa   2580
atgaacagca aaactgtgac cagcacaatg ttgggtgtgt tccgggagga tccaaagact   2640
cgggaagagt tcctgactct cattaggagc tgagccacct aatcaacctc tggattacaa   2700
aatttgtgaa agattgactg gtattcttaa ctatgttgct ccttttacgc tatgtggata   2760
cgctgcttta atgcctttgt atcatgctat tgcttcccgt atggctttca ttttctcctc   2820
cttgtataaa tcctggttgc tgtctcttta tgaggagttg tggcccgttg tcaggcaacg   2880
tggcgtggtg tgcactgtgt ttgctgacgc aacccccact ggttggggca ttgccaccac   2940
ctgtcagctc ctttccggga ctttcgcttt ccccctccct attgccacgg cggaactcat   3000
cgccgcctgc cttgcccgct gctggacagg ggctcggctg ttgggcactg acaattccgt   3060
ggtgttgtcg gggaaatcat cgtcctttcc catatgcagc tcacagacat gataagatac   3120
attgatgagt ttggacaaac cacaactaga atgcagtgaa aaaaatgctt tatttgtgaa   3180
atttgtgatg ctattgcttt atttgtaacc attataagct gcaataaaca agttaacaac   3240
aacaattgca ttcattttat gtttcaggtt cagggggagg tgtgggaggt tttttaaagc   3300
aagtaaaacc tctacaaatg tggtattggc ccatctctat cggtatcgta gcataacccc   3360
ttggggcctc taaacgggtc ttgaggggtt ttttgtgccc ctcgggccgg attgctatct   3420
accggcattg gcgcagaaaa aaatgcctga tgcgacgctg cgcgtcttat actcccacat   3480
atgccagatt cagcaacgga tacggcttcc ccaacttgcc cacttccata cgtgtcctcc   3540
ttaccagaaa tttatcctta aggtcgtcag ctatcctgca ggcgatctct cgatttcgat   3600
caagacattc ctttaatggt cttttctgga caccactagg ggtcagaagt agttcatcaa   3660
actttcttcc ctccctaatc tcattggtta ccttgggcta tcgaaactta attaaccagt   3720
caagtcagct acttggcgag atcgacttgt ctgggtttcg actacgctca gaattgcgtc   3780
```

```
agtcaagttc gatctggtcc ttgctattgc acccgttctc cgattacgag tttcatttaa   3840
atcatgtgag caaaaggcca gcaaaaggcc aggaaccgta aaaaggccgc gttgctggcg   3900
tttttccata ggctccgccc ccctgacgag catcacaaaa atcgacgctc aagtcagagg   3960
tggcgaaacc cgacaggact ataaagatac caggcgtttc cccctggaag ctccctcgtg   4020
cgctctcctg ttccgaccct gccgcttacc ggatacctgt ccgcctttct cccttcggga   4080
agcgtggcgc tttctcatag ctcacgctgt aggtatctca gttcggtgta ggtcgttcgc   4140
tccaagctgg gctgtgtgca cgaacccccc gttcagcccg accgctgcgc cttatccggt   4200
aactatcgtc ttgagtccaa cccggtaaga cacgacttat cgccactggc agcagccact   4260
ggtaacagga ttagcagagc gaggtatgta ggcggtgcta cagagttctt gaagtggtgg   4320
cctaactacg gctacactag aagaacagta tttggtatct gcgctctgct gaagccagtt   4380
accttcggaa aaagagttgg tagctcttga tccggcaaac aaaccaccgc tggtagcggt   4440
ggtttttttg tttgcaagca gcagattacg cgcagaaaaa aaggatctca agaagatcct   4500
ttgatctttt ctacggggtc tgacgctcag tggaacgaaa actcacgtta agggattttg   4560
gtcatgagat tatcaaaaag gatcttcacc tagatccttt taaattaaaa atgaagtttt   4620
aaatcaatct aaagtatata tgagtaaact tggtctgaca gttaccaatg cttaatcagt   4680
gaggcaccta tctcagcgat ctgtctattt cgttcatcca tagttgcatt taaatttccg   4740
aactctccaa ggccctcgtc ggaaaatctt caaacctttc gtccgatcca tcttgcaggc   4800
tacctctcga acgaactatc gcaagtctct tggccggcct tgcgccttgg ctattgcttg   4860
gcagcgccta tcgccaggta ttactccaat cccgaatatc cgagatcggg atcacccgag   4920
agaagttcaa cctacatcct caatcccgat ctatccgaga tccgaggaat atcgaaatcg   4980
gggcgcgcct ggtgtaccga gaacgatcct ctcagtgcga gtctcgacga tccatatcgt   5040
tgcttggcag tcagccagtc ggaatccagc ttgggaccca ggaagtccaa tcgtcagata   5100
ttgtactcaa gcctggtcac ggcagcgtac cgatctgttt aaacctagat attgatagtc   5160
tgatcggtca acgtataatc gagtcctagc ttttgcaaac atctatcaag agacaggatc   5220
agcaggaggc tttcgcatga gtattcaaca tttccgtgtc gcccttattc ccttttttgc   5280
ggcattttgc cttcctgttt ttgctcaccc agaaacgctg gtgaaagtaa aagatgctga   5340
agatcagttg ggtgcgcgag tgggttacat cgaactggat ctcaacagcg gtaagatcct   5400
tgagagtttt cgccccgaag aacgctttcc aatgatgagc acttttaaag ttctgctatg   5460
tggcgcggta ttatcccgta ttgacgccgg gcaagagcaa ctcggtcgcc gcatacacta   5520
ttctcagaat gacttggttg agtattcacc agtcacagaa aagcatctta cggatggcat   5580
gacagtaaga gaattatgca gtgctgccat aaccatgagt gataacactg cggccaactt   5640
acttctgaca acgattggag gaccgaagga gctaaccgct tttttgcaca acatggggga   5700
tcatgtaact cgccttgatc gttgggaacc ggagctgaat gaagccatac caaacgacga   5760
gcgtgacacc acgatgcctg tagcaatggc aacaaccttg cgtaaactat taactggcga   5820
actacttact ctagcttccc ggcaacagtt gatagactgg atggaggcgg ataaagttgc   5880
aggaccactt ctgcgctcgg cccttccggc tggctggttt attgctgata aatctggagc   5940
cggtgagcgt gggtctcgcg gtatcattgc agcactgggg ccagatggta agccctcccg   6000
tatcgtagtt atctacacga cggggagtca ggcaactatg gatgaacgaa atagacagat   6060
cgctgagata ggtgcctcac tgattaagca ttggtaaccg attctaggtg cattggcgca   6120
```

```
gaaaaaaatg cctgatgcga cgctgcgcgt cttatactcc cacatatgcc agattcagca   6180

acggatacgg cttccccaac ttgcccactt ccatacgtgt cctccttacc agaaatttat   6240

ccttaagatc ccgaatcgtt taaactcgac tctggctcta tcgaatctcc gtcgtttcga   6300

gcttacgcga acagccgtgg cgctcatttg ctcgtcgggc atcgaatctc gtcagctatc   6360

gtcagcttac ctttttggca                                               6380


<210> SEQ ID NO 21
<211> LENGTH: 497
<212> TYPE: PRT
<213> ORGANISM: Homo sapiens

<400> SEQUENCE: 21

Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Val Ala Ala Ala Ala Ala Ala Val Pro Ser Glu Pro
    50                  55                  60

Gly Asp Pro Leu Glu Ala Val Ala Phe Glu Glu Lys Glu Gly Lys Ala
65                  70                  75                  80

Val Leu Asn Leu Leu Phe Ser Pro Arg Ala Thr Lys Pro Ser Ala Leu
                85                  90                  95

Ser Arg Ala Val Lys Val Phe Glu Thr Phe Glu Ala Lys Ile His His
            100                 105                 110

Leu Glu Thr Arg Pro Ala Gln Arg Pro Arg Ala Gly Gly Pro His Leu
        115                 120                 125

Glu Tyr Phe Val Arg Leu Glu Val Arg Arg Gly Asp Leu Ala Ala Leu
    130                 135                 140

Leu Ser Gly Val Arg Gln Val Ser Glu Asp Val Arg Ser Pro Ala Gly
145                 150                 155                 160

Pro Lys Val Pro Trp Phe Pro Arg Lys Val Ser Glu Leu Asp Lys Cys
                165                 170                 175

His His Leu Val Thr Lys Phe Asp Pro Asp Leu Asp Leu Asp His Pro
            180                 185                 190

Gly Phe Ser Asp Gln Val Tyr Arg Gln Arg Arg Lys Leu Ile Ala Glu
        195                 200                 205

Ile Ala Phe Gln Tyr Arg His Gly Asp Pro Ile Pro Arg Val Glu Tyr
    210                 215                 220

Thr Ala Glu Glu Ile Ala Thr Trp Lys Glu Val Tyr Thr Thr Leu Lys
225                 230                 235                 240

Gly Leu Tyr Ala Thr His Ala Cys Gly Glu His Leu Glu Ala Phe Ala
                245                 250                 255

Leu Leu Glu Arg Phe Ser Gly Tyr Arg Glu Asp Asn Ile Pro Gln Leu
            260                 265                 270

Glu Asp Val Ser Arg Phe Leu Lys Glu Arg Thr Gly Phe Gln Leu Arg
        275                 280                 285

Pro Val Ala Gly Leu Leu Ser Ala Arg Asp Phe Leu Ala Ser Leu Ala
    290                 295                 300

Phe Arg Val Phe Gln Cys Thr Gln Tyr Ile Arg His Ala Ser Ser Pro
305                 310                 315                 320

Met His Ser Pro Glu Pro Asp Cys Cys His Glu Leu Leu Gly His Val
```

```
                325                 330                 335

Pro Met Leu Ala Asp Arg Thr Phe Ala Gln Phe Ser Gln Asp Ile Gly
            340                 345                 350

Leu Ala Ser Leu Gly Ala Ser Asp Glu Glu Ile Glu Lys Leu Ser Thr
        355                 360                 365

Leu Tyr Trp Phe Thr Val Glu Phe Gly Leu Cys Lys Gln Asn Gly Glu
    370                 375                 380

Val Lys Ala Tyr Gly Ala Gly Leu Leu Ser Ser Tyr Gly Glu Leu Leu
385                 390                 395                 400

His Cys Leu Ser Glu Glu Pro Glu Ile Arg Ala Phe Asp Pro Glu Ala
                405                 410                 415

Ala Ala Val Gln Pro Tyr Gln Asp Gln Thr Tyr Gln Ser Val Tyr Phe
            420                 425                 430

Val Ser Glu Ser Phe Ser Asp Ala Lys Asp Lys Leu Arg Ser Tyr Ala
        435                 440                 445

Ser Arg Ile Gln Arg Pro Phe Ser Val Lys Phe Asp Pro Tyr Thr Leu
    450                 455                 460

Ala Ile Asp Val Leu Asp Ser Pro Gln Ala Val Arg Arg Ser Leu Glu
465                 470                 475                 480

Gly Val Gln Asp Glu Leu Asp Thr Leu Ala His Ala Leu Ser Ala Ile
                485                 490                 495

Gly


<210> SEQ ID NO 22
<211> LENGTH: 342
<212> TYPE: PRT
<213> ORGANISM: Homo sapiens

<400> SEQUENCE: 22

Met Ser Pro Ala Gly Pro Lys Val Pro Trp Phe Pro Arg Lys Val Ser
1               5                   10                  15

Glu Leu Asp Lys Cys His His Leu Val Thr Lys Phe Asp Pro Asp Leu
            20                  25                  30

Asp Leu Asp His Pro Gly Phe Ser Asp Gln Val Tyr Arg Gln Arg Arg
        35                  40                  45

Lys Leu Ile Ala Glu Ile Ala Phe Gln Tyr Arg His Gly Asp Pro Ile
    50                  55                  60

Pro Arg Val Glu Tyr Thr Ala Glu Glu Ile Ala Thr Trp Lys Glu Val
65                  70                  75                  80

Tyr Thr Thr Leu Lys Gly Leu Tyr Ala Thr His Ala Cys Gly Glu His
                85                  90                  95

Leu Glu Ala Phe Ala Leu Leu Glu Arg Phe Ser Gly Tyr Arg Glu Asp
            100                 105                 110

Asn Ile Pro Gln Leu Glu Asp Val Ser Arg Phe Leu Lys Glu Arg Thr
        115                 120                 125

Gly Phe Gln Leu Arg Pro Val Ala Gly Leu Leu Ser Ala Arg Asp Phe
    130                 135                 140

Leu Ala Ser Leu Ala Phe Arg Val Phe Gln Cys Thr Gln Tyr Ile Arg
145                 150                 155                 160

His Ala Ser Ser Pro Met His Ser Pro Glu Pro Asp Cys Cys His Glu
                165                 170                 175

Leu Leu Gly His Val Pro Met Leu Ala Asp Arg Thr Phe Ala Gln Phe
            180                 185                 190

Ser Gln Asp Ile Gly Leu Ala Ser Leu Gly Ala Ser Asp Glu Glu Ile
```

```
        195                 200                 205

Glu Lys Leu Ser Thr Leu Tyr Trp Phe Thr Val Glu Phe Gly Leu Cys
    210                 215                 220

Lys Gln Asn Gly Glu Val Lys Ala Tyr Gly Ala Gly Leu Leu Ser Ser
225                 230                 235                 240

Tyr Gly Glu Leu Leu His Cys Leu Ser Glu Glu Pro Glu Ile Arg Ala
                245                 250                 255

Phe Asp Pro Glu Ala Ala Ala Val Gln Pro Tyr Gln Asp Gln Thr Tyr
            260                 265                 270

Gln Ser Val Tyr Phe Val Ser Glu Ser Phe Ser Asp Ala Lys Asp Lys
        275                 280                 285

Leu Arg Ser Tyr Ala Ser Arg Ile Gln Arg Pro Phe Ser Val Lys Phe
    290                 295                 300

Asp Pro Tyr Thr Leu Ala Ile Asp Val Leu Asp Ser Pro Gln Ala Val
305                 310                 315                 320

Arg Arg Ser Leu Glu Gly Val Gln Asp Glu Leu Asp Thr Leu Ala His
                325                 330                 335

Ala Leu Ser Ala Ile Gly
            340


<210> SEQ ID NO 23
<211> LENGTH: 250
<212> TYPE: PRT
<213> ORGANISM: Homo sapiens

<400> SEQUENCE: 23

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205

Thr His Met Cys Met Val Met Arg Gly Val Gln Lys Met Asn Ser Lys
    210                 215                 220
```

```
Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250
```

<210> SEQ ID NO 24
<211> LENGTH: 15
<212> TYPE: PRT
<213> ORGANISM: Unknown
<220> FEATURE:
<223> OTHER INFORMATION: Flexible linker sequence.

<400> SEQUENCE: 24

```
Gly Gly Gly Gly Ser Gly Gly Gly Gly Ser Gly Gly Gly Gly Ser
1               5                   10                  15
```

<210> SEQ ID NO 25
<211> LENGTH: 663
<212> TYPE: DNA
<213> ORGANISM: Unknown
<220> FEATURE:
<223> OTHER INFORMATION: CMV promoter

<400> SEQUENCE: 25

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tcc                                                                  663
```

<210> SEQ ID NO 26
<211> LENGTH: 1338
<212> TYPE: DNA
<213> ORGANISM: Unknown
<220> FEATURE:
<223> OTHER INFORMATION: OIPR sequence

<400> SEQUENCE: 26

```
attgggatct tcacacagca ggtaaggttg cgggccgggc ctgggccggg tccgggccgg     60

gtattgcccg cctaatgagc gggctttttt ttcttacccc ttcttccgct tcctcgctca    120

ctgactcgct gcgctcggtc gttcggctgc ggcgagcggt atcagctcac tcaaaggcgg    180

taatacggtt atccacagaa tcaggggata acgcaggaaa gaacatgtga gcaaaaggcc    240

agcaaaaggc caggaaccgt aaaaaggccg cgttgctggc gtttttccat aggctccgcc    300

cccctgacga gcatcacaaa aatcgacgct caagtcagag gtggcgaaac ccgacaggac    360

tataaagata ccaggcgttt ccccctggaa gctccctcgt gcgctctcct gttccgaccc    420

tgccgcttac cggatacctg tccgcctttc tcccttcggg aagcgtggcg ctttctcata    480
```

```
gctcacgctg taggtatctc agttcggtgt aggtcgttcg ctccaagctg ggctgtgtgc    540

acgaaccccc cgttcagccc gaccgctgcg ccttatccgg taactatcgt cttgagtcca    600

acccggtaag acacgactta tcgccactgg cagcagccac tggtaacagg attagcagag    660

cgaggtatgt aggcggtgct acagagttct tgaagtggtg gcctaactac ggctacacta    720

gaagaacagt atttggtatc tgcgctctgc tgaagccagt taccttcgga aaaagagttg    780

gtagctcttg atccggcaaa caaaccaccg ctggtagcgg tggttttttt gtttgcaagc    840

agcagattac gcgcagaaaa aaaggatctc aagaagatcc tttgatcttt tctacggggt    900

ctgacgctca gtggaacgaa aactcacgtt aagggatttt ggtcatgaga ttatcaaaaa    960

ggatcttcac ctagatcctt ttaaattaaa aatgaagttt taaatcaatc taaagtatat   1020

atgagtaaac ttggtctgac agttaccaat gcttaatcag tgaggcacct atctcagcga   1080

tctgtctatt tcgttcatcc atagttgcct gactcctgca aaccacgttg tggtagaatt   1140

ggtaaagaga gtcgtgtaaa atatcgagtt cgcacatctt gttgtctgat tattgatttt   1200

tggcgaaacc atttgatcat atgacaagat gtgtatctac cttaacttaa tgattttgat   1260

aaaaatcatt aggtaccccg gcccgcactg acccctggtg ttgctttttt tttttaggcc   1320

gcaagctgaa gcgtgtcc                                                 1338


<210> SEQ ID NO 27
<211> LENGTH: 60
<212> TYPE: DNA
<213> ORGANISM: Unknown
<220> FEATURE:
<223> OTHER INFORMATION: E2A sequence

<400> SEQUENCE: 27

cagtgtacta attatgctct cttgaaattg gctggagatg ttgagagcaa ccctggacct     60


<210> SEQ ID NO 28
<211> LENGTH: 66
<212> TYPE: DNA
<213> ORGANISM: Unknown
<220> FEATURE:
<223> OTHER INFORMATION: F2A sequence.

<400> SEQUENCE: 28

gtgaaacaga ctttgaattt tgaccttctc aagttggcgg gagacgtgga gtccaaccct     60

ggacct                                                                66


<210> SEQ ID NO 29
<211> LENGTH: 57
<212> TYPE: DNA
<213> ORGANISM: Unknown
<220> FEATURE:
<223> OTHER INFORMATION: P2A sequence.

<400> SEQUENCE: 29

gccacgaact tctctctgtt aaagcaagca ggagatgttg aagaaaaccc cgggcct        57


<210> SEQ ID NO 30
<211> LENGTH: 54
<212> TYPE: DNA
<213> ORGANISM: Unknown
<220> FEATURE:
<223> OTHER INFORMATION: T2A sequence.

<400> SEQUENCE: 30

gagggcaggg gaagtcttct aacatgcggg gacgtggagg aaaatcccgg cccc           54
```

```
<210> SEQ ID NO 31
<211> LENGTH: 9
<212> TYPE: DNA
<213> ORGANISM: Unknown
<220> FEATURE:
<223> OTHER INFORMATION: glycine-serine-glycine spacer sequence.

<400> SEQUENCE: 31

ggaagcgga                                                              9
```

The invention claimed is:

1. A genetic construct comprising;

a promoter operably linked to a first coding sequence, which encodes tyrosine hydroxylase (TH) and a second coding sequence, which encodes GTP cyclohydrolase 1 (GCH1);

wherein the first coding sequence comprises a sequence of SEQ ID NO: 1 or SEQ ID No: 2, or a fragment or variant thereof having greater than 85% sequence identity to SEQ ID No: 1 or SEQ ID No: 2; or a nucleotide sequence encoding an amino acid sequence as set out in SEQ ID NO: 21 or SEQ ID No: 22, or a fragment or variant thereof having greater than 85% sequence identity to SEQ ID No: 21 or SEQ ID No: 22; wherein the second coding sequence comprises a sequence of SEQ ID NO: 4, or a fragment or variant thereof having greater than 85% sequence identity to SEQ ID No: 4; or a nucleotide sequence encoding an amino acid sequence as set out in SEQ ID NO: 23, or a fragment or variant thereof having greater than 85% sequence identity to SEQ ID No: 23;

wherein the second coding sequence is 3' to the first coding sequence and the first and second coding sequences are part of a single operon;

wherein the genetic construct further comprises between the first and second coding sequences a sequence encoding a 2A peptide spacer so as to encode a fusion protein in which the TH protein is fused to the GCH1 protein via the 2A peptide spacer that is cleavable to thereby yield a functional TH protein and a functional GCH1 protein; and wherein the genetic construct does not encode aromatic amino acid decarboxylase (AADC).

2. The genetic construct according to claim 1, wherein the first coding sequence comprises a nucleotide sequence as set out in SEQ ID NO: 1 or SEQ ID No: 2, or comprises a nucleotide sequence encoding an amino acid sequence as set out in SEQ ID NO: 21 or SEQ ID No: 22.

3. The genetic construct according to claim 1, wherein the second coding sequence comprises a nucleotide sequence as set out in SEQ ID NO: 4, or comprises a nucleotide sequence encoding an amino acid sequence as set out in SEQ ID NO: 23.

4. The genetic construct according to claim 1, wherein the promoter is a constitutive promoter, an activatable promoter, an inducible promoter, or a tissue-specific promoter, optionally wherein the promoter comprises a CMV promoter or a human synapsin promoter.

5. The genetic construct according to claim 1, wherein the promoter comprises a nucleotide sequence as set out in SEQ ID No: 5 or 25.

6. The genetic construct according to claim 1, wherein the genetic construct comprises: (i) a nucleotide sequence encoding Woodchuck Hepatitis Virus Post-transcriptional Regulatory Element (WPRE), and optionally wherein the WPRE comprises a nucleic acid sequence as set out in SEQ ID NO: 10 or SEQ ID NO: 11; (ii) a nucleotide sequence encoding a polyA tail, and/or optionally wherein the polyA tail comprises a nucleic acid sequence as set out in SEQ ID No: 12; and/or (iii) left and/or right Inverted Terminal Repeat sequences (ITRs).

7. The genetic construct according to claim 1, wherein the construct comprises a sequence as set out in SEQ ID NO: 18, SEQ ID NO: 19, or SEQ ID NO: 20.

8. A recombinant vector comprising the genetic construct according to claim 1.

9. The recombinant vector according to claim 8, wherein the recombinant vector is a recombinant AAV vector.

10. The recombinant vector according to claim 8, wherein the recombinant vector comprises a sequence as set out in SEQ ID NO: 13, SEQ ID NO: 14, SEQ ID NO: 15, or SEQ ID NO: 16.

11. A method of treating, preventing, or ameliorating a neurodegenerative disorder in a subject, the method comprising administering, to a subject in need of such treatment, a therapeutically effective amount of the genetic construct according to claim 1.

12. The method of claim 11, wherein the neurodegenerative disorder is a disease associated with catecholamine dysfunction, optionally wherein the disease associated with catecholamine dysfunction is characterised by a dopamine deficiency.

13. The method of claim 12, wherein the neurodegenerative disorder is Parkinson's disease.

14. A pharmaceutical composition comprising the genetic construct according to claim 1, and a pharmaceutically acceptable vehicle.

* * * * *